(12) United States Patent
Saito et al.

(10) Patent No.: US 8,062,638 B1
(45) Date of Patent: Nov. 22, 2011

(54) PREVENTION AND TREATMENT OF DISEASES ASSOCIATED WITH BLOOD COAGULATION

(75) Inventors: Hiroyuki Saito, Gotenba (JP); Takehisa Kitazawa, Gotenba (JP); Kazutaka Yoshihashi, Gotenba (JP); Kunihiro Hattori, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 66 days.

(21) Appl. No.: 10/089,501

(22) PCT Filed: Sep. 29, 2000

(86) PCT No.: PCT/JP00/06802
§ 371 (c)(1),
(2), (4) Date: Apr. 22, 2002

(87) PCT Pub. No.: WO01/24626
PCT Pub. Date: Apr. 12, 2001

(30) Foreign Application Priority Data

| Oct. 1, 1999 | (JP) | 11-281843 |
| Oct. 1, 1999 | (JP) | 11-282120 |
| Oct. 1, 1999 | (JP) | 11-282134 |
| Oct. 1, 1999 | (JP) | 11-282167 |
| Oct. 1, 1999 | (JP) | 11-282188 |
| Oct. 1, 1999 | (JP) | 11-282192 |

(51) Int. Cl.
*A61K 39/395* (2006.01)
*C07K 14/745* (2006.01)
*C07K 16/24* (2006.01)

(52) U.S. Cl. ............... 424/145.1; 424/130.1; 424/133.1; 424/141.1; 514/14.3; 514/14.5; 514/14.9

(58) Field of Classification Search ................ 424/130.1
See application file for complete search history.

(56) References Cited

U.S. PATENT DOCUMENTS

| 5,346,991 A | 9/1994 | Roy et al. | |
| 5,879,677 A * | 3/1999 | del Zoppo | 424/145.1 |
| 5,986,065 A * | 11/1999 | Wong et al. | 530/388.22 |
| 6,287,794 B1 * | 9/2001 | Safar et al. | 435/13 |
| 6,677,436 B1 * | 1/2004 | Sato et al. | 530/387.3 |

FOREIGN PATENT DOCUMENTS

| EP | 0 278 776 A2 | 8/1988 |
| EP | 1 069 185 A | 1/2001 |
| JP | 8-217799 | 8/1996 |
| WO | WO 88/07543 | 10/1988 |
| WO | WO 88/07543 A1 | 10/1988 |
| WO | WO 88/09817 | 12/1988 |
| WO | WO 88/09817 A1 | 12/1988 |
| WO | WO 98/40408 A1 | 9/1998 |

OTHER PUBLICATIONS

Eskens, F., "Angiogenesis inhibitors in clinical development; where are we now and where are we going?", 2004, Brit. J. Cancer, vol. 90: pp. 1-7.*

Weiner, L. et al., "An overview of Monoclonal Antibody Therapy of Cancer", 1999, Sem. in Oncol., vol. 26: pp. 41-50.*

Asakura et al, Thrombosis Research, 1995, vol. 80, No. 3, pp. 217-224.*

Randolph, G. et al. "Role of Tissue Factor in Adhesion of Mononuclear Phagocytes to and Trafficking Through Endothelium in Vitro," Blood (Dec. 1, 1998), vol. 92, No. 11, pp. 4167-4177.

Giesen, P. et al. "Blood-borne tissue factor: Another view of thrombosis," Proc. Natl. Acad. Sci. (Mar. 1999), vol. 96, pp. 2311-2315.

Nakayama, T. et al., (1999) vol. 39, No. 4, 298-302.

Drake, T. et al. "Functional Tissue Factor is Entirely Cell Surface Expressed on Lipopolysaccharide-stimulated Human Blood Monocytes and a Constitutively Tissue Factor-producing Neoplastic Cell Line," *The Journal of Cell Biology* (Jul. 1989), vol. 109, pp. 389-395, The Rockefeller University Press.

Ran, S. et al. "Infarction of Solid Hodgkin's Tumors in Mice by Antibody-directed Targeting of Tissue Factor to Tumor Vasculature," *Cancer Research* (Oct. 15, 1998), pp. 4646-4653.

Bellamy, W. et al. "Development of an orthotopic SCID mouse-human tumor xenograft model displaying the multidrug-resistant phenotype," *Cancer Chemother Pharmacol* (1996), vol. 37, pp. 305-316.

Huang, X. et al. "Tumor Infarction in Mice by Antibody-Directed Targeting of Tissue Factor to Tumor Vasculature," *Science* (Jan. 24, 1997), vol. 275, pp. 547-550.

Morrissey, J. "Molecular Cloning of the cDNA for Tissue Factor, the Cellular Receptor for the Initiation of the Coagulation Protease Cascade," *Cell* (Jul. 3, 1987), vol. 50, pp. 129-135, Cell Press.

Davie, et al., "Waterfall Sequence for Intrinsic Blood Clotting," *Science*, vol. 145, pp. 1310-1312 (1964), USA.

Giesen, et al., "Blood-borne tissue factor: Another view of thrombosis," *Proc. Natl. Acad. Sci.*, vol. 96, pp. 2311-2315 (1999), Medical Sciences, USA.

Taylor, et al., "Lethal *E. coli* Septic Shock is Prevented by Blocking Tissue Factor With Monoclonal Antibody," *Circulatory Shock*, vol. 33, pp. 127-134 (1991), Wiley-Liss, Inc., USA.

(Continued)

*Primary Examiner* — Bridget E Bunner
*Assistant Examiner* — Fozia Hamud
(74) *Attorney, Agent, or Firm* — Foley & Lardner LLP

(57) ABSTRACT

Provided herein is an animal having a persistent hypercoagulable state by implanting a cell, for example a tumor cell, in which the gene of human tissue factor is implanted to an experimental animal such as a mouse and then growing the cell, thereby persistently supplying human tissue factor to the experimental animal. This animal model is useful for research and development of therapeutic agents for diseases having a persistent hypercoagulable state. Also provided are preventive or therapeutic agents for diseases having a persistent hypercoagulable state, a hypercoagulable state resulting from infections, venous thrombosis, arterial thrombosis, and diseases resulting from the hypertrophy of vascular media, the agent comprising an antibody against human tissue factor (human TF) as an active ingredient.

3 Claims, 14 Drawing Sheets

OTHER PUBLICATIONS

MacFarlane, "Haemotology, An Enzyme Cascade in the Blood Clotting Mechanism, and its Function as a Biochemical Amplifier", *Nature*, vol. 202, pp. 498-499 (1964), USA.

Pawashe, et al., "A Monoclonal Antibody Against Rabbit Tissue Factor Inhibits Thrombus Formation in Stenotic Injured Rabbit Carotid Arteries," *Circulation Research*, vol. 74, No. 1, pp. 56-63 (1994), USA.

Levi, et al., "Inhibition of Endotoxin-induced Activation of Coagulation and Fibrinolysis by Pentoxifylline or by a Monoclonal Anti-tissue factor Antibody in Chimpanzees," *The Journal of Clinical Investigation, Inc.*, vol. 93, pp. 114-120 (1994), USA.

Huang, et al., "Tumor Infarction in Mice by Antiboby-Directed Targeting of Tissue Factor to Tumor Vasculature," *Science*, vol. 275, pp. 547, 550 (1997).

Holst, et al., "Local Application of Recombinant Active-site Inhibited Human Clotting Factor VIIa Reduces Thrombus Weight and Improves Patency in a Rabbit Venous Thrombosis Model," *Eur J Vasc Endovasc Surg*, vol. 15, pp. 515-520 (1998), W.B. Saunders Company Ltd., USA.

Bellamy, et al., "Development of an orthotopic SCID mouse-human tumor xenograft mocjel displaying the multidrug-resistant phenotype," *Cancer Chemother Phamracol*, vol. 37, pp. 305-316 (1996), Springer-Verlag, Germany.

Randolph, et al., "Role of Tissue Factor in Adhesion of Mononuclear Phagocytes to and Trafficking Through Endothelium In Vitro," *Blood*, vol. 92, No. 11, pp. 4167-4177 (1998), The American Society of Hematology, USA.

Himber, et al., "Dissociation of Antithrombotic Effect and Bleeding Time Prolongation in Rabbits by Inhibiting Tissue Factor Function," *Thromb Haemost*, vol. 78, pp. 1142-1149 (1997), Schattauer Verlag, Germany.

Ragni, et al., "Monoclonal Antibody Against Tissue Factor Shortens Tissue Plasminogen Activator Lysis Time and Prevents Reocclusion in a Rabbit Model of Carotid Artery Thrombosis," *Circulation*, vol. 93, No. 10, pp. 1913-1918 (1996), American Heart Association, Inc., USA.

Morrissey, et al., "Molecular Cloning of the cDNA for Tissue Factor, the Cellular Receptor for the Initiation of the Coagulation Protease Cascade," *Cell*, vol. 50, pp. 129-135 (1987), Cell Press, USA.

Ran, et al., "Infarction of Solid Hodgkin's Tumors in Mice by Antibody-directed Targeting of Tissue Factor to Tumor Vasculature," *Cancer Research*, vol. 58, pp. 4646-4653 (1998), USA.

Drake, et al., "Functional Tissue Factor is Entirely Cell Surface Expressed on Lipopolysaccharaide-stimulated Human Blood Monocytes and a Constitutively Tissue Factor-producing Neoplastic Cell Line," *The Journal of Cell Biology*, vol. 109, pp. 389-395 (1989), The Rockefeller University Press, USA.

Callander, et al., "Immunohistochemical Identification of Tissue Factor in Solid Tumors," *Cancer*, vol. 70, pp. 1194-1201 (1992), USA.

Konigsberg, et al., "The TF: VIIa Complex: Clinical Significance, Structure-function Relationships and Its Role in Signaling and Metastasis," *Thromb Haemost*, vol. 86, pp. 757-771 (2001), Schattauer GmbH, Germany.

Harker, et al., "Antithrombotic and Antilesion Benefits without Hemorrhagic Risks by Inhibiting Tissue Factor Pathway," *Haemostasis*, vol. 26, pp. 76-82 (1996), S. Karger AG, Switzerland.

Hougie, "Reactions of Stuart Factor and Factor VII with Brain and Factor V", *P.S.E.B.M.*, vol. 101, pp. 132-135 (1959), National Heart Institute, USA.

Nakayama, et al., "Anticoagulation Therapy by Inhibiting Extrinsic Pathway", *Translation of Hematology & Oncology*, vol. 39, No. 4, pp. 298-302 (1999), First Department of Internal Medicine, Nagoya University School of Medicine, Japan.

Mohri, M. et al., The antithrombotic effects of recombinant human soluble thrombomodulin (rhs TM) on tissue factor-induced disseminated intravascular coagulation in crab-eating monkeys (*Macaca fascicularis*); Blood Coagulation arid Fibronolysis, vol. 8, pp. 274-283, 1997 Rapid Science Publishers.

Bromberg, M. E., et al., "Role of Tissue Factor in Metastatsis: Functions of the Cytoplasmic and Extracellular Domains of the Molecule" Trombosis and Haemostasis, Stuttgart, DE, vol. 82, pp. 88-92 (Jul. 1999).

Carmeliet, P., et al., "Molecules in focus. Tissue factor", International Journal of Biochemistry and Cell Biology, vol. 30, No. 6, pp. 661-667 (Jun. 1998).

Graham, P. C., et al., "Low levels of tissue factor are compatible with development and hemostatsis in mice" Journal of Clinical Investigation, vol. 101, No. 3, pp. 560-569 (Feb. 1, 1998).

Jang, I. K., et al., "Antithrombotic effect of a monoclonal antibody against tissue factor in a rabbit model of platelet-mediated arterial thrombosis", Arteriosclerosis and Thrombosis: A Journal of Vascular Biology/American Heart Association, vol. 12, No. 8, pp. 948-954 (Aug. 1992).

Levi, M., et al., "Inhibition of endotoxin-induced activation of coagulation and fibrinolysis by pentoxifylline or by a monoclonal anti-tissue factor antibody in chimpanzees", Journal of Clinical Investigation, vol. 93, No. 1, pp. 114-120 (1994).

Massimo, R., et al., "Monoclonal antibody against tissue factor shortens tissue plasminogen activator lysis time and prevents reocclusion in a rabbit model of carotid artery thrombosis", Circulation, vol. 93, No. 10, pp. 1913-1918 (1996).

Melis, E., et al., "Thrombophilia in mice expressing a tissue factor variant lacking its transmembrane and cytosolic domain" Biochemical and Biophysical Research Communications, Academic Press Inc., Orlando, FL, US, vol. 333, No. 2, pp. 488-495 (Jul. 29, 2005).

Taylor, F. B, Jr., et al., "Lethal *Escherichia-coli* Septic Shock is Prevented by Blocking Tissue Factor With Monoclonal Antibody", Circulatory Shock, vol. 33, No. 3, pp. 127-134 (1991).

Tomaru et al., "Prevention of Thrombus Formation by Local Administration of Anti-Tissue Factor Antibody," Jpn. Circ. J., Feb. 28, 2009, 62(Supp.1):320, #0860, with English translation, 2 pages.

* cited by examiner

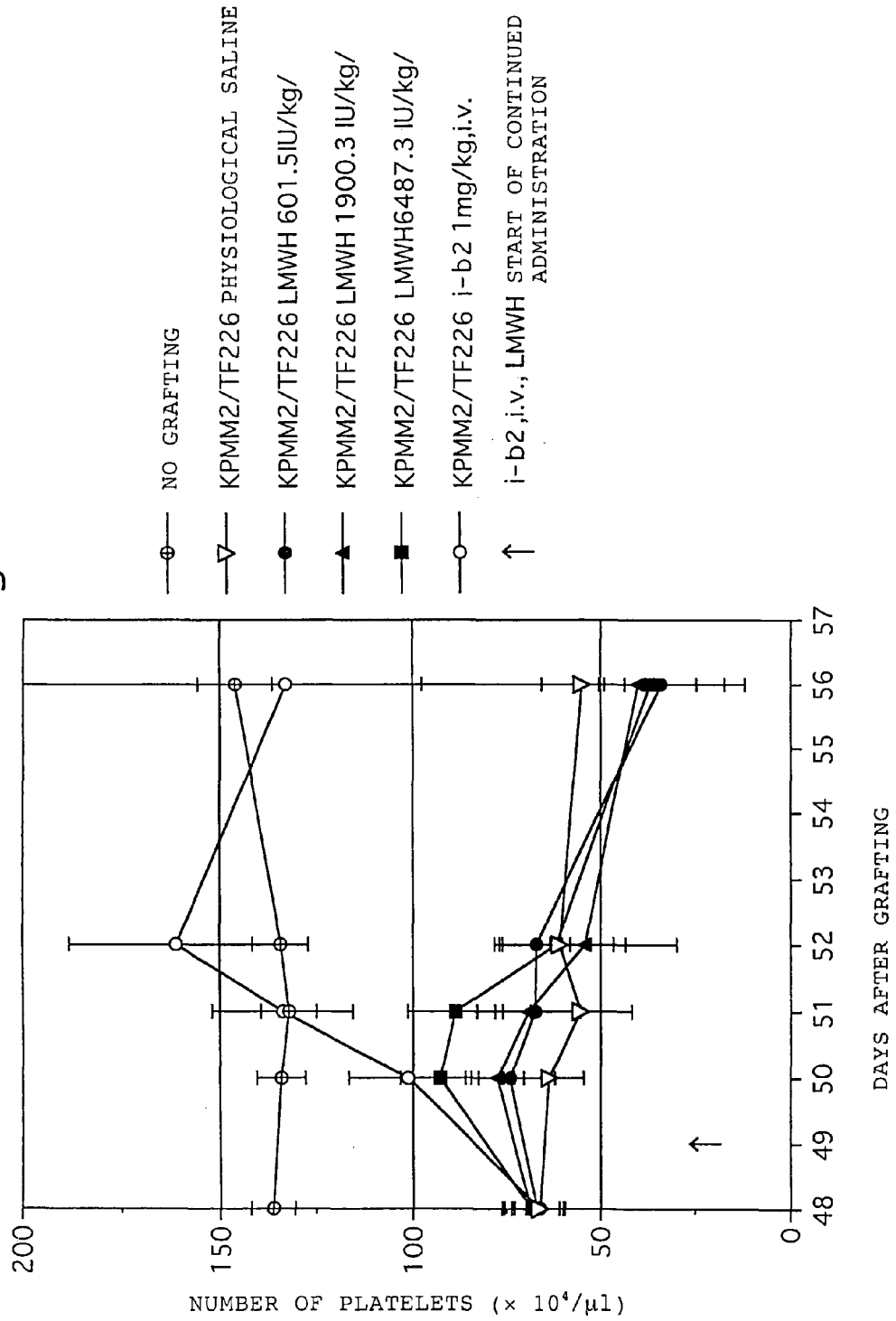

```
                        SEQUENCE LISTING

<160> NUMBER OF SEQ ID NOS: 104

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Primer
      MHC-G1

<400> SEQUENCE: 1
ggatcccggg ccagtggata gacagatg                                       28

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer
      MKC

<400> SEQUENCE: 2
ggatcccggg tggatggtgg gaagatg                                        27

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: M13 Primer
      M4 sequence

<400> SEQUENCE: 3
gttttcccag tcacgac                                                   17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: M13 Primer
      RV

<400> SEQUENCE: 4
caggaaacag ctatgac                                                   17

<210> SEQ ID NO 5
<211> LENGTH: 408
```

```
<212> TYPE: DNA
<213> ORGANISM: Mus sp.
<220> FEATURE:
<221> NAME/KEY: CDS
<222> LOCATION: (1)..(408)
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)
<223> OTHER INFORMATION: Nucleotide sequence coding for H chain V region
      of anti-TF mouse monoclonal antibody ATR-5

<400> SEQUENCE: 5 atg aaa tgc agc tgg gtc atc ttc ttc ctg atg gca gtg gtt aca ggg          48
Met Lys Cys Ser Trp Val Ile Phe Phe Leu Met Ala Val Val Thr Gly
            -15                 -10                 -5 gtc aat tca gag gtt cag ctg cag cag tct ggg act aac ctt gtg agg          96
Val Asn Ser Glu Val Gln Leu Gln Gln Ser Gly Thr Asn Leu Val Arg
     -1   1               5                   10 cca ggg gcc tta gtc aag ttg tcc tgc aaa ggt tct ggc ttc aac att         144
Pro Gly Ala Leu Val Lys Leu Ser Cys Lys Gly Ser Gly Phe Asn Ile
 15                  20                  25 aaa gac tac tat atg cac tgg gtg aag cag agg cct gaa cag ggc ctg         192
Lys Asp Tyr Tyr Met His Trp Val Lys Gln Arg Pro Glu Gln Gly Leu
 30                  35                  40                  45 gag tgg att gga ggg aat gat cct gcg aat ggt cat agt atg tat gac         240
Glu Trp Ile Gly Gly Asn Asp Pro Ala Asn Gly His Ser Met Tyr Asp
             50                  55                  60 ccg aaa ttc cag ggc aag gcc agt ata aca gca gac aca tcc tcc aac         288
Pro Lys Phe Gln Gly Lys Ala Ser Ile Thr Ala Asp Thr Ser Ser Asn
             65                  70                  75 aca gcc tac ctg cag ctc agc agc ctg aca tct gag gac act gcc gtc         336
Thr Ala Tyr Leu Gln Leu Ser Ser Leu Thr Ser Glu Asp Thr Ala Val
         80                  85                  90 tat ttc tgt gct aga gac tcg ggc tat gct atg gac tac tgg ggt caa         384
Tyr Phe Cys Ala Arg Asp Ser Gly Tyr Ala Met Asp Tyr Trp Gly Gln
     95                 100                 105 gga acc tca gtc acc gtc tcc tca                                         408
Gly Thr Ser Val Thr Val Ser Ser
110                 115

<210> SEQ ID NO 6
<211> LENGTH: 381
<212> TYPE: DNA
<213> ORGANISM: Mus sp.
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)
<223> OTHER INFORMATION: Nucleotide sequence coding for L chain V region
      of anti-TF mouse monoclonal antibody ATR-5

<400> SEQUENCE: 6 atg agg gcc cct gct cag ttt ttt ggg atc ttg ttg ctc tgg ttt cca          48
Met Arg Ala Pro Ala Gln Phe Phe Gly Ile Leu Leu Leu Trp Phe Pro
-20                 -15                 -10                 -5 ggt atc aga tgt gac atc aag atg acc cag tct cca tcc tct atg tat          96
Gly Ile Arg Cys Asp Ile Lys Met Thr Gln Ser Pro Ser Ser Met Tyr
             -1   1               5                   10 gca tcg ctg gga gag aga gtc act atc act tgc aag gcg agt cag gac         144
```

```
Ala Ser Leu Gly Glu Arg Val Thr Ile Thr Cys Lys Ala Ser Gln Asp
             15                  20                  25 att aaa agc ttt tta agt tgg tac cag caa aaa cca tgg aaa tct cct      192
Ile Lys Ser Phe Leu Ser Trp Tyr Gln Gln Lys Pro Trp Lys Ser Pro
         30                  35                  40 aag acc ctg atc tat tat gca aca agc ttg gca gat ggg gtc cca tca      240
Lys Thr Leu Ile Tyr Tyr Ala Thr Ser Leu Ala Asp Gly Val Pro Ser
 45                  50                  55                  60 aga ttc agt ggc agt gga tct ggg caa gat tat tct cta acc atc aac      288
Arg Phe Ser Gly Ser Gly Ser Gly Gln Asp Tyr Ser Leu Thr Ile Asn
                 65                  70                  75 aac ctg gag tct gac gat aca gca act tat tat tgt cta cag cat ggt      336
Asn Leu Glu Ser Asp Asp Thr Ala Thr Tyr Tyr Cys Leu Gln His Gly
             80                  85                  90 gag agc ccg tac acg ttc gga ggg ggg acc aag ctg gaa ata aaa          381
Glu Ser Pro Tyr Thr Phe Gly Gly Gly Thr Lys Leu Glu Ile Lys
         95                 100                 105

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Primer
      ch5HS

<400> SEQUENCE: 7
gtctgtcgac ccaccatgaa atgcagctgg gtcat                                35

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Primer
      ch5HA

<400> SEQUENCE: 8
tgttgctagc tgaggagacg gtgactga                                        28

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Primer
      ch5LS

<400> SEQUENCE: 9
gtctagatct ccaccatgag ggcccctgct cagtt                                35

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer
      ch5LA

<400> SEQUENCE: 10
tgttcgtacg tttttatttcc agcttggt                                       28

<210> SEQ ID NO 11
<211> LENGTH: 104
<212> TYPE: DNA
<213> ORGANISM: Artificial Sequence
```

-continued

```
<220> FEATURE:
<223> OTHER INFORMATION: Description of Artificial Sequence: CDR
      grafting primer hR5Hv1S

<400> SEQUENCE: 11
ttctgtcgac ccaccatgaa atgcagctgg gtcatcttct tcctgatggc agtggttaca      60
ggggttaact cacaggtgca gctgttggag tctggagctg tgct                      104

<210> SEQ ID NO 12
<211> LENGTH: 108
<212> TYPE: DNA
<213> ORGANISM: Artificial Sequence
<220> FEATURE:
<223> OTHER INFORMATION: Description of Artificial Sequence: CDR
      grafting primer hR5Hv2S

<400> SEQUENCE: 12
acaggtgcag ctgttggagt ctggagctgt gctggcaagg cctgggactt ccgtgaagat      60
ctcctgcaag gcttccggat tcaacattaa agactactat atgcattg                  108

<210> SEQ ID NO 13
<211> LENGTH: 108
<212> TYPE: DNA
<213> ORGANISM: Artificial Sequence
<220> FEATURE:
<223> OTHER INFORMATION: Description of Artificial Sequence: CDR
      grafting primer hR5Hv4S

<400> SEQUENCE: 13
gaatggccat agtatgtatg acccgaaatt ccagggcagg gccaaactga ctgcagccac      60
atccgccagt attgcctact tggagttctc gagcctgaca aatgagga                  108

<210> SEQ ID NO 14
<211> LENGTH: 110
<212> TYPE: DNA
<213> ORGANISM: Artificial Sequence
<220> FEATURE:
<223> OTHER INFORMATION: Description of Artificial Sequence: CDR
      grafting primer hR5Hv3A

<400> SEQUENCE: 14
tcatacatac tatggccatt cgcaggatca ttcccaccaa tccattctag accctgtcca      60
ggcctctgtt ttacccaatg catatagtag tctttaatgt tgaatccgga              110

<210> SEQ ID NO 15
<211> LENGTH: 110
<212> TYPE: DNA
<213> ORGANISM: Artificial Sequence
<220> FEATURE:
<223> OTHER INFORMATION: Description of Artificial Sequence: CDR
      grafting primer hR5Hv5A

<400> SEQUENCE: 15
agaagctagc tgaggagacg gtgaccaggg tgccttggcc ccagtagtcc atggcatagc      60
ccgagtctct tgcacagtaa tagaccgcag aatcctcatt tgtcaggctc              110

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Primer
      hR5HvPrS

<400> SEQUENCE: 16
```

```
ttctgtcgac ccaccatga                                                    19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer
      hR5HvPrA

<400> SEQUENCE: 17
agaagctagc tgaggagac                                                    19

<210> SEQ ID NO 18
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "a" of humanized H
      chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 18 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
 15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
             50                  55                  60 ccg aaa ttc cag ggc agg gcc aaa ctg act gca gcc aca tcc gcc agt     288
Pro Lys Phe Gln Gly Arg Ala Lys Leu Thr Ala Ala Thr Ser Ala Ser
         65                  70                  75 att gcc tac ttg gag ttc tcg agc ctg aca aat gag gat tct gcg gtc     336
Ile Ala Tyr Leu Glu Phe Ser Ser Leu Thr Asn Glu Asp Ser Ala Val
     80                  85                  90 tat tac tgt gca aga gac tcg ggc tat gcc atg gac tac tgg ggc caa     384
Tyr Tyr Cys Ala Arg Asp Ser Gly Tyr Ala Met Asp Tyr Trp Gly Gln
 95                 100                 105 ggc acc ctg gtc acc gtc tcc tca gct agc                             414
Gly Thr Leu Val Thr Val Ser Ser Ala Ser
110                 115

<210> SEQ ID NO 19
<211> LENGTH: 138
<212> TYPE: PRT
<213> ORGANISM: Artificial Sequence
<220> FEATURE:
<223> OTHER INFORMATION: Description of Artificial Sequence: Amino acid
``` sequence of version "a" of humanized H chain V
region

<400> SEQUENCE: 19

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
     -1   1                5                   10

Pro Gly Thr Ser Val Lys Ile Ser Cys Lys Ala Ser Gly Phe Asn Ile
         15                  20                  25

Lys Asp Tyr Tyr Met His Trp Val Lys Gln Arg Pro Gly Gln Gly Leu
 30              35                  40                  45

Glu Trp Ile Gly Gly Asn Asp Pro Ala Asn Gly His Ser Met Tyr Asp
                 50                  55                  60

Pro Lys Phe Gln Gly Arg Ala Lys Leu Thr Ala Ala Thr Ser Ala Ser
         65                  70                  75

Ile Ala Tyr Leu Glu Phe Ser Ser Leu Thr Asn Glu Asp Ser Ala Val
         80                  85                  90

Tyr Tyr Cys Ala Arg Asp Ser Gly Tyr Ala Met Asp Tyr Trp Gly Gln
         95                 100                 105

Gly Thr Leu Val Thr Val Ser Ser Ala Ser
110                 115

<210> SEQ ID NO 20
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3RFFS

<400> SEQUENCE: 20
ttcttggcca tagtatgtat gacccgaaat tccagggccg agtcacaatc actgcagaca      60
catccacgaa cacagcctac atggagctct cgagtctgag                          100

<210> SEQ ID NO 21
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3RFBS

<400> SEQUENCE: 21
ggagctctcg agtctgagat ctgaggacac agccatttat tactgtgcaa gagactcggg      60
ctatgccatg gttct                                                      75

<210> SEQ ID NO 22
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3RFFA

<400> SEQUENCE: 22
ctcagactcg agagctccat gtaggctgtg ttcgtggatg tgtctgcagt gattgtgact      60
cggccctgga atttcgggtc atacatacta tggccaagaa                          100

<210> SEQ ID NO 23
<211> LENGTH: 75

```
<212> TYPE: DNA
<213> ORGANISM: Artificial Sequence
<220> FEATURE:
<223> OTHER INFORMATION: Description of Artificial Sequence: FR
      shuffling primer F3RFBA

<400> SEQUENCE: 23
agaaccatgg catagcccga gtctcttgca cagtaataaa tggctgtgtc ctcagatctc    60
agactcgaga gctcc                                                    75

<210> SEQ ID NO 24
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3NMFS

<400> SEQUENCE: 24
ttcttggcca tagtatgtat gacccgaaat tccagggccg agtcacaatg ctggtagaca    60
catccaagaa ccagttctcc ctgaggctct cgagtgtgac                        100

<210> SEQ ID NO 25
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3NMBS

<400> SEQUENCE: 25
gaggctctcg agtgtgacag ccgcggacac agccgtatat tactgtgcaa gagactcggg    60
ctatgccatg gttct                                                    75

<210> SEQ ID NO 26
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3NMFA

<400> SEQUENCE: 26
gtcacactcg agagcctcag ggagaactgg ttcttggatg tgtctaccag cattgtgact    60
cggccctgga atttcgggtc atacatacta tggccaagaa                        100

<210> SEQ ID NO 27
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3NMBA

<400> SEQUENCE: 27
agaaccatgg catagcccga gtctcttgca cagtaatata cggctgtgtc cgcggctgtc    60
acactcgaga gcctc                                                    75

<210> SEQ ID NO 28
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "b" of humanized H
```

```
                 chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 28 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
         15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc cga gtc aca atc act gca gac aca tcc acg aac     288
Pro Lys Phe Gln Gly Arg Val Thr Ile Thr Ala Asp Thr Ser Thr Asn
             65                  70                  75 aca gcc tac atg gag ctc tcg agt ctg aga tct gag gac aca gcc att     336
Thr Ala Tyr Met Glu Leu Ser Ser Leu Arg Ser Glu Asp Thr Ala Ile
             80                  85                  90 tat tac tgt gca aga gac tcg ggc tat gcc atg gac tac tgg ggc caa     384
Tyr Tyr Cys Ala Arg Asp Ser Gly Tyr Ala Met Asp Tyr Trp Gly Gln
         95                 100                 105 ggc acc ctg gtc acc gtc tcc tca gct agc                             414
Gly Thr Leu Val Thr Val Ser Ser Ala Ser
110             115

<210> SEQ ID NO 29
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "b" of humanized H chain V
      region

<400> SEQUENCE: 29

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
         15                  20                  25

Lys Asp Tyr Tyr Met His Trp Val Lys Gln Arg Pro Gly Gln Gly Leu
 30                  35                  40                  45

Glu Trp Ile Gly Gly Asn Asp Pro Ala Asn Gly His Ser Met Tyr Asp
                 50                  55                  60

Pro Lys Phe Gln Gly Arg Val Thr Ile Thr Ala Asp Thr Ser Thr Asn
             65                  70                  75

Thr Ala Tyr Met Glu Leu Ser Ser Leu Arg Ser Glu Asp Thr Ala Ile
```

```
                    80                  85                  90
Tyr Tyr Cys Ala Arg Asp Ser Gly Tyr Ala Met Asp Tyr Trp Gly Gln
                95                 100                 105

Gly Thr Leu Val Thr Val Ser Ser Ala Ser
110                 115

<210> SEQ ID NO 30
<211> LENGTH: 414
<212> TYPE: DNA
<213> ORGANISM: Artificial Sequence
<220> FEATURE:
<223> OTHER INFORMATION: Description of Artificial Sequence: Nucleotide
      sequence coding for version "c" of humanized H
      chain V region
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 30 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1   1               5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
         15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
     30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc cga gtc aca atg ctg gta gac aca tcc aag aac     288
Pro Lys Phe Gln Gly Arg Val Thr Met Leu Val Asp Thr Ser Lys Asn
             65                  70                  75 cag ttc tcc ctg agg ctc tcg agt gtg aca gcc gcg gac aca gcc gta     336
Gln Phe Ser Leu Arg Leu Ser Ser Val Thr Ala Ala Asp Thr Ala Val
         80                  85                  90 tat tac tgt gca aga gac tcg ggc tat gcc atg gac tac tgg ggc caa     384
Tyr Tyr Cys Ala Arg Asp Ser Gly Tyr Ala Met Asp Tyr Trp Gly Gln
     95                 100                 105 ggc acc ctg gtc acc gtc tcc tca gct agc                             414
Gly Thr Leu Val Thr Val Ser Ser Ala Ser
110                 115

<210> SEQ ID NO 31
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "c" of humanized H chain V
      region

<400> SEQUENCE: 31

Met Lys Cys Ser Trp Val Ile Phe Phe Leu Met Ala Val Val Thr Gly
            -15                 -10                  -5
```

-continued

```
Val Asn Ser Gln Val Gln Leu Leu Glu Ser Gly Ala Val Leu Ala Arg
    -1   1                5                  10
Pro Gly Thr Ser Val Lys Ile Ser Cys Lys Ala Ser Gly Phe Asn Ile
         15                  20                  25
Lys Asp Tyr Tyr Met His Trp Val Lys Gln Arg Pro Gly Gln Gly Leu
 30              35                  40                  45
Glu Trp Ile Gly Gly Asn Asp Pro Ala Asn Gly His Ser Met Tyr Asp
                 50                  55                  60
Pro Lys Phe Gln Gly Arg Val Thr Met Leu Val Asp Thr Ser Lys Asn
                 65                  70                  75
Gln Phe Ser Leu Arg Leu Ser Ser Val Thr Ala Ala Asp Thr Ala Val
             80                  85                  90
Tyr Tyr Cys Ala Arg Asp Ser Gly Tyr Ala Met Asp Tyr Trp Gly Gln
         95                 100                 105
Gly Thr Leu Val Thr Val Ser Ser Ala Ser
110             115
```

<210> SEQ ID NO 32
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3EPS

<400> SEQUENCE: 32
ttcttggcca tagtatgtat gacccgaaat tccagggcag agtcacgatt actgcggacg    60
aatccacgag cacagcctac atggagctct cgagtctgag                         100

<210> SEQ ID NO 33
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3EPA

<400> SEQUENCE: 33
agaaccatgg catagcccga gtctctcgca cagaaatata cggccgagtc ctcagatctc    60
agactcgaga gctcc                                                    75

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer
      F3PrS

<400> SEQUENCE: 34
ttcttggcca tagtatgtat                                                20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Primer
      F3PrA

<400> SEQUENCE: 35
agaaccatgg catagccc                                                  18

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3VHS

<400> SEQUENCE: 36
ttcttggcca tagtatgtat gacccgaaat tccagggcag agtctcgatt accgcggacg    60
agtcaacgaa gatagcctac atggagctca acagtctgag                         100

<210> SEQ ID NO 37
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3VHA

<400> SEQUENCE: 37
agaaccatgg catagcccga gtctctcgca cagaaataaa cggccgtgtc ctcagatctc    60
agactgttga gctcc                                                    75

<210> SEQ ID NO 38
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "d" of humanized H
      chain V region

<400> SEQUENCE: 38 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1   1               5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
 15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc aga gtc acg att act gcg gac gaa tcc acg agc     288
Pro Lys Phe Gln Gly Arg Val Thr Ile Thr Ala Asp Glu Ser Thr Ser
             65                  70                  75 aca gcc tac atg gag ctc tcg agt ctg aga tct gag gac tcg gcc gta     336
Thr Ala Tyr Met Glu Leu Ser Ser Leu Arg Ser Glu Asp Ser Ala Val
         80                  85                  90 tat ttc tgt gcg aga gac tcg ggc tat gcc atg gac tac tgg ggc caa     384

```
Tyr Phe Cys Ala Arg Asp Ser Gly Tyr Ala Met Asp Tyr Trp Gly Gln
         95                 100                 105 ggc acc ctg gtc acc gtc tcc tca gct agc                              414
Gly Thr Leu Val Thr Val Ser Ser Ala Ser
110                 115
```

<210> SEQ ID NO 39
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "d" of humanized H chain V
      region

<400> SEQUENCE: 39

```
Met Lys Cys Ser Trp Val Ile Phe Phe Leu Met Ala Val Val Thr Gly
             -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
         15                  20                  25

Lys Asp Tyr Tyr Met His Trp Val Lys Gln Arg Pro Gly Gln Gly Leu
 30                  35                  40                  45

Glu Trp Ile Gly Gly Asn Asp Pro Ala Asn Gly His Ser Met Tyr Asp
                 50                  55                  60

Pro Lys Phe Gln Gly Arg Val Thr Ile Thr Ala Asp Glu Ser Thr Ser
             65                  70                  75

Thr Ala Tyr Met Glu Leu Ser Ser Leu Arg Ser Glu Asp Ser Ala Val
         80                  85                  90

Tyr Phe Cys Ala Arg Asp Ser Gly Tyr Ala Met Asp Tyr Trp Gly Gln
         95                 100                 105

Gly Thr Leu Val Thr Val Ser Ser Ala Ser
110                 115
```

<210> SEQ ID NO 40
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "e" of humanized H
      chain V region

<400> SEQUENCE: 40

```
atg aaa tgc agc tgg gtc atc ttc ttc ctg atg gca gtg gtt aca ggg     48
Met Lys Cys Ser Trp Val Ile Phe Phe Leu Met Ala Val Val Thr Gly
             -15                 -10                  -5 gtt aac tca cag gtg cag ctg ttg gag tct gga gct gtg ctg gca agg     96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att    144
Pro Gly Thr Ser Val Lys Ile Ser Cys Lys Ala Ser Gly Phe Asn Ile
         15                  20                  25 aaa gac tac tat atg cat tgg gta aaa cag agg cct gga cag ggt cta    192
```

```
Lys Asp Tyr Tyr Met His Trp Val Lys Gln Arg Pro Gly Gln Gly Leu
 30              35                  40                  45 gaa tgg att ggt ggg aat gat cct gcg aat ggc cat agt atg tat gac    240
Glu Trp Ile Gly Gly Asn Asp Pro Ala Asn Gly His Ser Met Tyr Asp
             50                  55                  60 ccg aaa ttc cag ggc aga gtc tcg att acc gcg gac gag tca acg aag    288
Pro Lys Phe Gln Gly Arg Val Ser Ile Thr Ala Asp Glu Ser Thr Lys
             65                  70                  75 ata gcc tac atg gag ctc aac agt ctg aga tct gag gac acg gcc gtt    336
Ile Ala Tyr Met Glu Leu Asn Ser Leu Arg Ser Glu Asp Thr Ala Val
             80                  85                  90 tat ttc tgt gcg aga gac tcg ggc tat gcc atg gac tac tgg ggc caa    384
Tyr Phe Cys Ala Arg Asp Ser Gly Tyr Ala Met Asp Tyr Trp Gly Gln
             95                 100                 105 ggc acc ctg gtc acc gtc tcc tca gct agc                            414
Gly Thr Leu Val Thr Val Ser Ser Ala Ser
110                 115
```

<210> SEQ ID NO 41
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "e" of humanized H chain V
      region

<400> SEQUENCE: 41

```
Met Lys Cys Ser Trp Val Ile Phe Phe Leu Met Ala Val Val Thr Gly
                -15                 -10                  -5

Val Asn Ser Gln Val Gln Leu Leu Glu Ser Gly Ala Val Leu Ala Arg
         -1  1               5                  10

Pro Gly Thr Ser Val Lys Ile Ser Cys Lys Ala Ser Gly Phe Asn Ile
             15                  20                  25

Lys Asp Tyr Tyr Met His Trp Val Lys Gln Arg Pro Gly Gln Gly Leu
 30              35                  40                  45

Glu Trp Ile Gly Gly Asn Asp Pro Ala Asn Gly His Ser Met Tyr Asp
             50                  55                  60

Pro Lys Phe Gln Gly Arg Val Ser Ile Thr Ala Asp Glu Ser Thr Lys
             65                  70                  75

Ile Ala Tyr Met Glu Leu Asn Ser Leu Arg Ser Glu Asp Thr Ala Val
             80                  85                  90

Tyr Phe Cys Ala Arg Asp Ser Gly Tyr Ala Met Asp Tyr Trp Gly Gln
             95                 100                 105

Gly Thr Leu Val Thr Val Ser Ser Ala Ser
110                 115
```

<210> SEQ ID NO 42
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3SSS

<400> SEQUENCE: 42
ttcttggcca tagtatgtat gacccgaaat tccagggcag agtcacgatt accgcggaca    60
catccacgag cacagcctac atggagctca ggagcctgag                         100

<210> SEQ ID NO 43
<211> LENGTH: 75

```
<212> TYPE: DNA
<213> ORGANISM: Artificial Sequence
<220> FEATURE:
<223> OTHER INFORMATION: Description of Artificial Sequence: FR
      shuffling primer F3SSA

<400> SEQUENCE: 43
agaaccatgg catagcccga gtctctcgca cagtaataca cggccgtgtc gtcagatctc    60
aggctcctga gctcc                                                     75

<210> SEQ ID NO 44
<211> LENGTH: 100
<212> TYPE: DNA
<213> ORGANISM: Artificial Sequence
<220> FEATURE:
<223> OTHER INFORMATION: Description of Artificial Sequence: FR
      shuffling primer F3CDS

<400> SEQUENCE: 44
ttcttggcca tagtatgtat gacccgaaat tccagggcaa agccactctg actgcagacg    60
aatcctccag cacagcctac atgcaactct cgagcctacg                         100

<210> SEQ ID NO 45
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3CDA

<400> SEQUENCE: 45
agaaccatgg catagcccga gtctcttgca caagaataga ccgcagagtc ctcagatcgt    60
aggctcgaga gttgc                                                     75

<210> SEQ ID NO 46
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "f" of humanized H
      chain V region

<400> SEQUENCE: 46 atg aaa tgc agc tgg gtc atc ttc ttc ctg atg gca gtg gtt aca ggg    48
Met Lys Cys Ser Trp Val Ile Phe Phe Leu Met Ala Val Val Thr Gly
        -15                 -10                  -5 gtt aac tca cag gtg cag ctg ttg gag tct gga gct gtg ctg gca agg    96
Val Asn Ser Gln Val Gln Leu Leu Glu Ser Gly Ala Val Leu Ala Arg
     -1  1               5                  10 cct ggg act tcc gtg aag atc tcc tgc aag gct tcc gga ttc aac att   144
Pro Gly Thr Ser Val Lys Ile Ser Cys Lys Ala Ser Gly Phe Asn Ile
     15                  20                  25 aaa gac tac tat atg cat tgg gta aaa cag agg cct gga cag ggt cta   192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac   240
Glu Trp Ile Gly Gly Asn Asp Pro Ala Asn Gly His Ser Met Tyr Asp
```

```
Glu Trp Ile Gly Gly Asn Asp Pro Ala Asn Gly His Ser Met Tyr Asp
            50                  55                  60 ccg aaa ttc cag ggc aga gtc acg att acc gcg gac aca tcc acg agc      288
Pro Lys Phe Gln Gly Arg Val Thr Ile Thr Ala Asp Thr Ser Thr Ser
            65                  70                  75 aca gcc tac atg gag ctc agg agc ctg aga tct gac gac acg gcc gtg      336
Thr Ala Tyr Met Glu Leu Arg Ser Leu Arg Ser Asp Asp Thr Ala Val
            80                  85                  90 tat tac tgt gcg aga gac tcg ggc tat gcc atg gac tac tgg ggc caa      384
Tyr Tyr Cys Ala Arg Asp Ser Gly Tyr Ala Met Asp Tyr Trp Gly Gln
            95                  100                 105 ggc acc ctg gtc acc gtc tcc tca gct agc                              414
Gly Thr Leu Val Thr Val Ser Ser Ala Ser
110                 115
```

<210> SEQ ID NO 47
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "f" of humanized H chain V
      region

<400> SEQUENCE: 47

```
Met Lys Cys Ser Trp Val Ile Phe Phe Leu Met Ala Val Val Thr Gly
                -15                 -10                 -5

Val Asn Ser Gln Val Gln Leu Leu Glu Ser Gly Ala Val Leu Ala Arg
        -1  1               5                   10

Pro Gly Thr Ser Val Lys Ile Ser Cys Lys Ala Ser Gly Phe Asn Ile
            15                  20                  25

Lys Asp Tyr Tyr Met His Trp Val Lys Gln Arg Pro Gly Gln Gly Leu
            30                  35                  40              45

Glu Trp Ile Gly Gly Asn Asp Pro Ala Asn Gly His Ser Met Tyr Asp
                50                  55                  60

Pro Lys Phe Gln Gly Arg Val Thr Ile Thr Ala Asp Thr Ser Thr Ser
            65                  70                  75

Thr Ala Tyr Met Glu Leu Arg Ser Leu Arg Ser Asp Asp Thr Ala Val
            80                  85                  90

Tyr Tyr Cys Ala Arg Asp Ser Gly Tyr Ala Met Asp Tyr Trp Gly Gln
            95                  100                 105

Gly Thr Leu Val Thr Val Ser Ser Ala Ser
110                 115
```

<210> SEQ ID NO 48
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "g" of humanized H
      chain V region

<400> SEQUENCE: 48

```
atg aaa tgc agc tgg gtc atc ttc ttc ctg atg gca gtg gtt aca ggg       48
```

```
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
        15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
30                  35                  40                  45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                50                  55                  60 ccg aaa ttc cag ggc aaa gcc act ctg act gca gac gaa tcc tcc agc     288
Pro Lys Phe Gln Gly Lys Ala Thr Leu Thr Ala Asp Glu Ser Ser Ser
            65                  70                  75 aca gcc tac atg caa ctc tcg agc cta cga tct gag gac tct gcg gtc     336
Thr Ala Tyr Met Gln Leu Ser Ser Leu Arg Ser Glu Asp Ser Ala Val
        80                  85                  90 tat tct tgt gca aga gac tcg ggc tat gcc atg gac tac tgg ggc caa     384
Tyr Ser Cys Ala Arg Asp Ser Gly Tyr Ala Met Asp Tyr Trp Gly Gln
    95                 100                 105 ggc acc ctg gtc acc gtc tcc tca gct agc                             414
Gly Thr Leu Val Thr Val Ser Ser Ala Ser
110                 115

<210> SEQ ID NO 49
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "g" of humanized H chain V
      region

<400> SEQUENCE: 49

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
        15                  20                  25

Lys Asp Tyr Tyr Met His Trp Val Lys Gln Arg Pro Gly Gln Gly Leu
30                  35                  40                  45

Glu Trp Ile Gly Gly Asn Asp Pro Ala Asn Gly His Ser Met Tyr Asp
                50                  55                  60

Pro Lys Phe Gln Gly Lys Ala Thr Leu Thr Ala Asp Glu Ser Ser Ser
            65                  70                  75

Thr Ala Tyr Met Gln Leu Ser Ser Leu Arg Ser Glu Asp Ser Ala Val
        80                  85                  90

Tyr Ser Cys Ala Arg Asp Ser Gly Tyr Ala Met Asp Tyr Trp Gly Gln
    95                 100                 105

Gly Thr Leu Val Thr Val Ser Ser Ala Ser
110                 115

<210> SEQ ID NO 50
<211> LENGTH: 100
<212> TYPE: DNA
<213> ORGANISM: Artificial Sequence
<220> FEATURE:
```

-continued

```
<223> OTHER INFORMATION: Description of Artificial Sequence: FR
      shuffling primer F3ADS

<400> SEQUENCE: 50
ttcttggcca tagtatgtat gacccgaaat tccagggccg cgtcaccatg tcagccgaca      60
agtcctccag cgccgcctat ttacagtgga ccagccttaa                           100

<210> SEQ ID NO 51
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3ADA

<400> SEQUENCE: 51
agaaccatgg catagcccga gtctctcgcg cagaaatata tggcggtgtc cgaggcctta      60
aggctggtcc actgt                                                      75

<210> SEQ ID NO 52
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "h" of humanized H
      chain V region

<400> SEQUENCE: 52 atg aaa tgc agc tgg gtc atc ttc ttc ctg atg gca gtg gtt aca ggg       48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg       96
Val Asn Ser Gln Val Gln Leu Leu Glu Ser Gly Ala Val Leu Ala Arg
     -1   1               5                  10 cct ggg act tcc gtg aag atc tcc tgc aag gct tcc gga ttc aac att      144
Pro Gly Thr Ser Val Lys Ile Ser Cys Lys Ala Ser Gly Phe Asn Ile
 15                  20                  25 aaa gac tac tat atg cat tgg gta aaa cag agg cct gga cag ggt cta      192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac      240
Glu Trp Ile Gly Gly Asn Asp Pro Ala Asn Gly His Ser Met Tyr Asp
                 50                  55                  60 ccg aaa ttc cag ggc cgc gtc acc atg tca gcc gac aag tcc tcc agc      288
Pro Lys Phe Gln Gly Arg Val Thr Met Ser Ala Asp Lys Ser Ser Ser
             65                  70                  75 gcc gcc tat tta cag tgg acc agc ctt aag gct tcg gac acc gcc ata      336
Ala Ala Tyr Leu Gln Trp Thr Ser Leu Lys Ala Ser Asp Thr Ala Ile
         80                  85                  90 tat ttc tgc gcg aga gac tcg ggc tat gcc atg gac tac tgg ggc caa      384
Tyr Phe Cys Ala Arg Asp Ser Gly Tyr Ala Met Asp Tyr Trp Gly Gln
     95                 100                 105 ggc acc ctg gtc acc gtc tcc tca gct agc                              414
Gly Thr Leu Val Thr Val Ser Ser Ala Ser
110                 115
```

<210> SEQ ID NO 53
<211> LENGTH: 138
<212> TYPE: PRT
<213> ORGANISM: Artificial Sequence
<220> FEATURE:
<223> OTHER INFORMATION: Description of Artificial Sequence: Amino acid
sequence of version "h" of humanized H chain V
region

<400> SEQUENCE: 53

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
         15                  20                  25

Lys Asp Tyr Tyr Met His Trp Val Lys Gln Arg Pro Gly Gln Gly Leu
     30                  35                  40                  45

Glu Trp Ile Gly Gly Asn Asp Pro Ala Asn Gly His Ser Met Tyr Asp
                 50                  55                  60

Pro Lys Phe Gln Gly Arg Val Thr Met Ser Ala Asp Lys Ser Ser Ser
             65                  70                  75

Ala Ala Tyr Leu Gln Trp Thr Ser Leu Lys Ala Ser Asp Thr Ala Ile
         80                  85                  90

Tyr Phe Cys Ala Arg Asp Ser Gly Tyr Ala Met Asp Tyr Trp Gly Gln
     95                 100                 105

Gly Thr Leu Val Thr Val Ser Ser Ala Ser
110                 115

<210> SEQ ID NO 54
<211> LENGTH: 100
<212> TYPE: DNA
<213> ORGANISM: Artificial Sequence
<220> FEATURE:
<223> OTHER INFORMATION: Description of Artificial Sequence: FR
shuffling primer F3MMS

<400> SEQUENCE: 54
ttcttggcca tagtatgtat gacccgaaat tccagggcag agtcacgatt accgcggaca       60
catcgacgag cacagtcttc atggaactga gcagcctgag                           100

<210> SEQ ID NO 55
<211> LENGTH: 75
<212> TYPE: DNA
<213> ORGANISM: Artificial Sequence
<220> FEATURE:
<223> OTHER INFORMATION: Description of Artificial Sequence: FR
shuffling primer F3MMA

<400> SEQUENCE: 55
agaaccatgg catagcccga gtctctcgca cagtaataca cggccgtgtc ttcagatctc       60
aggctgctca gttcc                                                       75

<210> SEQ ID NO 56
<211> LENGTH: 100
<212> TYPE: DNA
<213> ORGANISM: Artificial Sequence
<220> FEATURE:
<223> OTHER INFORMATION: Description of Artificial Sequence: FR
shuffling primer F3BMS

<400> SEQUENCE: 56

```
ttcttggcca tagtatgtat gacccgaaat tccagggcag agtcaccttt accgcggaca    60
catccgcgaa cacagcctac atggagttga ggagcctcag                         100
```

<210> SEQ ID NO 57
<211> LENGTH: 75
<212> TYPE: DNA
<213> ORGANISM: Artificial Sequence
<220> FEATURE:
<223> OTHER INFORMATION: Description of Artificial Sequence: FR
      shuffling primer F3BMA

<400> SEQUENCE: 57

```
agaaccatgg catagcccga gtctctcgca caataataaa cagccgtgtc tgcagatctg    60
aggctcctca actcc                                                     75
```

<210> SEQ ID NO 58
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "i" of humanized H
      chain V region

<400> SEQUENCE: 58

```
atg aaa tgc agc tgg gtc atc ttc ttc ctg atg gca gtg gtt aca ggg     48
Met Lys Cys Ser Trp Val Ile Phe Phe Leu Met Ala Val Val Thr Gly
        -15                 -10                  -5 gtt aac tca cag gtg cag ctg ttg gag tct gga gct gtg ctg gca agg     96
Val Asn Ser Gln Val Gln Leu Leu Glu Ser Gly Ala Val Leu Ala Arg
 -1   1               5                  10 cct ggg act tcc gtg aag atc tcc tgc aag gct tcc gga ttc aac att    144
Pro Gly Thr Ser Val Lys Ile Ser Cys Lys Ala Ser Gly Phe Asn Ile
 15                  20                  25 aaa gac tac tat atg cat tgg gta aaa cag agg cct gga cag ggt cta    192
Lys Asp Tyr Tyr Met His Trp Val Lys Gln Arg Pro Gly Gln Gly Leu
 30                  35                  40                  45 gaa tgg att ggt ggg aat gat cct gcg aat ggc cat agt atg tat gac    240
Glu Trp Ile Gly Gly Asn Asp Pro Ala Asn Gly His Ser Met Tyr Asp
             50                  55                  60 ccg aaa ttc cag ggc aga gtc acg att acc gcg gac aca tcg acg agc    288
Pro Lys Phe Gln Gly Arg Val Thr Ile Thr Ala Asp Thr Ser Thr Ser
         65                  70                  75 aca gtc ttc atg gaa ctg agc agc ctg aga tct gaa gac acg gcc gtg    336
Thr Val Phe Met Glu Leu Ser Ser Leu Arg Ser Glu Asp Thr Ala Val
             80                  85                  90 tat tac tgt gcg aga gac tcg ggc tat gcc atg gac tac tgg ggc caa    384
Tyr Tyr Cys Ala Arg Asp Ser Gly Tyr Ala Met Asp Tyr Trp Gly Gln
 95                 100                 105 ggc acc ctg gtc acc gtc tcc tca gct agc                            414
Gly Thr Leu Val Thr Val Ser Ser Ala Ser
110                 115
```

<210> SEQ ID NO 59
<211> LENGTH: 138

<212> TYPE: PRT
<213> ORGANISM: Artificial Sequence
<220> FEATURE:
<223> OTHER INFORMATION: Description of Artificial Sequence: Amino acid
      sequence of version "i" of humanized H chain V
      region

<400> SEQUENCE: 59

```
Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
     -1   1               5                   10

Pro Gly Thr Ser Val Lys Ile Ser Cys Lys Ala Ser Gly Phe Asn Ile
         15                  20                  25

Lys Asp Tyr Tyr Met His Trp Val Lys Gln Arg Pro Gly Gln Gly Leu
 30              35                  40                      45

Glu Trp Ile Gly Gly Asn Asp Pro Ala Asn Gly His Ser Met Tyr Asp
                 50                  55                  60

Pro Lys Phe Gln Gly Arg Val Thr Ile Thr Ala Asp Thr Ser Thr Ser
             65                  70                  75

Thr Val Phe Met Glu Leu Ser Ser Leu Arg Ser Glu Asp Thr Ala Val
         80                  85                  90

Tyr Tyr Cys Ala Arg Asp Ser Gly Tyr Ala Met Asp Tyr Trp Gly Gln
 95                  100                 105

Gly Thr Leu Val Thr Val Ser Ser Ala Ser
110                 115
```

<210> SEQ ID NO 60
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "j" of humanized H
      chain V region

<400> SEQUENCE: 60

```
atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1   1               5                   10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
         15                  20                  25 aaa gac tac tat atg cat tgg gta aaa cag agg cct gga cag ggt cta     192
Lys Asp Tyr Tyr Met His Trp Val Lys Gln Arg Pro Gly Gln Gly Leu
 30              35                  40                      45 gaa tgg att ggt ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc aga gtc acc ttt acc gcg gac aca tcc gcg aac     288
Pro Lys Phe Gln Gly Arg Val Thr Phe Thr Ala Asp Thr Ser Ala Asn
             65                  70                  75
```

```
aca gcc tac atg gag ttg agg agc ctc aga tct gca gac acg gct gtt    336
Thr Ala Tyr Met Glu Leu Arg Ser Leu Arg Ser Ala Asp Thr Ala Val
        80                  85                  90 tat tat tgt gcg aga gac tcg ggc tat gcc atg gac tac tgg ggc caa    384
Tyr Tyr Cys Ala Arg Asp Ser Gly Tyr Ala Met Asp Tyr Trp Gly Gln
        95                  100                 105 ggc acc ctg gtc acc gtc tcc tca gct agc                            414
Gly Thr Leu Val Thr Val Ser Ser Ala Ser
110                 115

<210> SEQ ID NO 61
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "j" of humanized H chain V
      region

<400> SEQUENCE: 61

Met Lys Cys Ser Trp Val Ile Phe Phe Leu Met Ala Val Val Thr Gly
                -15                 -10                 -5

Val Asn Ser Gln Val Gln Leu Leu Glu Ser Gly Ala Val Leu Ala Arg
        -1  1               5                   10

Pro Gly Thr Ser Val Lys Ile Ser Cys Lys Ala Ser Gly Phe Asn Ile
        15                  20                  25

Lys Asp Tyr Tyr Met His Trp Val Lys Gln Arg Pro Gly Gln Gly Leu
    30                  35                  40                  45

Glu Trp Ile Gly Gly Asn Asp Pro Ala Asn Gly His Ser Met Tyr Asp
                50                  55                  60

Pro Lys Phe Gln Gly Arg Val Thr Phe Thr Ala Asp Thr Ser Ala Asn
            65                  70                  75

Thr Ala Tyr Met Glu Leu Arg Ser Leu Arg Ser Ala Asp Thr Ala Val
        80                  85                  90

Tyr Tyr Cys Ala Arg Asp Ser Gly Tyr Ala Met Asp Tyr Trp Gly Gln
        95                  100                 105

Gly Thr Leu Val Thr Val Ser Ser Ala Ser
110                 115

<210> SEQ ID NO 62
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2MPS

<400> SEQUENCE: 62
ttctatgcat tgggtgcgcc aggctccagg acagggcctg gagtggatgg gagggaatga    60
tcctgcgaat ggccattct                                                 79

<210> SEQ ID NO 63
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2MPA

<400> SEQUENCE: 63
agaatggcca ttcgcaggat cattccctcc catccactcc aggccctgtc ctggagcctg    60
```
gcgcacccaa tgcatagaa                                                79

<210> SEQ ID NO 64
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "b1" of humanized H
      chain V region

<400> SEQUENCE: 64 atg aaa tgc agc tgg gtc atc ttc ttc ctg atg gca gtg gtt aca ggg        48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg        96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att       144
Pro Gly Thr Ser Val Lys Ile Ser Cys Lys Ala Ser Gly Phe Asn Ile
     15                  20                  25 aaa gac tac tat atg cat tgg gtg cgc cag gct cca gga cag ggc ctg       192
Lys Asp Tyr Tyr Met His Trp Val Arg Gln Ala Pro Gly Gln Gly Leu
 30                  35                  40                  45 gag tgg atg gga ggg aat gat cct gcg aat ggc cat agt atg tat gac       240
Glu Trp Met Gly Gly Asn Asp Pro Ala Asn Gly His Ser Met Tyr Asp
                 50                  55                  60 ccg aaa ttc cag ggc cga gtc aca atc act gca gac aca tcc acg aac       288
Pro Lys Phe Gln Gly Arg Val Thr Ile Thr Ala Asp Thr Ser Thr Asn
             65                  70                  75 aca gcc tac atg gag ctc tcg agt ctg aga tct gag gac aca gcc att       336
Thr Ala Tyr Met Glu Leu Ser Ser Leu Arg Ser Glu Asp Thr Ala Ile
         80                  85                  90 tat tac tgt gca aga gac tcg ggc tat gcc atg gac tac tgg ggc caa       384
Tyr Tyr Cys Ala Arg Asp Ser Gly Tyr Ala Met Asp Tyr Trp Gly Gln
 95                 100                 105 ggc acc ctg gtc acc gtc tcc tca gct agc                                414
Gly Thr Leu Val Thr Val Ser Ser Ala Ser
110                 115

<210> SEQ ID NO 65
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "b1" of humanized H chain V
      region

<400> SEQUENCE: 65

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
         -1   1               5                  10

Pro Gly Thr Ser Val Lys Ile Ser Cys Lys Ala Ser Gly Phe Asn Ile
     15                  20                  25

```
Lys Asp Tyr Tyr Met His Trp Val Arg Gln Ala Pro Gly Gln Gly Leu
 30                  35                  40                  45

Glu Trp Met Gly Gly Asn Asp Pro Ala Asn Gly His Ser Met Tyr Asp
             50                  55                  60

Pro Lys Phe Gln Gly Arg Val Thr Ile Thr Ala Asp Thr Ser Thr Asn
             65                  70                  75

Thr Ala Tyr Met Glu Leu Ser Ser Leu Arg Ser Glu Asp Thr Ala Ile
         80                  85                  90

Tyr Tyr Cys Ala Arg Asp Ser Gly Tyr Ala Met Asp Tyr Trp Gly Gln
     95                 100                 105

Gly Thr Leu Val Thr Val Ser Ser Ala Ser
110                 115

<210> SEQ ID NO 66
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
      sequence coding for version "d1" of humanized H
      chain V region

<400> SEQUENCE: 66 atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                  -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
         -1   1               5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
         15                  20                  25 aaa gac tac tat atg cat tgg gtg cgc cag gct cca gga cag ggc ctg     192
Lys Asp Tyr Tyr Met His Trp Val Arg Gln Ala Pro Gly Gln Gly Leu
 30                  35                  40                  45 gag tgg atg gga ggg aat gat cct gcg aat ggc cat agt atg tat gac     240
Glu Trp Met Gly Gly Asn Asp Pro Ala Asn Gly His Ser Met Tyr Asp
             50                  55                  60 ccg aaa ttc cag ggc aga gtc acg att act gcg gac gaa tcc acg agc     288
Pro Lys Phe Gln Gly Arg Val Thr Ile Thr Ala Asp Glu Ser Thr Ser
             65                  70                  75 aca gcc tac atg gag ctc tcg agt ctg aga tct gag gac tcg gcc gta     336
Thr Ala Tyr Met Glu Leu Ser Ser Leu Arg Ser Glu Asp Ser Ala Val
         80                  85                  90 tat ttc tgt gcg aga gac tcg ggc tat gcc atg gac tac tgg ggc caa     384
Tyr Phe Cys Ala Arg Asp Ser Gly Tyr Ala Met Asp Tyr Trp Gly Gln
     95                 100                 105 ggc acc ctg gtc acc gtc tcc tca gct agc                              414
Gly Thr Leu Val Thr Val Ser Ser Ala Ser
110                 115

<210> SEQ ID NO 67
<211> LENGTH: 138
<212> TYPE: PRT
<213> ORGANISM: Artificial Sequence
```

```
<220> FEATURE:
<223> OTHER INFORMATION: Description of Artificial Sequence: Amino acid
      sequence of version "d1" of humanized H chain V
      region

<400> SEQUENCE: 67

Met Lys Cys Ser Trp Val Ile Phe Phe Leu Met Ala Val Val Thr Gly
            -15                 -10                  -5

Val Asn Ser Gln Val Gln Leu Leu Glu Ser Gly Ala Val Leu Ala Arg
        -1   1               5                  10

Pro Gly Thr Ser Val Lys Ile Ser Cys Lys Ala Ser Gly Phe Asn Ile
            15                  20                  25

Lys Asp Tyr Tyr Met His Trp Val Arg Gln Ala Pro Gly Gln Gly Leu
    30              35                  40                  45

Glu Trp Met Gly Gly Asn Asp Pro Ala Asn Gly His Ser Met Tyr Asp
                50                  55                  60

Pro Lys Phe Gln Gly Arg Val Thr Ile Thr Ala Asp Glu Ser Thr Ser
            65                  70                  75

Thr Ala Tyr Met Glu Leu Ser Ser Leu Arg Ser Glu Asp Ser Ala Val
            80                  85                  90

Tyr Phe Cys Ala Arg Asp Ser Gly Tyr Ala Met Asp Tyr Trp Gly Gln
            95                  100                 105

Gly Thr Leu Val Thr Val Ser Ser Ala Ser
110                 115

<210> SEQ ID NO 68
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2VHS

<400> SEQUENCE: 68
ttctatgcat tgggtgcgac aggcccctgg acaagggctt gagtggattg gagggaatga    60
tcctgcgaat ggccatctt                                                 79

<210> SEQ ID NO 69
<211> LENGTH: 79
<212> TYPE: DNA
<213> ORGANISM: Artificial Sequence
<220> FEATURE:
<223> OTHER INFORMATION: Description of Artificial Sequence: FR
      shuffling primer F2VHA

<400> SEQUENCE: 69
aagatggcca ttcgcaggat cattccctcc aatccactca gcccttgtc cagggggcctg    60 tcgcacccaa tgcatagaa                                                 79

<210> SEQ ID NO 70
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
``` sequence coding for version "b3" of humanized H
chain V region

<400> SEQUENCE: 70

```
atg aaa tgc agc tgg gtc atc ttc ttc ctg atg gca gtg gtt aca ggg    48
Met Lys Cys Ser Trp Val Ile Phe Phe Leu Met Ala Val Val Thr Gly
            -15                 -10                 -5 gtt aac tca cag gtg cag ctg ttg gag tct gga gct gtg ctg gca agg    96
Val Asn Ser Gln Val Gln Leu Leu Glu Ser Gly Ala Val Leu Ala Arg
        -1   1               5                   10 cct ggg act tcc gtg aag atc tcc tgc aag gct tcc gga ttc aac att   144
Pro Gly Thr Ser Val Lys Ile Ser Cys Lys Ala Ser Gly Phe Asn Ile
     15                  20                  25 aaa gac tac tat atg cat tgg gtg cga cag gcc cct gga caa ggg ctt   192
Lys Asp Tyr Tyr Met His Trp Val Arg Gln Ala Pro Gly Gln Gly Leu
 30                  35                  40                  45 gag tgg att gga ggg aat gat cct gcg aat ggc cat agt atg tat gac   240
Glu Trp Ile Gly Gly Asn Asp Pro Ala Asn Gly His Ser Met Tyr Asp
                 50                  55                  60 ccg aaa ttc cag ggc cga gtc aca atc act gca gac aca tcc acg aac   288
Pro Lys Phe Gln Gly Arg Val Thr Ile Thr Ala Asp Thr Ser Thr Asn
             65                  70                  75 aca gcc tac atg gag ctc tcg agt ctg aga tct gag gac aca gcc att   336
Thr Ala Tyr Met Glu Leu Ser Ser Leu Arg Ser Glu Asp Thr Ala Ile
         80                  85                  90 tat tac tgt gca aga gac tcg ggc tat gcc atg gac tac tgg ggc caa   384
Tyr Tyr Cys Ala Arg Asp Ser Gly Tyr Ala Met Asp Tyr Trp Gly Gln
     95                 100                 105 ggc acc ctg gtc acc gtc tcc tca gct agc                           414
Gly Thr Leu Val Thr Val Ser Ser Ala Ser
110                 115
```

<210> SEQ ID NO 71
<211> LENGTH: 138
<212> TYPE: PRT
<213> ORGANISM: Artificial Sequence
<220> FEATURE:
<223> OTHER INFORMATION: Description of Artificial Sequence: Amino acid
      sequence of version "b3" of humanized H chain V
      region

<400> SEQUENCE: 71

```
Met Lys Cys Ser Trp Val Ile Phe Phe Leu Met Ala Val Val Thr Gly
            -15                 -10                 -5

Val Asn Ser Gln Val Gln Leu Leu Glu Ser Gly Ala Val Leu Ala Arg
        -1   1               5                   10

Pro Gly Thr Ser Val Lys Ile Ser Cys Lys Ala Ser Gly Phe Asn Ile
     15                  20                  25

Lys Asp Tyr Tyr Met His Trp Val Arg Gln Ala Pro Gly Gln Gly Leu
 30                  35                  40                  45

Glu Trp Ile Gly Gly Asn Asp Pro Ala Asn Gly His Ser Met Tyr Asp
                 50                  55                  60

Pro Lys Phe Gln Gly Arg Val Thr Ile Thr Ala Asp Thr Ser Thr Asn
             65                  70                  75

Thr Ala Tyr Met Glu Leu Ser Ser Leu Arg Ser Glu Asp Thr Ala Ile
         80                  85                  90

Tyr Tyr Cys Ala Arg Asp Ser Gly Tyr Ala Met Asp Tyr Trp Gly Gln
     95                 100                 105

Gly Thr Leu Val Thr Val Ser Ser Ala Ser
110                 115
```

<210> SEQ ID NO 72
<211> LENGTH: 414
<212> TYPE: DNA
<213> ORGANISM: Artificial Sequence
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)
<220> FEATURE:
<223> OTHER INFORMATION: Description of Artificial Sequence: Nucleotide
sequence coding for version "d3" of humanized H
chain V region

<400> SEQUENCE: 72

```
atg aaa tgc agc tgg gtc atc ttc ttc ctg atg gca gtg gtt aca ggg      48
Met Lys Cys Ser Trp Val Ile Phe Phe Leu Met Ala Val Val Thr Gly
            -15                 -10                 -5 gtt aac tca cag gtg cag ctg ttg gag tct gga gct gtg ctg gca agg      96
Val Asn Ser Gln Val Gln Leu Leu Glu Ser Gly Ala Val Leu Ala Arg
     -1  1                   5                  10 cct ggg act tcc gtg aag atc tcc tgc aag gct tcc gga ttc aac att     144
Pro Gly Thr Ser Val Lys Ile Ser Cys Lys Ala Ser Gly Phe Asn Ile
         15                  20                  25 aaa gac tac tat atg cat tgg gtg cga cag gcc cct gga caa ggg ctt     192
Lys Asp Tyr Tyr Met His Trp Val Arg Gln Ala Pro Gly Gln Gly Leu
 30                  35                  40                  45 gag tgg att gga ggg aat gat cct gcg aat ggc cat agt atg tat gac     240
Glu Trp Ile Gly Gly Asn Asp Pro Ala Asn Gly His Ser Met Tyr Asp
                 50                  55                  60 ccg aaa ttc cag ggc aga gtc acg att act gcg gac gaa tcc acg agc     288
Pro Lys Phe Gln Gly Arg Val Thr Ile Thr Ala Asp Glu Ser Thr Ser
             65                  70                  75 aca gcc tac atg gag ctc tcg agt ctg aga tct gag gac tcg gcc gta     336
Thr Ala Tyr Met Glu Leu Ser Ser Leu Arg Ser Glu Asp Ser Ala Val
         80                  85                  90 tat ttc tgt gcg aga gac tcg ggc tat gcc atg gac tac tgg ggc caa     384
Tyr Phe Cys Ala Arg Asp Ser Gly Tyr Ala Met Asp Tyr Trp Gly Gln
     95                 100                 105 ggc acc ctg gtc acc gtc tcc tca gct agc                             414
Gly Thr Leu Val Thr Val Ser Ser Ala Ser
110                 115
```

<210> SEQ ID NO 73
<211> LENGTH: 138
<212> TYPE: PRT
<213> ORGANISM: Artificial Sequence
<220> FEATURE:
<223> OTHER INFORMATION: Description of Artificial Sequence: Amino acid
sequence of version "d3" of humanized H chain V
region

<400> SEQUENCE: 73

```
Met Lys Cys Ser Trp Val Ile Phe Phe Leu Met Ala Val Val Thr Gly
            -15                 -10                 -5

Val Asn Ser Gln Val Gln Leu Leu Glu Ser Gly Ala Val Leu Ala Arg
     -1  1                   5                  10

Pro Gly Thr Ser Val Lys Ile Ser Cys Lys Ala Ser Gly Phe Asn Ile
         15                  20                  25

Lys Asp Tyr Tyr Met His Trp Val Arg Gln Ala Pro Gly Gln Gly Leu
 30                  35                  40                  45
```

-continued

```
Glu Trp Ile Gly Gly Asn Asp Pro Ala Asn Gly His Ser Met Tyr Asp
            50                  55                  60
Pro Lys Phe Gln Gly Arg Val Thr Ile Thr Ala Asp Glu Ser Thr Ser
        65                  70                  75
Thr Ala Tyr Met Glu Leu Ser Ser Leu Arg Ser Glu Asp Ser Ala Val
            80                  85                  90
Tyr Phe Cys Ala Arg Asp Ser Gly Tyr Ala Met Asp Tyr Trp Gly Gln
        95                  100                 105
Gly Thr Leu Val Thr Val Ser Ser Ala Ser
110                 115

<210> SEQ ID NO 74
<211> LENGTH: 98
<212> TYPE: DNA
<213> ORGANISM: Artificial Sequence
<220> FEATURE:
<223> OTHER INFORMATION: Description of Artificial Sequence: FR
      shuffling vector h5Lv1S

<400> SEQUENCE: 74
gtctagatct ccaccatgag ggcccctgct cagttttttg ggatcttgtt gctctggttt     60
ccagggatcc gatgtgacat ccagatgacc cagtctcc                            98

<210> SEQ ID NO 75
<211> LENGTH: 98
<212> TYPE: DNA
<213> ORGANISM: Artificial Sequence
<220> FEATURE:
<223> OTHER INFORMATION: Description of Artificial Sequence: FR
      shuffling vector h5Lv4S

<400> SEQUENCE: 75
ttggcagatg gggtcccatc aaggttcagt ggctccggat ctggtaccga tttcactctc     60
accatctcga gtctgcaacc tgaagatttt gcaactta                            98

<210> SEQ ID NO 76
<211> LENGTH: 98
<212> TYPE: DNA
<213> ORGANISM: Artificial Sequence
<220> FEATURE:
<223> OTHER INFORMATION: Description of Artificial Sequence: FR
      shuffling vector h5Lv2A

<400> SEQUENCE: 76
cttaagaagc ttttaatgtc ctgtgaggcc ttgcacgtga tggtgactct gtctcctaca     60
gatgcagaca gggaggatgg agactgggtc atctggat                            98

<210> SEQ ID NO 77
<211> LENGTH: 98
<212> TYPE: DNA
<213> ORGANISM: Artificial Sequence
<220> FEATURE:
<223> OTHER INFORMATION: Description of Artificial Sequence: FR
      shuffling vector h5Lv3A

<400> SEQUENCE: 77
gatgggaccc catctgccaa actagttgca taatagatca ggagcttagg ggctttccct     60
ggtttctgct gataccaact taagaagctt ttaatgtc                            98

<210> SEQ ID NO 78
<211> LENGTH: 94
<212> TYPE: DNA
```

<213> ORGANISM: Artificial Sequence
<220> FEATURE:
<223> OTHER INFORMATION: Description of Artificial Sequence: FR
      shuffling vector h5Lv5A

<400> SEQUENCE: 78
tgttcgtacg tttgatctcc accttggtcc ctccgccgaa cgtgtacggg ctctcaccat    60
gctgcagaca gtagtaagtt gcaaaatctt cagg    94

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Primer
      h5LvS

<400> SEQUENCE: 79
gtctagatct ccaccatgag    20

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Primer
      h5LvA

<400> SEQUENCE: 80
tgttcgtacg tttgatctc    19

<210> SEQ ID NO 81
<211> LENGTH: 381
<212> TYPE: DNA
<213> ORGANISM: Artificial Sequence
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)
<220> FEATURE:
<223> OTHER INFORMATION: Description of Artificial Sequence: Nucleotide
      sequence coding for version "a" of humanized L
      chain V region

<400> SEQUENCE: 81

```
atg agg gcc cct gct cag ttt ttt ggg atc ttg ttg ctc tgg ttt cca      48
Met Arg Ala Pro Ala Gln Phe Phe Gly Ile Leu Leu Leu Trp Phe Pro
-20             -15                 -10                 -5 ggg atc cga tgt gac atc cag atg acc cag tct cca tcc tcc ctg tct      96
Gly Ile Arg Cys Asp Ile Gln Met Thr Gln Ser Pro Ser Ser Leu Ser
        -1   1               5                   10 gca tct gta gga gac aga gtc acc atc acg tgc aag gcc tca cag gac     144
Ala Ser Val Gly Asp Arg Val Thr Ile Thr Cys Lys Ala Ser Gln Asp
            15                  20                  25 att aaa agc ttc tta agt tgg tat cag cag aaa cca ggg aaa gcc cct     192
Ile Lys Ser Phe Leu Ser Trp Tyr Gln Gln Lys Pro Gly Lys Ala Pro
        30                  35                  40 aag ctc ctg atc tat tat gca act agt ttg gca gat ggg gtc cca tca     240
Lys Leu Leu Ile Tyr Tyr Ala Thr Ser Leu Ala Asp Gly Val Pro Ser
    45                  50                  55                  60 agg ttc agt ggc tcc gga tct ggt acc gat ttc act ctc acc atc tcg     288
Arg Phe Ser Gly Ser Gly Ser Gly Thr Asp Phe Thr Leu Thr Ile Ser
```

```
                             65                  70                  75
agt ctg caa cct gaa gat ttt gca act tac tac tgt ctg cag cat ggt           336
Ser Leu Gln Pro Glu Asp Phe Ala Thr Tyr Tyr Cys Leu Gln His Gly
                 80                  85                  90 gag agc ccg tac acg ttc ggc gga ggg acc aag gtg gag atc aaa               381
Glu Ser Pro Tyr Thr Phe Gly Gly Gly Thr Lys Val Glu Ile Lys
                 95                 100                 105

<210> SEQ ID NO 82
<211> LENGTH: 127
<212> TYPE: PRT
<213> ORGANISM: Artificial Sequence
<220> FEATURE:
<223> OTHER INFORMATION: Description of Artificial Sequence: Amino acid
      sequence of version "a" of humanized L chain V
      region

<400> SEQUENCE: 82

Met Arg Ala Pro Ala Gln Phe Phe Gly Ile Leu Leu Leu Trp Phe Pro
-20                 -15                 -10                  -5

Gly Ile Arg Cys Asp Ile Gln Met Thr Gln Ser Pro Ser Ser Leu Ser
             -1   1                   5                  10

Ala Ser Val Gly Asp Arg Val Thr Ile Thr Cys Lys Ala Ser Gln Asp
                 15                  20                  25

Ile Lys Ser Phe Leu Ser Trp Tyr Gln Gln Lys Pro Gly Lys Ala Pro
         30                  35                  40

Lys Leu Leu Ile Tyr Tyr Ala Thr Ser Leu Ala Asp Gly Val Pro Ser
     45                  50                  55                  60

Arg Phe Ser Gly Ser Gly Ser Gly Thr Asp Phe Thr Leu Thr Ile Ser
                 65                  70                  75

Ser Leu Gln Pro Glu Asp Phe Ala Thr Tyr Tyr Cys Leu Gln His Gly
             80                  85                  90

Glu Ser Pro Tyr Thr Phe Gly Gly Gly Thr Lys Val Glu Ile Lys
             95                 100                 105

<210> SEQ ID NO 83
<211> LENGTH: 77
<212> TYPE: DNA
<213> ORGANISM: Artificial Sequence
<220> FEATURE:
<223> OTHER INFORMATION: Description of Artificial Sequence: FR
      shuffling primer F3SS

<400> SEQUENCE: 83
gtctggtacc gattacactc tcaccatctc gagcctccag cctgaagatt ttgcaactta       60
ctattgtctg cagaaca                                                      77

<210> SEQ ID NO 84
<211> LENGTH: 77
<212> TYPE: DNA
<213> ORGANISM: Artificial Sequence
<220> FEATURE:
<223> OTHER INFORMATION: Description of Artificial Sequence: FR
      shuffling primer F3SA

<400> SEQUENCE: 84
tgttctgcag acaatagtaa gttgcaaaat cttcaggctg gaggctcgag atggtgagag       60
tgtaatcggt accagac                                                      77

<210> SEQ ID NO 85
<211> LENGTH: 77
<212> TYPE: DNA
```

<213> ORGANISM: Artificial Sequence
<220> FEATURE:
<223> OTHER INFORMATION: Description of Artificial Sequence: FR
      shuffling primer F3RS

<400> SEQUENCE: 85

```
gtctggtacc gattacactc tcaccatctc gagcctccag cctgaagata ttgcaactta      60
ctattgtctg cagaaca                                                    77
```

<210> SEQ ID NO 86
<211> LENGTH: 77
<212> TYPE: DNA
<213> ORGANISM: Artificial Sequence
<220> FEATURE:
<223> OTHER INFORMATION: Description of Artificial Sequence: FR
      shuffling primer F3RA

<400> SEQUENCE: 86

```
tgttctgcag acaatagtaa gttgcaatat cttcaggctg gaggctcgag atggtgagag      60
tgtaatcggt accagac                                                    77
```

<210> SEQ ID NO 87
<211> LENGTH: 381
<212> TYPE: DNA
<213> ORGANISM: Artificial Sequence
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)
<220> FEATURE:
<223> OTHER INFORMATION: Description of Artificial Sequence: Nucleotide
      sequence coding for version "b" of humanized L
      chain V region

<400> SEQUENCE: 87

```
atg agg gcc cct gct cag ttt ttt ggg atc ttg ttg ctc tgg ttt cca        48
Met Arg Ala Pro Ala Gln Phe Phe Gly Ile Leu Leu Leu Trp Phe Pro
-20              -15                 -10                  -5 ggg atc cga tgt gac atc cag atg acc cag tct cca tcc tcc ctg tct        96
Gly Ile Arg Cys Asp Ile Gln Met Thr Gln Ser Pro Ser Ser Leu Ser
             -1   1               5                  10 gca tct gta gga gac aga gtc acc atc acg tgc aag gcc tca cag gac       144
Ala Ser Val Gly Asp Arg Val Thr Ile Thr Cys Lys Ala Ser Gln Asp
        15                  20                  25 att aaa agc ttc tta agt tgg tat cag cag aaa cca ggg aaa gcc cct       192
Ile Lys Ser Phe Leu Ser Trp Tyr Gln Gln Lys Pro Gly Lys Ala Pro
    30                  35                  40 aag ctc ctg atc tat tat gca act agt ttg gca gat ggg gtc cca tca       240
Lys Leu Leu Ile Tyr Tyr Ala Thr Ser Leu Ala Asp Gly Val Pro Ser
45                  50                  55                  60 agg ttc agt ggc tcc gga tct ggt acc gat tac act ctc acc atc tcg       288
Arg Phe Ser Gly Ser Gly Ser Gly Thr Asp Tyr Thr Leu Thr Ile Ser
                65                  70                  75 agc ctc cag cct gaa gat ttt gca act tac tat tgt ctg cag cat ggt       336
Ser Leu Gln Pro Glu Asp Phe Ala Thr Tyr Tyr Cys Leu Gln His Gly
            80                  85                  90 gag agc ccg tac acg ttc ggc gga ggg acc aag gtg gag atc aaa           381
Glu Ser Pro Tyr Thr Phe Gly Gly Gly Thr Lys Val Glu Ile Lys
        95                 100                 105
```

```
<210> SEQ ID NO 88
<211> LENGTH: 127
<212> TYPE: PRT
<213> ORGANISM: Artificial Sequence
<220> FEATURE:
<223> OTHER INFORMATION: Description of Artificial Sequence: Amino acid
      sequence of version "b" of humanized L chain V
      region

<400> SEQUENCE: 88

Met Arg Ala Pro Ala Gln Phe Phe Gly Ile Leu Leu Leu Trp Phe Pro
-20                 -15                 -10                  -5

Gly Ile Arg Cys Asp Ile Gln Met Thr Gln Ser Pro Ser Ser Leu Ser
             -1   1               5                  10

Ala Ser Val Gly Asp Arg Val Thr Ile Thr Cys Lys Ala Ser Gln Asp
             15                  20                  25

Ile Lys Ser Phe Leu Ser Trp Tyr Gln Gln Lys Pro Gly Lys Ala Pro
     30                  35                  40

Lys Leu Leu Ile Tyr Tyr Ala Thr Ser Leu Ala Asp Gly Val Pro Ser
 45                  50                  55                  60

Arg Phe Ser Gly Ser Gly Ser Gly Thr Asp Tyr Thr Leu Thr Ile Ser
             65                  70                  75

Ser Leu Gln Pro Glu Asp Phe Ala Thr Tyr Tyr Cys Leu Gln His Gly
             80                  85                  90

Glu Ser Pro Tyr Thr Phe Gly Gly Thr Lys Val Glu Ile Lys
             95                  100                 105

<210> SEQ ID NO 89
<211> LENGTH: 381
<212> TYPE: DNA
<213> ORGANISM: Artificial Sequence
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)
<220> FEATURE:
<223> OTHER INFORMATION: Description of Artificial Sequence: Nucleotide
      sequence coding for version "c" of humanized L
      chain V region

<400> SEQUENCE: 89 atg agg gcc cct gct cag ttt ttt ggg atc ttg ttg ctc tgg ttt cca      48
Met Arg Ala Pro Ala Gln Phe Phe Gly Ile Leu Leu Leu Trp Phe Pro
-20                 -15                 -10                  -5 ggg atc cga tgt gac atc cag atg acc cag tct cca tcc tcc ctg tct     96
Gly Ile Arg Cys Asp Ile Gln Met Thr Gln Ser Pro Ser Ser Leu Ser
             -1   1               5                  10 gca tct gta gga gac aga gtc acc atc acg tgc aag gcc tca cag gac    144
Ala Ser Val Gly Asp Arg Val Thr Ile Thr Cys Lys Ala Ser Gln Asp
             15                  20                  25 att aaa agc ttc tta agt tgg tat cag cag aaa cca ggg aaa gcc cct    192
Ile Lys Ser Phe Leu Ser Trp Tyr Gln Gln Lys Pro Gly Lys Ala Pro
     30                  35                  40 aag ctc ctg atc tat tat gca act agt ttg gca gat ggg gtc cca tca    240
Lys Leu Leu Ile Tyr Tyr Ala Thr Ser Leu Ala Asp Gly Val Pro Ser
 45                  50                  55                  60 agg ttc agt ggc tcc gga tct ggt acc gat tac act ctc acc atc tcg    288
Arg Phe Ser Gly Ser Gly Ser Gly Thr Asp Tyr Thr Leu Thr Ile Ser
             65                  70                  75
```

```
agc ctc cag cct gaa gat att gca act tac tat tgt ctg cag cat ggt      336
Ser Leu Gln Pro Glu Asp Ile Ala Thr Tyr Tyr Cys Leu Gln His Gly
        80                  85                  90 gag agc ccg tac acg ttc ggc gga ggg acc aag gtg gag atc aaa          381
Glu Ser Pro Tyr Thr Phe Gly Gly Gly Thr Lys Val Glu Ile Lys
        95                 100                 105

<210> SEQ ID NO 90
<211> LENGTH: 127
<212> TYPE: PRT
<213> ORGANISM: Artificial Sequence
<220> FEATURE:
<223> OTHER INFORMATION: Description of Artificial Sequence: Amino acid
      sequence of version "c" of humanized L chain V
      region

<400> SEQUENCE: 90

Met Arg Ala Pro Ala Gln Phe Phe Gly Ile Leu Leu Leu Trp Phe Pro
-20                 -15                 -10                  -5

Gly Ile Arg Cys Asp Ile Gln Met Thr Gln Ser Pro Ser Ser Leu Ser
            -1   1               5                  10

Ala Ser Val Gly Asp Arg Val Thr Ile Thr Cys Lys Ala Ser Gln Asp
        15                  20                  25

Ile Lys Ser Phe Leu Ser Trp Tyr Gln Gln Lys Pro Gly Lys Ala Pro
        30                  35                  40

Lys Leu Leu Ile Tyr Tyr Ala Thr Ser Leu Ala Asp Gly Val Pro Ser
    45                  50                  55                  60

Arg Phe Ser Gly Ser Gly Ser Gly Thr Asp Tyr Thr Leu Thr Ile Ser
                65                  70                  75

Ser Leu Gln Pro Glu Asp Ile Ala Thr Tyr Tyr Cys Leu Gln His Gly
        80                  85                  90

Glu Ser Pro Tyr Thr Phe Gly Gly Gly Thr Lys Val Glu Ile Lys
        95                 100                 105

<210> SEQ ID NO 91
<211> LENGTH: 72
<212> TYPE: DNA
<213> ORGANISM: Artificial Sequence
<220> FEATURE:
<223> OTHER INFORMATION: Description of Artificial Sequence: FR
      shuffling primer F2SS

<400> SEQUENCE: 91
gtctcttaag ttggttccag cagaaaccag ggaaatctcc taagaccctg atctactatg     60
caactagtaa ca                                                        72

<210> SEQ ID NO 92
<211> LENGTH: 72
<212> TYPE: DNA
<213> ORGANISM: Artificial Sequence
<220> FEATURE:
<223> OTHER INFORMATION: Description of Artificial Sequence: FR
      shuffling primer F2SA

<400> SEQUENCE: 92
tgttactagt tgcatagtag atcagggtct taggagattt ccctggtttc tgctggaacc     60
aacttaagag ac                                                        72

<210> SEQ ID NO 93
<211> LENGTH: 72
<212> TYPE: DNA
<213> ORGANISM: Artificial Sequence
<220> FEATURE:
```

-continued

<223> OTHER INFORMATION: Description of Artificial Sequence: FR
      shuffling primer F2XS

<400> SEQUENCE: 93
gtctcttaag ttggtatcag cagaaaccag agaaagcccc taagtccctg atctattatg    60
caactagtaa ca    72

<210> SEQ ID NO 94
<211> LENGTH: 72
<212> TYPE: DNA
<213> ORGANISM: Artificial Sequence
<220> FEATURE:
<223> OTHER INFORMATION: Description of Artificial Sequence: FR
      shuffling primer F2XA

<400> SEQUENCE: 94
tgttactagt tgcataatag atcagggact tagggggcttt ctctggtttc tgctgatacc    60
aacttaagag ac    72

<210> SEQ ID NO 95
<211> LENGTH: 381
<212> TYPE: DNA
<213> ORGANISM: Artificial Sequence
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)
<220> FEATURE:
<223> OTHER INFORMATION: Description of Artificial Sequence: Nucleotide
      sequence coding for version "b1" of humanized L
      chain V region

<400> SEQUENCE: 95 atg agg gcc cct gct cag ttt ttt ggg atc ttg ttg ctc tgg ttt cca      48
Met Arg Ala Pro Ala Gln Phe Phe Gly Ile Leu Leu Leu Trp Phe Pro
-20              -15                  -10                  -5 ggg atc cga tgt gac atc cag atg acc cag tct cca tcc tcc ctg tct      96
Gly Ile Arg Cys Asp Ile Gln Met Thr Gln Ser Pro Ser Ser Leu Ser
             -1  1                5                   10 gca tct gta gga gac aga gtc acc atc acg tgc aag gcc tca cag gac     144
Ala Ser Val Gly Asp Arg Val Thr Ile Thr Cys Lys Ala Ser Gln Asp
             15                  20                  25 att aaa agc ttc tta agt tgg ttc cag cag aaa cca ggg aaa tct cct     192
Ile Lys Ser Phe Leu Ser Trp Phe Gln Gln Lys Pro Gly Lys Ser Pro
         30                  35                  40 aag acc ctg atc tac tat gca act agt ttg gca gat ggg gtc cca tca     240
Lys Thr Leu Ile Tyr Tyr Ala Thr Ser Leu Ala Asp Gly Val Pro Ser
 45                  50                  55                  60 agg ttc agt ggc tcc gga tct ggt acc gat tac act ctc acc atc tcg     288
Arg Phe Ser Gly Ser Gly Ser Gly Thr Asp Tyr Thr Leu Thr Ile Ser
                     65                  70                  75 agc ctc cag cct gaa gat ttt gca act tac tat tgt ctg cag cat ggt     336
Ser Leu Gln Pro Glu Asp Phe Ala Thr Tyr Tyr Cys Leu Gln His Gly
             80                  85                  90 gag agc ccg tac acg ttc ggc gga ggg acc aag gtg gag atc aaa         381
Glu Ser Pro Tyr Thr Phe Gly Gly Gly Thr Lys Val Glu Ile Lys
         95                  100                 105

<210> SEQ ID NO 96
<211> LENGTH: 127

```
<212> TYPE: PRT
<213> ORGANISM: Artificial Sequence
<220> FEATURE:
<223> OTHER INFORMATION: Description of Artificial Sequence: Amino acid
      sequence of version "b1" of humanized L chain V
      region

<400> SEQUENCE: 96

Met Arg Ala Pro Ala Gln Phe Phe Gly Ile Leu Leu Leu Trp Phe Pro
-20             -15                 -10                  -5

Gly Ile Arg Cys Asp Ile Gln Met Thr Gln Ser Pro Ser Ser Leu Ser
            -1   1             5                  10

Ala Ser Val Gly Asp Arg Val Thr Ile Thr Cys Lys Ala Ser Gln Asp
            15                  20                  25

Ile Lys Ser Phe Leu Ser Trp Phe Gln Gln Lys Pro Gly Lys Ser Pro
    30                  35                  40

Lys Thr Leu Ile Tyr Tyr Ala Thr Ser Leu Ala Asp Gly Val Pro Ser
45                  50                  55                  60

Arg Phe Ser Gly Ser Gly Ser Gly Thr Asp Tyr Thr Leu Thr Ile Ser
                65                  70                  75

Ser Leu Gln Pro Glu Asp Phe Ala Thr Tyr Tyr Cys Leu Gln His Gly
            80                  85                  90

Glu Ser Pro Tyr Thr Phe Gly Gly Gly Thr Lys Val Glu Ile Lys
            95                  100                 105

<210> SEQ ID NO 97
<211> LENGTH: 381
<212> TYPE: DNA
<213> ORGANISM: Artificial Sequence
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)
<220> FEATURE:
<223> OTHER INFORMATION: Description of Artificial Sequence: Nucleotide
      sequence coding for version "b2" of humanized L
      chain V region

<400> SEQUENCE: 97 atg agg gcc cct gct cag ttt ttt ggg atc ttg ttg ctc tgg ttt cca      48
Met Arg Ala Pro Ala Gln Phe Phe Gly Ile Leu Leu Leu Trp Phe Pro
-20             -15                 -10                  -5 ggg atc cga tgt gac atc cag atg acc cag tct cca tcc tcc ctg tct      96
Gly Ile Arg Cys Asp Ile Gln Met Thr Gln Ser Pro Ser Ser Leu Ser
            -1   1             5                  10 gca tct gta gga gac aga gtc acc atc acg tgc aag gcc tca cag gac     144
Ala Ser Val Gly Asp Arg Val Thr Ile Thr Cys Lys Ala Ser Gln Asp
            15                  20                  25 att aaa agc ttc tta agt tgg tat cag cag aaa cca gag aaa gcc cct     192
Ile Lys Ser Phe Leu Ser Trp Tyr Gln Gln Lys Pro Glu Lys Ala Pro
    30                  35                  40 aag tcc ctg atc tat tat gca act agt ttg gca gat ggg gtc cca tca     240
Lys Ser Leu Ile Tyr Tyr Ala Thr Ser Leu Ala Asp Gly Val Pro Ser
45                  50                  55                  60 agg ttc agt ggc tcc gga tct ggt acc gat tac act ctc acc atc tcg     288
Arg Phe Ser Gly Ser Gly Ser Gly Thr Asp Tyr Thr Leu Thr Ile Ser
                65                  70                  75 agc ctc cag cct gaa gat ttt gca act tac tat tgt ctg cag cat ggt     336
Ser Leu Gln Pro Glu Asp Phe Ala Thr Tyr Tyr Cys Leu Gln His Gly
```

```
                 80                  85                  90
gag agc ccg tac acg ttc ggc gga ggg acc aag gtg gag atc aaa        381
Glu Ser Pro Tyr Thr Phe Gly Gly Gly Thr Lys Val Glu Ile Lys
        95                 100                 105
```

<210> SEQ ID NO 98
<211> LENGTH: 127
<212> TYPE: PRT
<213> ORGANISM: Artificial Sequence
<220> FEATURE:
<223> OTHER INFORMATION: Description of Artificial Sequence: Amino acid
      sequence of version "b2" of humanized L chain V
      region

<400> SEQUENCE: 98

```
Met Arg Ala Pro Ala Gln Phe Phe Gly Ile Leu Leu Leu Trp Phe Pro
-20                 -15                 -10                  -5

Gly Ile Arg Cys Asp Ile Gln Met Thr Gln Ser Pro Ser Ser Leu Ser
             -1   1                   5                      10

Ala Ser Val Gly Asp Arg Val Thr Ile Thr Cys Lys Ala Ser Gln Asp
            15                  20                  25

Ile Lys Ser Phe Leu Ser Trp Tyr Gln Gln Lys Pro Glu Lys Ala Pro
    30                  35                  40

Lys Ser Leu Ile Tyr Tyr Ala Thr Ser Leu Ala Asp Gly Val Pro Ser
45                  50                  55                  60

Arg Phe Ser Gly Ser Gly Ser Gly Thr Asp Tyr Thr Leu Thr Ile Ser
                65                  70                  75

Ser Leu Gln Pro Glu Asp Phe Ala Thr Tyr Tyr Cys Leu Gln His Gly
            80                  85                  90

Glu Ser Pro Tyr Thr Phe Gly Gly Gly Thr Lys Val Glu Ile Lys
        95                 100                 105
```

<210> SEQ ID NO 99
<211> LENGTH: 136
<212> TYPE: PRT
<213> ORGANISM: Mus sp.
<220> FEATURE:
<223> OTHER INFORMATION: Amino acid sequence of H chain V region of
      anti TF mouse monoclonal antibody ATR-5

<400> SEQUENCE: 99

```
Met Lys Cys Ser Trp Val Ile Phe Phe Leu Met Ala Val Val Thr Gly
                -15                 -10                  -5

Val Asn Ser Glu Val Gln Leu Gln Gln Ser Gly Thr Asn Leu Val Arg
             -1   1                   5                      10

Pro Gly Ala Leu Val Lys Leu Ser Cys Lys Gly Ser Gly Phe Asn Ile
            15                  20                  25

Lys Asp Tyr Tyr Met His Trp Val Lys Gln Arg Pro Glu Gln Gly Leu
30                  35                  40                  45

Glu Trp Ile Gly Gly Asn Asp Pro Ala Asn Gly His Ser Met Tyr Asp
                50                  55                  60

Pro Lys Phe Gln Gly Lys Ala Ser Ile Thr Ala Asp Thr Ser Ser Asn
            65                  70                  75

Thr Ala Tyr Leu Gln Leu Ser Ser Leu Thr Ser Glu Asp Thr Ala Val
            80                  85                  90

Tyr Phe Cys Ala Arg Asp Ser Gly Tyr Ala Met Asp Tyr Trp Gly Gln
        95                 100                 105

Gly Thr Ser Val Thr Val Ser Ser
110                 115
```

<210> SEQ ID NO 100
<211> LENGTH: 127
<212> TYPE: PRT
<213> ORGANISM: Mus sp.
<220> FEATURE:
<223> OTHER INFORMATION: Amino acid sequence of L chain V region of
      anti TF mouse monoclonal antibody ATR-5

<400> SEQUENCE: 100

Met Arg Ala Pro Ala Gln Phe Phe Gly Ile Leu Leu Leu Trp Phe Pro
-20                 -15                 -10                 -5

Gly Ile Arg Cys Asp Ile Lys Met Thr Gln Ser Pro Ser Ser Met Tyr
            -1   1               5                  10

Ala Ser Leu Gly Glu Arg Val Thr Ile Thr Cys Lys Ala Ser Gln Asp
            15                  20                  25

Ile Lys Ser Phe Leu Ser Trp Tyr Gln Gln Lys Pro Trp Lys Ser Pro
        30                  35                  40

Lys Thr Leu Ile Tyr Tyr Ala Thr Ser Leu Ala Asp Gly Val Pro Ser
    45                  50                  55                  60

Arg Phe Ser Gly Ser Gly Ser Gly Gln Asp Tyr Ser Leu Thr Ile Asn
                65                  70                  75

Asn Leu Glu Ser Asp Asp Thr Ala Thr Tyr Tyr Cys Leu Gln His Gly
            80                  85                  90

Glu Ser Pro Tyr Thr Phe Gly Gly Thr Lys Leu Glu Ile Lys
            95                  100                 105

<210> SEQ ID NO 101
<211> LENGTH: 780
<212> TYPE: DNA
<213> ORGANISM: Homo sapiens
<220> FEATURE:
<221> NAME/KEY: CDS
<222> LOCATION: (1)..(777)
<220> FEATURE:
<221> NAME/KEY: sig_peptide
<222> LOCATION: (1)..(96)
<220> FEATURE:
<221> NAME/KEY: mat_peptide
<222> LOCATION: (97)..(777)
<223> OTHER INFORMATION: DNA coding for soluble human TF

<400> SEQUENCE: 101 atg gag acc cct gcc tgg ccc cgg gtc ccg cgc ccc gag acc gcc gtc      48
Met Glu Thr Pro Ala Trp Pro Arg Val Pro Arg Pro Glu Thr Ala Val
-30                 -25                 -20 gct cgg acg ctc ctg ctc ggc tgg gtc ttc gcc cag gtg gcc ggc gct      96
Ala Arg Thr Leu Leu Leu Gly Trp Val Phe Ala Gln Val Ala Gly Ala
    -15                 -10                 -5              -1 tca ggc act aca aat act gtg gca gca tat aat tta act tgg aaa tca     144
Ser Gly Thr Thr Asn Thr Val Ala Ala Tyr Asn Leu Thr Trp Lys Ser
1               5                   10                  15 act aat ttc aag aca att ttg gag tgg gaa ccc aaa ccc gtc aat caa     192
Thr Asn Phe Lys Thr Ile Leu Glu Trp Glu Pro Lys Pro Val Asn Gln
                20                  25                  30 gtc tac act gtt caa ata agc act aag tca gga gat tgg aaa agc aaa     240
Val Tyr Thr Val Gln Ile Ser Thr Lys Ser Gly Asp Trp Lys Ser Lys
            35                  40                  45 tgc ttt tac aca aca gac aca gag tgt gac ctc acc gac gag att gtg     288
Cys Phe Tyr Thr Thr Asp Thr Glu Cys Asp Leu Thr Asp Glu Ile Val
        50                  55                  60 aag gat gtg aag cag acg tac ttg gca cgg gtc ttc tcc tac ccg gca     336
Lys Asp Val Lys Gln Thr Tyr Leu Ala Arg Val Phe Ser Tyr Pro Ala
65                  70                  75                  80

```
ggg aat gtg gag agc acc ggt tct gct ggg gag cct ctg tat gag aac      384
Gly Asn Val Glu Ser Thr Gly Ser Ala Gly Glu Pro Leu Tyr Glu Asn
             85                  90                  95 tcc cca gag ttc aca cct tac ctg gag aca aac ctc gga cag cca aca      432
Ser Pro Glu Phe Thr Pro Tyr Leu Glu Thr Asn Leu Gly Gln Pro Thr
        100                 105                 110 att cag agt ttt gaa cag gtg gga aca aaa gtg aat gtg acc gta gaa      480
Ile Gln Ser Phe Glu Gln Val Gly Thr Lys Val Asn Val Thr Val Glu
            115                 120                 125 gat gaa cgg act tta gtc aga agg aac aac act ttc cta agc ctc cgg      528
Asp Glu Arg Thr Leu Val Arg Arg Asn Asn Thr Phe Leu Ser Leu Arg
    130                 135                 140 gat gtt ttt ggc aag gac tta att tat aca ctt tat tat tgg aaa tct      576
Asp Val Phe Gly Lys Asp Leu Ile Tyr Thr Leu Tyr Tyr Trp Lys Ser
145                 150                 155                 160 tca agt tca gga aag aaa aca gcc aaa aca aac act aat gag ttt ttg      624
Ser Ser Ser Gly Lys Lys Thr Ala Lys Thr Asn Thr Asn Glu Phe Leu
                165                 170                 175 att gat gtg gat aaa gga gaa aac tac tgt ttc agt gtt caa gca gtg      672
Ile Asp Val Asp Lys Gly Glu Asn Tyr Cys Phe Ser Val Gln Ala Val
            180                 185                 190 att ccc tcc cga aca gtt aac cgg aag agt aca gac agc ccg gta gag      720
Ile Pro Ser Arg Thr Val Asn Arg Lys Ser Thr Asp Ser Pro Val Glu
        195                 200                 205 tgt atg ggc cag gag aaa ggg gaa ttc aga gaa gac tac aaa gac gat      768
Cys Met Gly Gln Glu Lys Gly Glu Phe Arg Glu Asp Tyr Lys Asp Asp
    210                 215                 220 gac gat aaa taa                                                       780
Asp Asp Lys
225

<210> SEQ ID NO 102
<211> LENGTH: 259
<212> TYPE: PRT
<213> ORGANISM: Homo sapiens
<220> FEATURE:
<223> OTHER INFORMATION: Amino acid sequence of soluble human TF

<400> SEQUENCE: 102

Met Glu Thr Pro Ala Trp Pro Arg Val Pro Arg Pro Glu Thr Ala Val
        -30                 -25                 -20

Ala Arg Thr Leu Leu Leu Gly Trp Val Phe Ala Gln Val Ala Gly Ala
    -15                 -10                  -5                  -1

Ser Gly Thr Thr Asn Thr Val Ala Ala Tyr Asn Leu Thr Trp Lys Ser
  1                   5                  10                  15

Thr Asn Phe Lys Thr Ile Leu Glu Trp Glu Pro Lys Pro Val Asn Gln
             20                  25                  30

Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
     50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
             85                  90                  95

Ser Pro Glu Phe Thr Pro Tyr Leu Glu Thr Asn Leu Gly Gln Pro Thr
        100                 105                 110

Ile Gln Ser Phe Glu Gln Val Gly Thr Lys Val Asn Val Thr Val Glu
            115                 120                 125
```

```
Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Asp Tyr Lys Asp Asp
    210                 215                 220

Asp Asp Lys
225

<210> SEQ ID NO 103
<211> LENGTH: 888
<212> TYPE: DNA
<213> ORGANISM: Homo sapiens
<220> FEATURE:
<221> NAME/KEY: CDS
<222> LOCATION: (1)..(885)
<220> FEATURE:
<221> NAME/KEY: sig_peptide
<222> LOCATION: (1)..(96)
<220> FEATURE:
<221> NAME/KEY: mat_peptide
<222> LOCATION: (97)..(885)
<223> OTHER INFORMATION: DNA coding for human TF

<400> SEQUENCE: 103 atg gag acc cct gcc tgg ccc cgg gtc ccg cgc ccc gag acc gcc gtc       48
Met Glu Thr Pro Ala Trp Pro Arg Val Pro Arg Pro Glu Thr Ala Val
        -30                 -25                 -20 gct cgg acg ctc ctg ctc ggc tgg gtc ttc gcc cag gtg gcc ggc gct       96
Ala Arg Thr Leu Leu Leu Gly Trp Val Phe Ala Gln Val Ala Gly Ala
    -15                 -10                 -5              -1 tca ggc act aca aat act gtg gca gca tat aat tta act tgg aaa tca      144
Ser Gly Thr Thr Asn Thr Val Ala Ala Tyr Asn Leu Thr Trp Lys Ser
1                   5                   10                  15 act aat ttc aag aca att ttg gag tgg gaa ccc aaa ccc gtc aat caa      192
Thr Asn Phe Lys Thr Ile Leu Glu Trp Glu Pro Lys Pro Val Asn Gln
                20                  25                  30 gtc tac act gtt caa ata agc act aag tca gga gat tgg aaa agc aaa      240
Val Tyr Thr Val Gln Ile Ser Thr Lys Ser Gly Asp Trp Lys Ser Lys
            35                  40                  45 tgc ttt tac aca aca gac aca gag tgt gac ctc acc gac gag att gtg      288
Cys Phe Tyr Thr Thr Asp Thr Glu Cys Asp Leu Thr Asp Glu Ile Val
        50                  55                  60 aag gat gtg aag cag acg tac ttg gca cgg gtc ttc tcc tac ccg gca      336
Lys Asp Val Lys Gln Thr Tyr Leu Ala Arg Val Phe Ser Tyr Pro Ala
    65                  70                  75                  80 ggg aat gtg gag agc acc ggt tct gct ggg gag cct ctg tat gag aac      384
Gly Asn Val Glu Ser Thr Gly Ser Ala Gly Glu Pro Leu Tyr Glu Asn
                85                  90                  95 tcc cca gag ttc aca cct tac ctg gag aca aac ctc gga cag cca aca      432
Ser Pro Glu Phe Thr Pro Tyr Leu Glu Thr Asn Leu Gly Gln Pro Thr
            100                 105                 110 att cag agt ttt gaa cag gtg gga aca aaa gtg aat gtg acc gta gaa      480
Ile Gln Ser Phe Glu Gln Val Gly Thr Lys Val Asn Val Thr Val Glu
        115                 120                 125
```

```
gat gaa cgg act tta gtc aga agg aac aac act ttc cta agc ctc cgg    528
Asp Glu Arg Thr Leu Val Arg Arg Asn Asn Thr Phe Leu Ser Leu Arg
    130             135                 140 gat gtt ttt ggc aag gac tta att tat aca ctt tat tat tgg aaa tct    576
Asp Val Phe Gly Lys Asp Leu Ile Tyr Thr Leu Tyr Tyr Trp Lys Ser
145                 150                 155                 160 tca agt tca gga aag aaa aca gcc aaa aca aac act aat gag ttt ttg    624
Ser Ser Ser Gly Lys Lys Thr Ala Lys Thr Asn Thr Asn Glu Phe Leu
                165                 170                 175 att gat gtg gat aaa gga gaa aac tac tgt ttc agt gtt caa gca gtg    672
Ile Asp Val Asp Lys Gly Glu Asn Tyr Cys Phe Ser Val Gln Ala Val
            180                 185                 190 att ccc tcc cga aca gtt aac cgg aag agt aca gac agc ccg gta gag    720
Ile Pro Ser Arg Thr Val Asn Arg Lys Ser Thr Asp Ser Pro Val Glu
        195                 200                 205 tgt atg ggc cag gag aaa ggg gaa ttc aga gaa ata ttc tac atc att    768
Cys Met Gly Gln Glu Lys Gly Glu Phe Arg Glu Ile Phe Tyr Ile Ile
    210                 215                 220 gga gct gtg gta ttt gtg gtc atc atc ctt gtc atc atc ctg gct ata    816
Gly Ala Val Val Phe Val Val Ile Ile Leu Val Ile Ile Leu Ala Ile
225                 230                 235                 240 tct cta cac aag tgt aga aag gca gga gtg ggg cag agc tgg aag gag    864
Ser Leu His Lys Cys Arg Lys Ala Gly Val Gly Gln Ser Trp Lys Glu
                245                 250                 255 aac tcc cca ctg aat gtt tca taa                                    888
Asn Ser Pro Leu Asn Val Ser
            260
```

```
<210> SEQ ID NO 104
<211> LENGTH: 295
<212> TYPE: PRT
<213> ORGANISM: Homo sapiens
<220> FEATURE:
<223> OTHER INFORMATION: Amino acid sequence of soluble human TF

<400> SEQUENCE: 104

Met Glu Thr Pro Ala Trp Pro Arg Val Pro Arg Pro Glu Thr Ala Val
        -30                 -25                 -20

Ala Arg Thr Leu Leu Leu Gly Trp Val Phe Ala Gln Val Ala Gly Ala
    -15                 -10                 -5                  -1

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
```

-continued

| 145 | | | | 150 | | | | 155 | | | | 160 | |
|---|---|---|---|---|---|---|---|---|---|---|---|---|---|
| Ser | Ser | Ser | Gly | Lys | Lys | Thr | Ala | Lys | Thr | Asn | Thr | Asn | Glu | Phe | Leu |
| | | | | 165 | | | | | 170 | | | | | 175 | |
| Ile | Asp | Val | Asp | Lys | Gly | Glu | Asn | Tyr | Cys | Phe | Ser | Val | Gln | Ala | Val |
| | | | 180 | | | | | 185 | | | | | 190 | | |
| Ile | Pro | Ser | Arg | Thr | Val | Asn | Arg | Lys | Ser | Thr | Asp | Ser | Pro | Val | Glu |
| | | 195 | | | | | 200 | | | | | 205 | | | |
| Cys | Met | Gly | Gln | Glu | Lys | Gly | Glu | Phe | Arg | Glu | Ile | Phe | Tyr | Ile | Ile |
| | 210 | | | | | 215 | | | | | 220 | | | | |
| Gly | Ala | Val | Val | Phe | Val | Val | Ile | Ile | Leu | Val | Ile | Ile | Leu | Ala | Ile |
| 225 | | | | | 230 | | | | | 235 | | | | | 240 |
| Ser | Leu | His | Lys | Cys | Arg | Lys | Ala | Gly | Val | Gly | Gln | Ser | Trp | Lys | Glu |
| | | | | 245 | | | | | 250 | | | | | 255 | |
| Asn | Ser | Pro | Leu | Asn | Val | Ser | | | | | | | | | |
| | | 260 | | | | | | | | | | | | | |

PREVENTION AND TREATMENT OF DISEASES ASSOCIATED WITH BLOOD COAGULATION

FIELD OF THE INVENTION

The present invention relates to a method of generating an animal model having a persistently hypercoagulable state, preventive or therapeutic agents for diseases having a persistent hypercoagulable state, preventive or therapeutic agents for a hypercoagulable state resulting from infections, preventive or therapeutic agents for venous or arterial thrombosis, and preventive or therapeutic agents for diseases resulting from the hypertrophy of vascular media.

BACKGROUND ART

Blood coagulation is a reaction in which serine protease precursors are successively activated by activated-form proteases, which finally generate thrombin thereby leading to fibrin formation. Thrombosis arises as a consequence of an excessively enhanced blood coagulation reaction that was caused by changes in the plasma coagulation and fibrinolytic system, and in the functions of platelets, leucocytes and vascular endothelial cells associated with the progression of various disease states. The initiating factor of the blood coagulation reaction is tissue factor. In acute coronary syndromes such as acute myocardial infarction and unstable angina, the blood coagulation reaction is triggered when tissue factor occurring in abundance in the plaques formed after the progression of arterial sclerosis is exposed to the blood due to the rhexis of plaques.

In the disseminated intravascular coagulation syndrome associated with sepsis and malignant tumors, activated monocytes and macrophages express tissue factor or tumor cells express tissue factor thereby causing enhanced blood coagulation. Once tissue factor comes into contact with the blood, the blood coagulation reaction proceeds in a very short period of time and leads to the formation of blood clots. Thus, in order to prevent thrombus formation, it is necessary to block blood coagulation reactions that may be triggered at any time or that may be constantly occurring. Therefore, an experimental model that exhibits a hypercoagulable state on a persistent basis is essential for the development of effective anti-thrombotic agents. In any of the conventionally known thrombotic models, thrombus formation is induced in a short period of time.

Thus, according to one aspect of the present invention, there is provided an experimental model in which a hypercoagulable state persists by bringing human tissue factor into contact with the blood on a persistent basis.

Blood coagulation is a reaction in which serine protease precursors are successively activated by activated-form proteases, which finally generate thrombin thereby leading to fibrin formation. Thrombosis arises as a consequence of an excessively enhanced blood coagulation reaction that was caused by changes in the plasma coagulation and fibrinolytic system, and in the functions of platelets, leucocytes and vascular endothelial cells associated with the progression of various disease states. The initiating factor of the blood coagulation reaction is tissue factor (TF).

In acute coronary syndromes such as acute myocardial infarction and unstable angina, the blood coagulation reaction is triggered when tissue factor occurring in abundance in the plaques formed after the progression of arterial sclerosis is exposed to the blood due to the rupture of plaques. In disseminated intravascular coagulation syndrome associated with sepsis and malignant tumors, activated monocytes and macrophages express TF or tumor cells express TF thereby leading to enhanced blood coagulation and this state persists. Once TF comes into contact with the blood, the blood coagulation reaction proceeds in a very short period of time leading to the formation of blood clots. Thus, in order to prevent thrombus formation, it is necessary to block blood coagulation reactions that may be triggered at any time or that may be constantly occurring. Therefore, as an effective anti-thrombotic agent, a drug is required that can block the persistence of the hypercoagulable state that is occurring on a constant basis.

Thus, according to the second aspect of the present invention, there is provided a novel preventive or therapeutic agent for diseases having a persistent hypercoagulable state.

Severe infections are often associated with abnormal coagulation, which induces disease states such as multiple organ failure and the disseminated intravascular coagulation syndrome, and represents a factor that aggravates the prognosis of the patient. The measures employed are thus considered to be important. In severe infections, systemic infections such as sepsis and, among them, lesions in the vascular endothelial cells have been implicated as the onset mechanism of organ disorders. In sepsis, and particular in sepsis caused by gram negative bacteria, a cellular component, lipopolysaccharide (LPS), plays an important role.

LPS liberated into the blood not only activates monocytes and thereby produces tissue factor (TF) leading to a hypercoagulable state, but produces and liberates cytokines such as TNF, IL-$\beta$ and IL-8 and thereby activates neutrophils and vascular endothelial cells. The activated neutrophils adhere to the vascular endothelial cells to liberate cytotoxic substances such as active enzymes and elastases, which injure the vascular endothelial cells. In the vascular endothelial cells activated by cytokines or injured by neutrophils, the production of TF is enhanced which further progresses the hypercoagulable state. As a result, microthrombi occur systemically, which elicits circulatory failures in the organs leading to multiple organ failure.

Thus, there is a great need for the development of preventive or therapeutic agents for blood coagulable states caused by infections.

Thus, according to the third aspect of the present invention, there is provided a novel preventive or therapeutic agent for blood coagulable states caused by infections.

As a mechanism leading to the onset of venous thrombosis, venous stasis, damages to the venous wall, and hypercoagulabilyty are thought to play an important role. In particular, invasive events such as surgery, childbirth and trauma induce physical injuries to the vascular wall and abnormalities in the coagulation and fibrinolysis system, and decubitus after surgery induces a renous stasis. Not only the resulting blood clots in the vein induce circulatory failure in the limbs but the clots themselves enter into the blood circulation and flows into the pulmonary artery leading to fatal pulmonary embolism. Hence, the prevention of venous thrombosis itself is considered to be important. Thus, there is a need for the development of agents that can effectively prevent or treat venous thrombosis.

Thus, according to the fourth aspect of the present invention, there is provided a novel preventive or therapeutic agent for the treatment of venous thrombosis.

In arterial thrombosis, blood clots occur in the blood vessel having an advanced sclerosis, and the onset of the disease in the important organs such as the brain and the heart would be fatal in most cases. In particular, acute coronary syndromes such as unstable angina and acute myocardial infarction are believed to be dangerous disease states that could easily cause sudden death. Recently it was demonstrated that the rhexis of the arteriosclerotic plaques and the ensuing thrombus formation is an important factor in the onset mechanism of the disease.

It has also been demonstrated that tissue factor (TF), an initiating factor for thrombus formation, is being excessively expressed on the cell surface and the extracellular interstitium in the plaque, and thus it is believed that the exposure of tissue factor (TF) to the blood resulting from the rupture of plaques is a major factor for thrombus formation.

Thus, there is a great need for the development of a novel drug for preventing or treating arterial thrombosis.

Thus, according to the fifth aspect of the present invention, there is provided a novel preventive or therapeutic agent for arterial thrombosis.

Percutaneous transluminal coronary angioplasty (PTCA) occupies an important position in the treatment of coronary heart diseases. But restenosis that occurs several months after the operation hinders the effectiveness of the treating method and thus is posing a problem. As a cause of restenosis, it is becoming increasingly clear, thrombus formation during the acute phase and the subacute phase resulting from the injuries to endothelial cells is important. The contact with the blood of tissue factor (TF) expressed by the injured endothelial cells and the smooth muscles and fibroblasts in the subendothelial tissue is important for thrombus formation. The cells in the blood vessel wall grow so as to cover the resulting thrombi and thereby narrow the area of the lumen in the blood vessel. The growth of the blood vessel tissue per se and the constriction of the blood vessel diameter also contribute to the narrowing of the area of the lumen in the blood vessel, and they provide a direct factor for restenosis. Thus, there is a great need for a novel drug that can prevent or treat restenosis.

Thus, according to the sixth aspect of the present invention, there is provided a novel preventive or therapeutic agent for diseases caused by the hypertrophy of vascular media.

DISCLOSURE OF THE INVENTION

After intensive and extensive research to resolve the above first problem, the inventors of the present invention have found out that by implanting, into an experimental animal, an animal cell capable of constantly expressing human tissue factor by introducing therein the gene of a human tissue factor (TF) and thereby increasing the concentration of human tissue factor in the animal, the hypercoagulable state of said animal can be maintained for a long period of time, and thereby have completed the present invention.

Thus, according to the first aspect, the present invention provides an experimental animal having implanted therein an animal cell to which the gene encoding human tissue factor (TF) or part thereof has been inserted and which is capable of expressing said gene, said animal being a non-human animal in which a hypercoagulable state persists for a long period of time.

The part of said human tissue factor is for example a human tissue factor that lacks the intracellular region. Said animal cell is preferably a mammalian cell. Said mammalian cell is preferably a human myeloma cell. Said animal is preferably a mouse. Said hypercoagulable state is indicated by at least one of the phenomena comprising an increase in the plasma concentration of human tissue factor, a decrease in platelets, a decrease in fibrinogen, an increase in the concentration of soluble fibrin monomer complex, and an increase in the concentration of thrombin-antithrombin III complex.

The present invention also provides a method of generating the above animal, wherein an animal cell to which the gene encoding human tissue factor (TF) or part thereof has been inserted and which is capable of expressing said gene is implanted to non-human animals and then an animal having a persistent hypercoagulable state is selected.

The present invention also provides a method of screening an anti-thrombotic agent which method comprises using the above animal.

After intensive and extensive research to resolve the above second problem, the inventors of the present invention have found out that an antibody (anti-human TF antibody, or sometimes referred to as anti-TF antibody) against human tissue factor can prevent the persistence of a hypercoagulable state.

Thus, according to the second aspect, the present invention provides a preventive or therapeutic agent for diseases having a persistent hypercoagulable state, said agent comprising an antibody against human tissue factor (human TF).

The above antibody is for example a polyclonal antibody. The above antibody is preferably a monoclonal antibody. The above antibody is preferably a recombinant antibody. The above antibody is preferably an altered antibody. The above altered antibody is preferably a chimeric antibody or a humanized antibody. The above humanized antibody is a humanized antibody of version b-b, i-b, or i-b2. The above antibody is for example an antibody modification. The above antibody modification is for example an antibody fragment Fab, $F(ab')_2$, or Fv, or a single chain Fv (scFv).

After intensive and extensive research to resolve the above third problem, the inventors of the present invention have found out that an antibody (anti-human TF antibody, or sometimes referred to as anti-TF antibody) against human tissue factor can prevent or treat a hypercoagulable state resulting from infections.

Thus, according to the third aspect, the present invention provides a preventive or therapeutic agent for a hypercoagulable state resulting from infections, said agent comprising an antibody against human tissue factor (human TF).

The above antibody is for example a polyclonal antibody. The above antibody is preferably a monoclonal antibody. The above antibody is preferably a recombinant antibody. The above antibody is preferably an altered antibody. The above altered antibody is preferably a chimeric antibody or a humanized antibody. The above humanized antibody is a humanized antibody of version b-b, i-b, or i-b2. The above antibody is for example an antibody modification. The above modified antibody is for example an antibody fragment Fab, $F(ab')_2$, or Fv, or a single chain Fv (scFv).

After intensive and extensive research to resolve the above fourth problem, the inventors of the present invention have found out that an antibody (anti-human TF antibody, or sometimes referred to as anti-TF antibody) against human tissue factor can prevent or treat venous thrombosis.

Thus, according to the fourth aspect, the present invention provides a preventive or therapeutic agent for venous thrombosis, said agent comprising an antibody against human tissue factor (human TF).

The above antibody is for example a polyclonal antibody. The above antibody is preferably a monoclonal antibody. The above antibody is preferably a recombinant antibody. The above antibody is preferably an altered antibody. The above altered antibody is preferably a chimeric antibody or a humanized antibody. The above humanized antibody is a humanized antibody of version b-b, i-b, or i-b2. The above antibody is for example an antibody modification. The above antibody modification is for example an antibody fragment Fab, $F(ab')_2$, or Fv, or a single chain Fv (scFv).

After intensive and extensive research to resolve the above fifth problem, the inventors of the present invention have found out that an antibody (anti-human TF antibody, or sometimes referred to as anti-TF antibody) against human tissue factor can prevent or treat arterial thrombosis.

Thus, according to the fifth aspect, the present invention provides a preventive or therapeutic agent for arterial thrombosis, said agent comprising an antibody against human tissue factor (human TF).

The above antibody is for example a polyclonal antibody. The above antibody is preferably a monoclonal antibody. The above antibody is preferably a recombinant antibody. The above antibody is preferably an altered antibody. The above altered antibody is preferably a chimeric antibody or a humanized antibody. The above humanized antibody is a humanized antibody of version b-b, i-b, or i-b2. The above antibody is for example an antibody modification. The above antibody modification is for example an antibody fragment Fab, F(ab')$_2$, or Fv, or a single chain Fv (scFv).

After intensive and extensive research to resolve the above sixth problem, the inventors of the present invention have found out that an antibody (anti-human TF antibody, or sometimes referred to as anti-TF antibody) against human tissue factor can prevent or treat diseases caused by the hypertrophy of vascular media.

Thus, according to the sixth aspect, the present invention provides a preventive or therapeutic agent for diseases caused by the hypertrophy of vascular media, said agent comprising an antibody against human tissue factor (human TF).

The above antibody is for example a polyclonal antibody. The above antibody is preferably a monoclonal antibody. The above antibody is preferably a recombinant antibody. The above antibody is preferably an altered antibody. The above altered antibody is preferably a chimeric antibody or a humanized antibody. The above humanized antibody is a humanized antibody of version b-b, i-b, or i-b2. The above antibody is for example an antibody modification. The above antibody modification is for example an antibody fragment Fab, F(ab')$_2$, or Fv, or a single chain Fv (scFv).

BRIEF EXPLANATION OF THE DRAWINGS

FIG. 14 is a graph showing changes in platelet counts with time in the mice that received the single administration of anti-human tissue factor antibody at 1 mg/kg or in the mice that received the 24-hour continuous administration of low molecular weight heparin at 601.5 IU/kg, 1900.3 IU/kg, or 6487.3 IU/kg using an osmotic pump on day 49 after implantation of tumor cells to which gene of human tissue factor has been introduced.

BEST MODE FOR CARRYING OUT THE INVENTION

Figure 1:
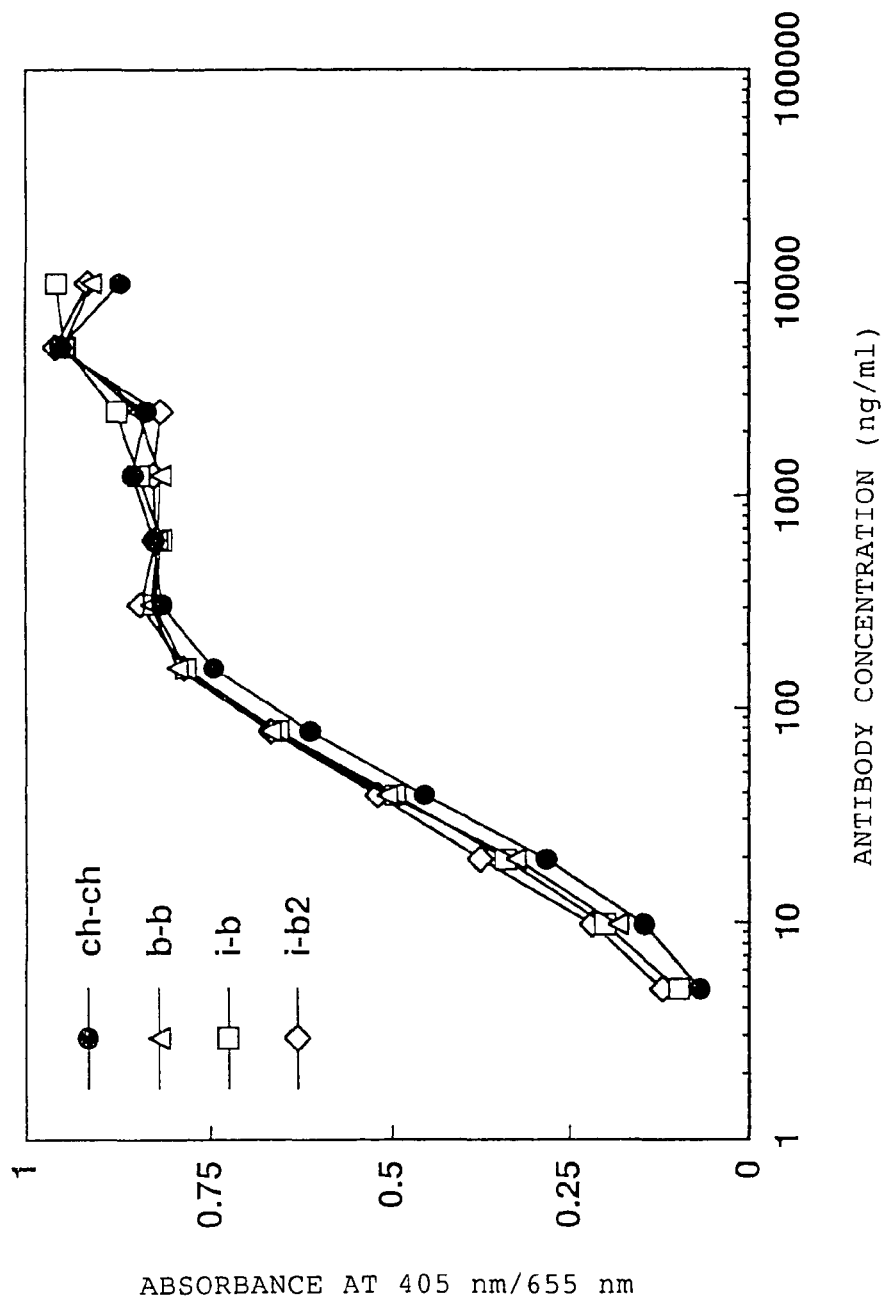
FIG. 1 is a graph that compares the antigen binding activity of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.

The gene that encodes human tissue factor (TF) for use in the first aspect of the present invention has already been cloned, and the base sequence and the amino acid sequence encoded thereby are also known (H. Morrissey et al., Cell, Vol. 50, p. 129-135 (1987)). The base sequence encoding the full-length human tissue factor and the corresponding amino acid sequence are set forth in SEQ ID NO: 103 and 104. According to the present invention, there may be used a gene encoding TF from which the intracellular region has been removed or a gene encoding the portion that retains the activity of initiating the blood coagulation system.

As a vector for introducing this gene into an animal cell and expressing it, any expression vector that functions in animal cells can be used, including, for example, pCOS1, pSV2-neo, pMAM-neo, and pSG5. In accordance with the present invention, a commonly used useful promoter, the human tissue factor gene, and a poly A signal, to 3'-end downstream thereof, can be functionally linked and can be expressed. As the promoter/enhancer, there can be mentioned human cytomegalovirus immediate early promoter/enhancer, viral promoters such as promoters of retrovirus, polyoma virus, adenovirus, and simian virus 40 (SV40), and promoters/enhancers derived from mammalian cells such as human elongation factor 1α (HEF1α). For expression vectors, as the replicator, there can be used those derived from SV40, polyoma virus, adenovirus and the like. Furthermore, for the expression vector can be contained as selectable markers the phosphotransferase APH (3') II or I (neo) gene, the thymidine kinase (TK) gene, the dihydrofolate reductase (dhfr) gene and the like.

As the method of introducing a gene into a cell, there can be used the electroporation method, the calcium phosphate method, the lipofection method and the like. As the cell for introducing the expression vector, any cell can be used as long as it can be grafted to an animal cell. For this purpose, various cultured cells may be used, including for example a mammalian cell such as a cultured cell derived from human, mice, rats, hamsters, and monkeys, with tumor cells being most preferred. As specific examples of the cell, there can be used a human myeloma cell line such as KPMM2 and ARH-77, a mouse leukemia cell line such as P815, P388, and L1210.

The experimental animals for use in the present invention are mammals other than the human and are preferably small experimental animals such as mice, rats, and hamsters with the mice being most preferred.

In accordance with the second aspect of the present invention, the hypercoagulable state means a physical condition induced by human TF, and give signs as a decrease in platelet counts and fibrinogen concentration, an increase in the concentration of soluble fibrin monomer complex (SFMC) and thrombin-antithrombin III complex (TAT).

Although the antibody used in the present invention may be either polyclonal antibody or monoclonal antibody provided it has a preventive or therapeutic effect on the persistence of a hypercoagulable state due to TF, monoclonal antibody is preferably. In addition, chimeric antibody, humanized antibody or single chain Fv and so forth based on monoclonal antibody can also be used, while humanized antibody is particularly preferable.

Although the antibody used in the third aspect of the present invention may be either polyclonal antibody or monoclonal antibody provided it has a preventive or therapeutic effect on the persistence of a hypercoagulable state due to TF, monoclonal antibody is preferable. In addition, chimeric antibody, humanized antibody or single chain Fv and so forth based on monoclonal antibody can also be used, while humanized antibody is particularly preferable.

Although the antibody used in the fourth aspect of the present invention may be either polyclonal antibody or monoclonal antibody provided it has a preventive or therapeutic effect on the persistence of a hypercoagulable state due to TF, monoclonal antibody is preferable. In addition, chimeric antibody, humanized antibody or single chain Fv and so forth based on monoclonal antibody can also be used, while humanized antibody is particularly preferable.

Although the antibody used in the fifth aspect of the present invention may be either polyclonal antibody or monoclonal antibody provided it has a preventive or therapeutic effect on the persistence of a hypercoagulable state due to TF, monoclonal antibody is preferable. In addition, chimeric antibody, humanized antibody or single chain Fv and so forth based on monoclonal antibody can also be used, while humanized antibody is particularly preferable.

Although the antibody used in the sixth aspect of the present invention may be either polyclonal antibody or monoclonal antibody provided it has a preventive or therapeutic effect on the persistence of a hypercoagulable state due to TF, monoclonal antibody is preferably. In addition, chimeric antibody, humanized antibody or single chain Fv and so forth based on monoclonal antibody can also be used, while humanized antibody is particularly preferable.

1. Anti-Human TF Antibody

The anti-human TF antibody used in the present invention may be of any origin, type (monoclonal or polyclonal) and form provided it has the effect of preventing or treating viral hemorrhagic fever.

The anti-human TF antibody used in the present invention can be obtained as polyclonal or monoclonal antibody using a known means. Monoclonal antibody of mammalian origin is particularly preferable as the anti-human TF antibody used in the present invention. Monoclonal antibody of mammalian origin includes that produced in hybridomas as well as that produced in a host transformed with an expression vector containing antibody gene by genetic engineering techniques. This antibody is an antibody that inhibits the induction of thrombus by human TF by binding with human TF.

2. Antibody-Producing Hybridoma

Monoclonal antibody-producing hybridoma can basically be produced in the following manner using known technology. Namely, using human TF or a portion (fragment) of it as sensitizing antigen, this is immunized in accordance with ordinary immunization methods, the resulting immunocytes are fused with known parent cells in accordance with ordinary cell fusion methods, and those cells that produce monoclonal antibody are screened in accordance with ordinary screening methods to produce monoclonal antibody.

More specifically, monoclonal antibody should be produced in the manner described below.

To begin with, human TF used as sensitizing antigen for antibody acquisition is obtained by expressing the TF gene/amino acid sequence disclosed in J. H. Morissey, et al., Cell, Vol. 50, p. 129-135 (1987). Namely, gene sequence coding for human TF is inserted into a known expression vector to transform suitable host cells followed by purifying the target human TF protein present in the host cells or culture supernatant using a known method. This method is described in Reference Example 1 of the present specification. Moreover, the human TF used as antigen can be used by extracting and purifying from a TF-containing biological material such as human placenta according to the method described in Reference Example 2.

Next, this purified human TF protein is used as sensitizing antigen. Alternatively, soluble TF from which the membrane permeating region of the C-terminal of human TF has been removed can be produced by, for example, genetic recombination, and this can also be used as sensitizing antigen.

Although there are no particular restrictions on the mammal that is sensitized with sensitizing antigen, it is preferable to select a mammal in consideration of compatibility with the parent cells used in cell fusion, typical examples of which include rodents such as mice, rats, hamsters, or rabbits and monkeys.

Immunization of animals with sensitizing antigen is performed in accordance with known methods. For example, as a typical immunization method, immunization is performed by injecting sensitizing antigen into the abdominal cavity or under the skin of the mammal. More specifically, sensitizing antigen is diluted to a suitable volume with phosphate-buffered saline (PBS) or physiological saline, and the resulting suspension is mixed with a suitable amount of ordinary adjuvant such as Freund's complete adjuvant as desired followed by emulsifying and administering in multiple doses to mammals every 4-21 days. In addition, a suitable carrier can also be used when immunizing with sensitizing antigen.

After immunizing the mammals in this manner and confirming that antibody has risen to the desired level in the serum, immunocytes are sampled from the mammals and applied to cell fusion. However, spleen cells are a particularly preferable example of immunocytes.

Mammalian myeloma cells are used for the other parent cells fused with the above immunocytes. Various known cell lines are used for these myeloma cells, preferable examples of which include P3 (P3x63Ag8.653) (Kearney, J. F. et al., J. Immunol. (1979) 123, 1548-1550), P3x63Ag8U.1 (Yelton, D. E. et al., Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), F0 (de St. Groth, S. F. and Scheidegger, D. J., J. Immunol. Methods (1980) 35, 1-21), S194 (Trowbridge, I. S., J. Exp. Med. (1978) 148, 313-323) and R210 (Galfre, G. et al., Nature (1979) 277, 131-133).

Cell fusion of the above immunocytes and myeloma cells can basically be carried out in compliance with known methods such as the method of Milstein, et al. (Galfre G. and Milstein, C., Methods Enzymol. (1981) 73, 3-46).

More specifically, the above cell fusion is carried out, for example, in ordinary nutrient culture media in the presence of cell fusion promoter. Examples of cell fusion promoters used include polyethylene glycol (PEG) and Sendai virus (HVJ). Moreover, an assistant such as dimethylsulfoxide can be added to further enhance fusion efficiency as desired.

The usage ratio of immunocytes and myeloma cells can be set arbitrarily. For example, the number of immunocytes is preferably 1-10 times the number of myeloma cells. Examples of culture media used in the above cell fusion include RPMI1640 culture medium, MEM culture medium and other ordinary culture media used in this type of cell culturing that is suitable for growth of the above myeloma cell lines. Moreover, serum supplement such as fetal calf serum (FCS) can also be used in combination with the above media.

Cell fusion is carried out by adequately mixing prescribed amounts of the above immunocytes and myeloma cells in the above culture media, adding PEG solution (for example, that having a molecular weight of about 1000-6000) warmed in advance to about 37° C. at a concentration of usually 30-60% (w/v) and mixing to form the target fused cells (hybridoma). Subsequently, a suitable amount of culture media is sequentially added, and cell fusion agents and so forth undesirable for hybridoma growth are removed by repeated removal of supernatant by centrifugation.

The hybridoma obtained in this manner is selected by culturing in an ordinary selective culture medium such as HAT culture medium (culture medium containing hypoxanthine, aminopterin and thymidine). Culturing in the above HAT culture medium is continued for an adequate amount of time (normally from several days to several weeks) for killing cells other than the target hybridoma cells (non-fused cells). Next, routine critical dilution is performed followed by screening for hybridoma that produces the target antibody and monocloning.

In addition, besides obtaining the above hybridoma by immunizing animals other than humans with antigen, a desired human antibody having binding activity to human TF can be obtained by sensitizing human lymphocytes to human TF in vitro, and fusing the sensitized lymphocytes with human myeloma cells such as myeloma cell line U266 having permanent mitotic ability (refer to Japanese Examined Patent Publication No. 1-59878). Moreover, human antibody to antihuman TF may also be acquired from attenuated cells by administering human TF serving as antigen to transgenic animals having all or a portion of the human antibody gene repertoire, acquiring anti-human TF antibody-producing cells and attenuating those cells (refer to International Unexamined Patent Application No. WO 94/25585, WO 93/12227, WO 92/03918, WO 94/02602, WO 96/34096 and WO 96/33735).

Hybridoma that produces monoclonal antibody obtained in this manner can be sub-cultured in ordinary culture media, and can be stored for a long period of time in liquid nitrogen.

In order to acquire monoclonal antibody from said hybridoma, said hybridoma is cultured in accordance with routine methods followed by obtaining the culture supernatant, or the hybridoma can be administered to a compatible mammal to proliferate in that mammal followed by obtaining in the form of the ascites. The former method is suitable for obtaining highly pure antibody, while the latter method is suitable for large volume production of antibody.

An example of monoclonal antibody production is specifically described in Reference Example 2. In this example, six types of monoclonal antibodies referred to as ATR-2, 3, 4, 5, 7 and 8 are obtained. Although all of these can be used in the present invention, ATR-5 is particularly preferable.

3. Recombinant Antibody

In the present invention, recombinant antibody produced using genetic recombination technology by cloning antibody gene from hybridoma, incorporating in a suitable vector and introducing this into a host can be used as monoclonal antibody (refer to, for example, Vandamme, A. M. et al., Eur. J. Biochem. (1990) 192, 767-775).

More specifically, mRNA that codes for the variable region (V) of anti-human TF antibody is isolated from hybridoma that produces anti-human TF antibody. Isolation of mRNA is carried out by a known method such as guanidine ultracentrifugation (Chirgwin, J. M. et al., Biochemistry (1979) 18, 5294-5299) or the AGPC method (Chomczynski, P. and Sacchi, N., Anal. Biochem. (1987) 162, 156-159) to prepare total RNA, followed by preparation of the target mRNA using an mRNA Purification Kit (Pharmacia). In addition, mRNA can also be prepared directly by using the QuickPrep mRNA Purification Kit (Pharmacia).

cDNA of the antibody V region is synthesized from the resulting mRNA using reverse transcriptase. Synthesis of cDNA is carried out using the AMV Reverse Transcriptase First-strand cDNA Synthesis Kit (Seikagaku Co.). In addition, synthesis and amplification of cDNA can also be carried out by using the 5'-Ampli FINDER RACE Kit (Clontech) and the 5'-RACE method using PCR (Frohman, M. A. et al., Proc. Natl. Acad. Sci. USA (1988) 85, 8998-9002, Belyaysky, A. et al., Nucleic Acids Res. (1989) 17, 2919-2932).

The target DNA fragment is purified from the resulting PCR product and linked with vector DNA. Moreover, a recombinant vector is produced from this, introduced into *Escherichia coli* and so forth, and colonies are selected to prepare the desired recombinant vector. The base sequence of the target DNA is then confirmed by a known method such as deoxyribonucleotide chain termination.

After obtaining DNA that codes for the V region of the target anti-human TF antibody, this is incorporated into an expression vector containing DNA that codes for the desired antibody constant region (C region).

In producing the anti-human TF antibody used in the present invention, an antibody gene is incorporated into an expression vector under the control of an expression control region such as an enhancer or promoter. Next, the host cells are transformed by this expression vector to express antibody.

Expression of antibody gene may be carried out either by separately incorporating DNA that codes for antibody heavy chain (H chain) or light chain (L chain) into expression vectors and then simultaneously transforming the host cells, or by incorporating DNA that codes for H chain and L chain into a single expression vector and transforming the host cells (refer to the publication of WO 94/11523).

In addition, transgenic animals can also be used in addition to the above host cells to produce recombinant antibody. For example, recombinant antibody is produced in the form of a fused gene by inserting antibody gene at an intermediate location of a gene that codes for protein characteristically produced in breast milk. A DNA fragment containing fused gene into which antibody gene has been inserted is injected into a goat embryo, and this embryo is then introduced into a female goat. The desired antibody is obtained from the mother's milk produced by the transgenic goat born from the goat that received the embryo, or its offspring. In addition, a suitable hormone may be used in the transgenic goat to increase the amount of breast milk containing the desired antibody produced by that transgenic goat (Ebert, K. M. et al., Bio/Technology (1994) 12, 699-702).

An example of a production method of recombinant antibody is specifically described in Reference Example 3.

4. Altered Antibody

In the present invention, in addition to the above-mentioned antibodies, genetic recombinant antibody that has been artificially altered for the purpose of decreasing heterogenic antigenicity with respect to humans can also be used, examples of which include chimeric antibody and humanized antibody. These altered antibodies can be produced using known methods.

Chimeric antibody is obtained by linking DNA that codes for the antibody V region in the manner described above and DNA that codes for human antibody C region, incorporating this in an expression vector and introducing into a host to produce antibody. Chimeric antibody that is useful in the present invention can be obtained using this known method.

Humanized antibody is also referred to as reshaped human antibody. This is the result of transplanting the complementarity determining region (CDR) of antibody of a mammal other than a human, such as mouse antibody, into the complementarity determining region of human antibody, and typical genetic recombination techniques are known for this (refer to European Unexamined Patent Publication No. EP 125023 and WO 96/02576).

More specifically, a DNA sequence designed so as to link the CDR of mouse antibody with the framework region (FR) of human antibody is synthesized by PCR using as primer a plurality of oligonucleotides prepared so as to have a portion that overlaps the terminal regions of both CDR and FR (refer to the method described in the publication of WO 98/13388).

A region in which the complementarity determining region forms a satisfactory antigen binding site is selected for the framework region of the human antibody that is linked by way of CDR. The amino acids of the framework region in the variable region of the antibody may be substituted as necessary so that the complementarity determining region of reshaped human antibody forms an appropriate antigen binding site (Sato, K. et al., Cancer Res. (1993) 53, 851-856).

The C region of human antibody is used for the C region of chimeric antibody and humanized antibody, and for example, Cγ1, Cγ2, Cγ3 and Cγ4 can be used in the H chain, while Cκ and Cλ can be used in the L chain. In addition, human antibody C region may be modified to improve the stability of the antibody or its production.

Chimeric antibody is composed of the variable region of antibody originating in a mammal other than humans and the constant region of human antibody. On the other hand, humanized antibody is composed of the complementarity determining region of an antibody originating in a mammal other than humans and the framework region and C region of human antibody. Since humanized antibody has decreased antigenicity in the human body, it is useful as an effective ingredient of the therapeutic agent of the present invention.

The production method of chimeric antibody is specifically described in Reference Example 4.

In addition, the production method of humanized antibody is specifically described in Reference Example 5. In this reference example, versions a, b, c, d, e, f, g, h, i, j, b1, d1, b3 and d3 having the amino acid sequences shown in Tables 1 and 2 were used as the humanized heavy chain (H chain) variable region (V region).

TABLE 1

| | Amino Acid Sequences of H Chain V Region | | | |
|---|---|---|---|---|
| | FR1 | | FR2 | CDR2 |
| | 1 2 3<br>12345678901234567890123456789012345678901234567890 | CDR1<br>12345 | 4 5<br>67890123456789 | 6<br>012A3456789012345 |
| L39130(a) | QVQLLESGAVLARPGTSVKISCKASGFNIK | DYYMH | WVKQRPGQGLEWIG | GNDPANGHSMYDPKFQG |
| Z34963(b) | ------------------------------ | ----- | -------------- | ----------------- |

TABLE 1-continued

Amino Acid Sequences of H Chain V Region

| | FR1 | | | CDR1 | FR2 | | CDR2 |
|---|---|---|---|---|---|---|---|
| | 1 | 2 | 3 | | 4 | 5 | 6 |
| | 1234567890 | 1234567890 | 1234567890 | 12345 | 67890 | 123456789 | 012A3456789012345 |
| M30885(c) | ------------------------------ | | | ----- | -------------- | | ----------------- |
| M62723(d) | ------------------------------ | | | ----- | -------------- | | ----------------- |
| Z80844(e) | ------------------------------ | | | ----- | -------------- | | ----------------- |
| L04345(f) | ------------------------------ | | | ----- | -------------- | | ----------------- |
| S78322(g) | ------------------------------ | | | ----- | -------------- | | ----------------- |
| Z26827(h) | ------------------------------ | | | ----- | -------------- | | ----------------- |
| U95239(i) | ------------------------------ | | | ----- | -------------- | | ----------------- |
| L03147(j) | ------------------------------ | | | ----- | -------------- | | ----------------- |
| P01742(b1) | ------------------------------ | | | ----- | --R-A-------M- | | ----------------- |
| P01742(d1) | ------------------------------ | | | ----- | --R-A-------M- | | ----------------- |
| Z80844(b3) | ------------------------------ | | | ----- | --R-A--------- | | ----------------- |
| Z80844(d3) | ------------------------------ | | | ----- | --R-A--------- | | ----------------- |

TABLE 2

Amino Acid Sequences of H Chain V Region (cont. from Table 1)

| | FR3 | | | CDR3 | FR4 |
|---|---|---|---|---|---|
| | 7 | 8 | 9 | 10 | 11 |
| | 6789012345 | 6789012ABC | 345678901234 | 56789012 | 34567890123 |
| L39130(a) | RAKLTAATSA | SIAYLEFSSL | TNEDSAVYYCAR | DSGYAMDY | WGQGTLVTVSS |
| Z34963(b) | -VTI--D-- | TNT--M-L--- | RS--T-I----- | -------- | ----------- |
| M30885(c) | -VTMLVD-- | KNQFS-RL-- | V-AA-T------ | -------- | ----------- |
| M62723(d) | -VTI--DE- | T-T--M-L-- | -RS------F--- | -------- | ----------- |
| Z80844(e) | -VSI--DE- | TK---M-LN- | -RS--T---F--- | -------- | ----------- |
| L04345(f) | -VTI--DT- | T-T--M-LR- | -RSD-T------ | -------- | ----------- |
| S78322(g) | K-T---DE- | S-T--MQL-- | -RS------S--- | -------- | ----------- |
| Z26827(h) | -VTMS-DK- | S-A---QWT- | -KAS-T-I-F--- | -------- | ----------- |
| U95239(i) | -VTI--D-- | T-TVFM-L-- | -RS--T------ | -------- | ----------- |
| L03147(j) | -VTF--D-- | -NT--M-LR- | -RSA-T------ | -------- | ----------- |
| P01742(b1) | -VTI--D-- | TNT--M-L-- | -RS--T-I----- | -------- | ----------- |
| P01742(d1) | -VTI--DE- | T-T--M-L-- | -RS------F--- | -------- | ----------- |
| Z80844(b3) | -VTI--D-- | TNT--M-L-- | -RS--T-I----- | -------- | ----------- |
| Z80844(d3) | -VTI--DE- | T-T--M-L-- | -RS------F--- | -------- | ----------- |

In addition, versions a, b, c, b1 and b2 having the amino acid sequences shown in Table 3 were used as the humanized light chain (L chain) V region.

As a result of evaluating antigen binding ability and TF neutralization activity by combining the above various versions of H chain V region and the various versions of L chain

TABLE 3

Amino Acid Sequences of L Chain V Region

| | FR1 | | CDR1 | FR2 | CDR2 |
|---|---|---|---|---|---|
| | 1 | 2 | 3 | 4 | 5 |
| | 1234567890 | 1234567890123 | 45678901234 | 567890123456789 | 0123456 |
| Z37332(a) | DIQMTQSPSS | LSASVGDRVTITC | KASQDIKSFLS | WYQQKPGKAPKLLIY | YATSLAD |
| S68699(b) | ---------- | ------------- | ----------- | --------------- | ------- |
| P01607(c) | ---------- | ------------- | ----------- | --------------- | ------- |
| S65921(b1) | ---------- | ------------- | ----------- | -F------S--T--- | ------- |
| X93625(b2) | ---------- | ------------- | ----------- | ------E----S--- | ------- |

| | FR3 | | | CDR3 | FR4 |
|---|---|---|---|---|---|
| | 6 | 7 | 8 | 9 | 10 |
| | 7890123456 | 78901234567 | 89012345678 | 901234567 | 8901234567 |
| Z37332(a) | GVPSRFSGSG | SGTDFTLTISS | LQPEDFATYYC | LQHGESPYT | FGGGTKVEIK |
| S68699(b) | ---------- | ----Y------ | ----------- | --------- | ---------- |
| P01607(c) | ---------- | ----Y------ | -----I----- | --------- | ---------- |
| S65921(b1) | ---------- | ----Y------ | ----------- | --------- | ---------- |
| X93625(b2) | ---------- | ----Y------ | ----------- | --------- | ---------- |

Figure 2:
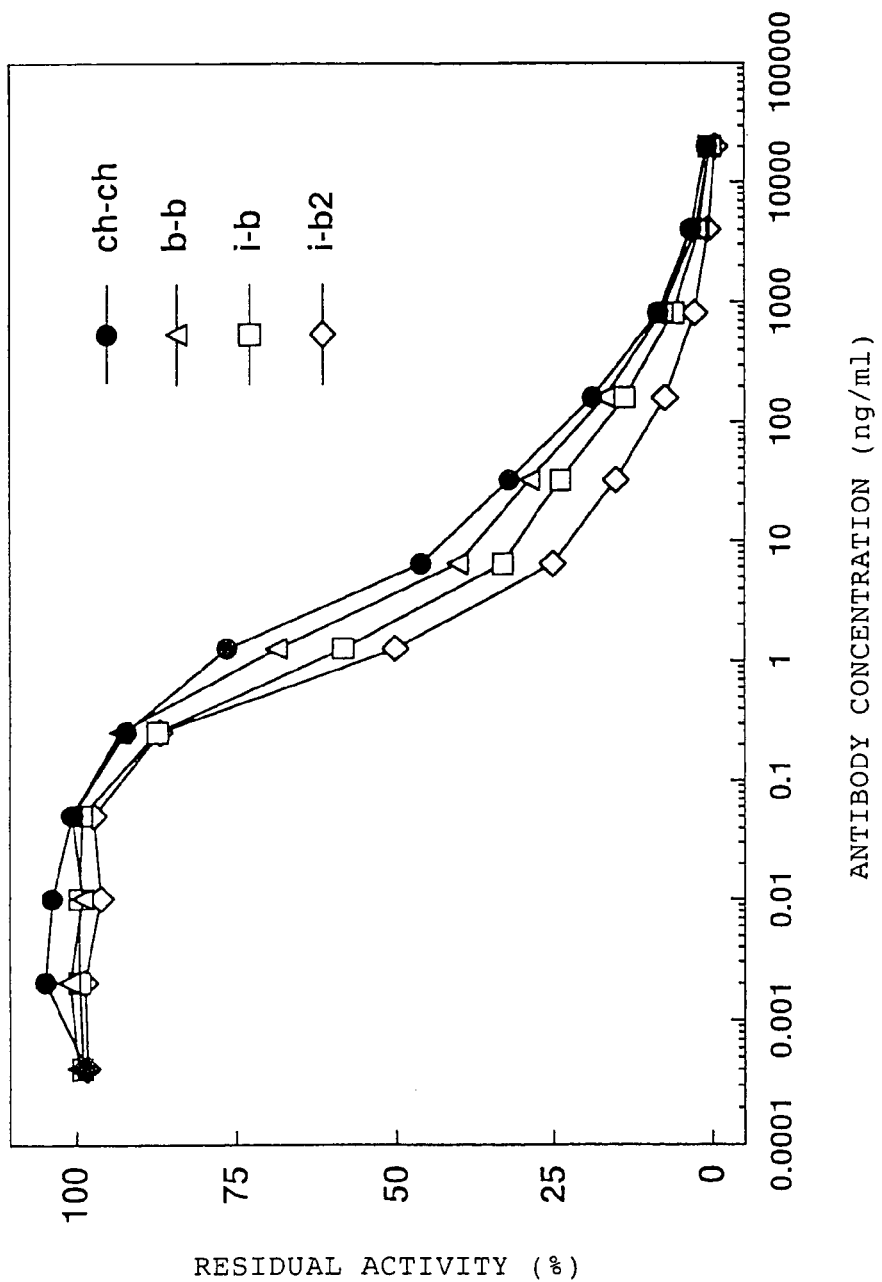
FIG. 2 is a graph that compares the activity of neutralizing human TF (the activity of TF to inhibit the production of Factor Xa) of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.
Figure 3:
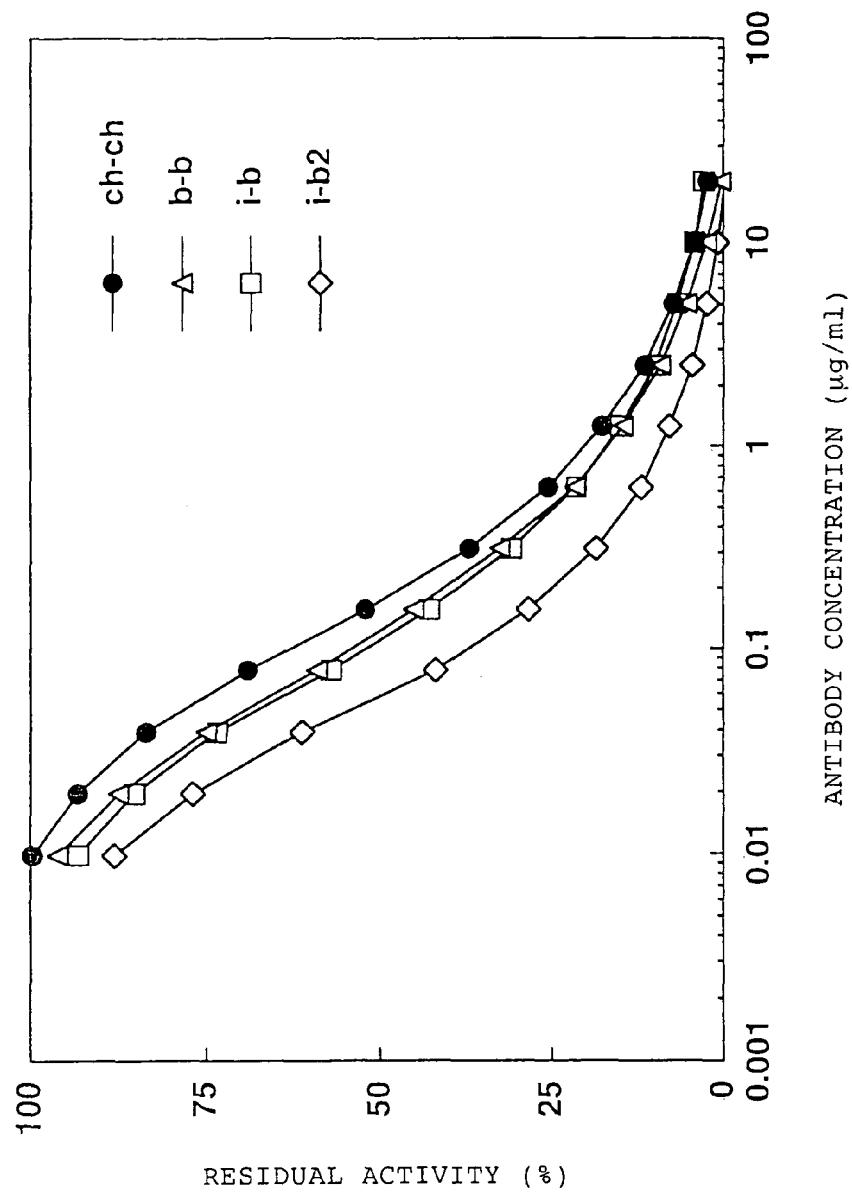
FIG. 3 is a graph that compares the activity of neutralizing human TF (the activity of TF to inhibit the production of Factor X) of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.
Figure 4:
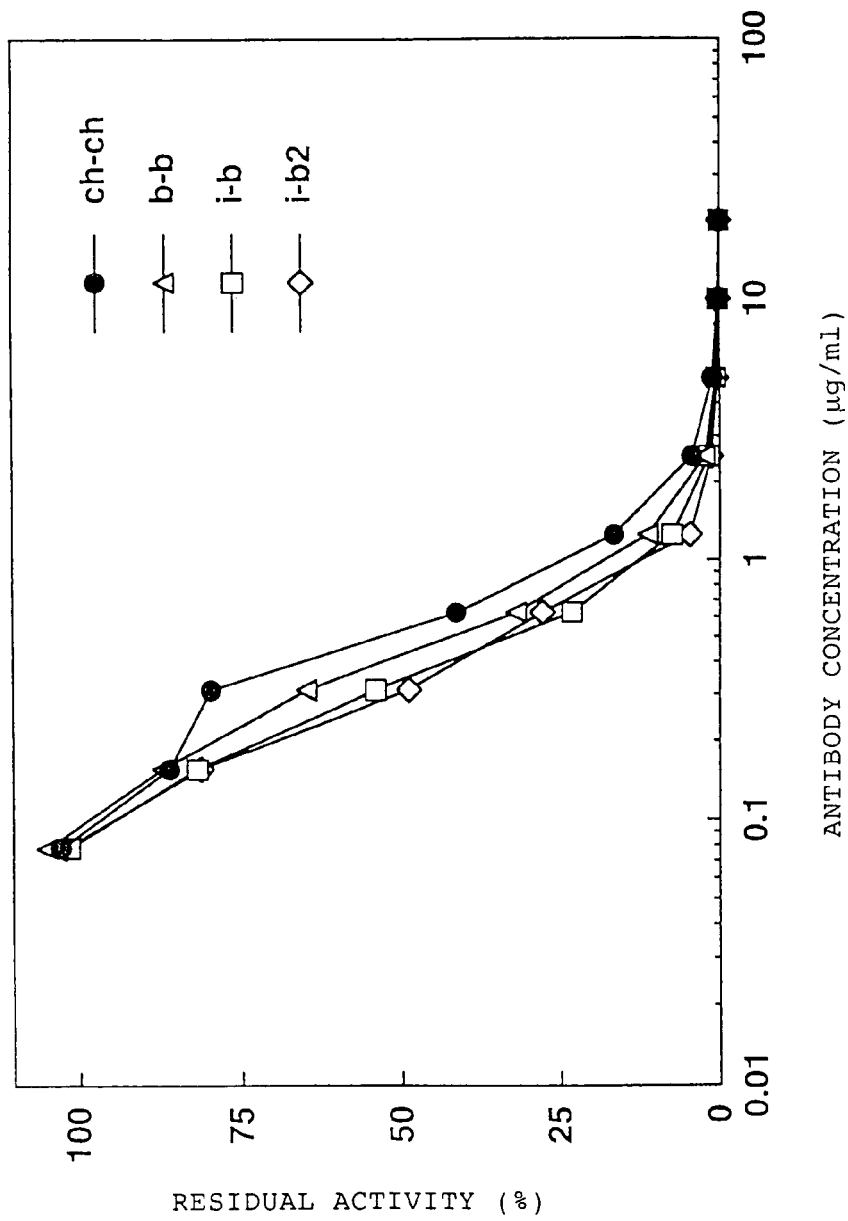
FIG. 4 is a graph that compares the activity of neutralizing human TF (the activity of TF to inhibit plasma coagulation) of a H chain chimeric/L chain chimeric antibody, a H chain humanized version b/L chain humanized version b antibody, a H chain humanized version i/L chain humanized version b antibody, and a H chain humanized version i/L chain humanized version b2 antibody.

V region, as described in Reference Examples 6 and 7, in the case of indicating as "H chain V region version"—"L chain V region version", the combinations of "b-b", "i-b" and "i-b2" exhibited particularly high activity. Furthermore, the antigen binding ability of these humanized antibodies is shown in FIG. 1, human TF neutralization activity (TF Factor Xa production inhibitory activity) is shown in FIG. 2, human TF neutralization activity (Factor X binding inhibitory activity) is shown in FIG. 3, and human TF neutralization activity (TF plasma coagulation inhibitory activity) is shown in FIG. 4.

5. Modified Antibody Substances

The antibody used in the present invention may be an antibody fragment or modified antibody substance provided it binds to human TF and inhibits human TF activity. For example, examples of antibody fragments include single chain Fv (scFv) in which Fab, F(ab')$_2$, Fv or H chain or L chain Fv is linked with a suitable linker.

More specifically, either antibody is treated with an enzyme such as papain or pepsin to produce antibody fragments, or a gene is constructed that codes for these antibody fragments, after which a fragment is inserted into an expression vector and expressed in a suitable host (refer to, for example, Co, M. S. et al., J. Immunol. (1994) 152, 2968-2976, Better, M. & Horowitz, A. H., Methods in Enzymology (1989) 178, 476-496, Plueckthun, A. & Skerra, A., Methods in Enzymology (1989) 178, 497-515, Lamoyi, E., Methods in Enzymology (1986) 121, 652-663, Rousseaux, J. et al., Methods in Enzymology (1986) 121, 663-669, and Bird, R. E. et al., TIBTECH (1991) 9, 132-137).

scFv is obtained by linking antibody H chain V region and L chain V region. In this scFv, the H chain V region and L chain V region are linked by means of a linker, and preferably by means of a peptide linker (Huston, J. S. et al., Proc. Natl. Acad. Sci., USA (1988) 85, 5879-5883). The H chain V region and L chain V region in scFv may be of any origin described as antibody in the present specification. An arbitrary single chain peptide comprised of, for example, 12-19 amino acid residues is used for the peptide linker that links the V regions.

DNA that codes for scFv is obtained by using as template the portion of DNA coding for H chain or H chain V region and DNA coding for L chain or L chain V region of the above antibody that codes for the entire or desired amino acid sequence of those sequences, amplifying by PCR using a primer pair that defines both of its ends, and combining and amplifying DNA that codes for a peptide linker portion and primer pair defined such that both of its ends are linked with each H chain and L chain.

In addition, once DNA that codes for scFv is produced, an expression vector that contains them and a host that is transformed by said expression vector can be obtained in accordance with routine methods, and scFv can be obtained in accordance with routine methods by using that host.

These antibody fragments can be produced from a host by acquiring the gene in the same manner as previously described and expressing that gene. The term "antibody" in the present invention includes these antibody fragments.

Anti-human TF antibody coupled with various molecules such as polyethylene glycol can also be used as modified antibody substances. These modified antibody substances are also included in the "antibody" of the present invention. These modified antibody substances can be obtained by performing chemical modification on the resulting antibody. Furthermore, antibody modification methods have already been established in this field.

6. Expression and Production of Recombinant Antibody or Altered Antibody

Antibody gene constructed in the manner previously described can be expressed and acquired by known methods. In the case of mammalian cells, antibody gene can be expressed by functionally coupling a commonly used useful promoter, antibody gene to be expressed and a poly A signal downstream from its 3'-side. An example of a promoter/enhancer is human cytomegalovirus immediate early promoter/enhancer.

In addition, other examples of promoter/enhancer that can be used to express antibody used in the present invention include virus promoter/enhancer such as retrovirus, poliovirus, adenovirus, and simean virus 40 (SV40), as well as promoter/enhancer originating in mammalian cells such as human elongation factor 1α (HEF1α).

Gene expression can be carried out easily according to the method of Mulligan, et al. (Nature (1979) 277, 108-114) in the case of using SV40 promoter/enhancer, or according to the method of Mizushima, et al. (Nucleic Acid Res. (1990) 18, 5322) in the case of using HEF1α promoter/enhancer.

In the case of *E. coli*, said gene can be expressed by functionally coupling a commonly used useful promoter, signal sequence for antibody secretion and the antibody gene to be expressed. Examples of promoters include lacz promoter and araB promoter. Gene can be expressed according to the method of Ward, et al. (Nature (1989) 341, 544-546; FASEB J. (1992) 6, 2422-2427) in the case of using lacz promoter, or according to the method of Better, et al. (Science (1988) 240, 1041-1043) in the case of using araB promoter.

The pelB signal sequence (Lei, S. P. et al., J. Bacteriol. (1987) 169, 4379-4383) should be used as the signal sequence for antibody secretion in the case of producing in periplasm of *E. coli*. After isolating the antibody produced in periplasm, the antibody is used after suitably refolding the antibody structure.

Replication origins originating in SV40, poliovirus, adenovirus or bovine papilloma virus (BPV) and so forth can be used as replication origins. Moreover, in order to amplify the number of gene copies in host cell systems, the expression vector can contain as selection marker aminoglycoside transferase (APH) gene, thymidine kinase (TK) gene, *E. coli* xanthine guanine phosphoribosyl transferase (Ecogpt) gene or dihydrofolate reductase (dhfr) gene.

An arbitrary expression system, such as a eucaryotic cell or procaryotic cell system, can be used to produce the antibody used in the present invention. Examples of eucaryotic cells include established mammalian cell systems, insect cell systems and fungal cells such as mold cells and yeast cells, while examples of procaryotic cells include bacterial cells such as *E. coli* cells.

The antibody used in the present invention is preferably expressed in mammalian cells such as CHO, COS, myeloma, BHK, Vero and HeLa cells.

Next, the transformed host cells are cultured in vitro or in vivo to produce the target antibody. Culturing of host cells is carried out in accordance with known methods. For example, DMEM, MEM, RPMI1640 or IMDM can be used for the culture medium, and a serum supplement such as fetal calf serum (FCS) can be used in combination with the above media.

7. Antibody Isolation and Purification

Antibody expressed and produced as described above can be isolated from cells or host animal and purified until homogeneous. Isolation and purification of antibody used in the present invention can be carried out using an affinity column. Examples of columns using a protein A column include Hyper D, POROS and Sepharose F.F. (Pharmacia). In addition, isolation and purification methods used with ordinary proteins should be used, and there are no restrictions whatsoever on these methods. For example, antibody can be isolated and purified by suitably selecting and combining, in addition to above affinity columns, a chromatography column, filter, ultrafiltration, salting out or dialysis and so forth (Antibodies: A Laboratory Manual, Ed Harlow and David Lane, Cold Spring Harbor Laboratory, 1988).

8-1. Measurement of the Inhibitory Effect on the Persistence of a Hypercoagulable State In order to study the efficacy of prevention or treatment of the present invention for diseases having a chronic hypercoagulable state, a novel animal model is required, and the details of the evaluation method are described in the specification of the patent application entitled "An animal model of a chronic hypercoagulable state and a method of generating the same" by the same applicant as this invention. Specific examples of the evaluation method are described as Example 1 in this specification.

Figure 11:
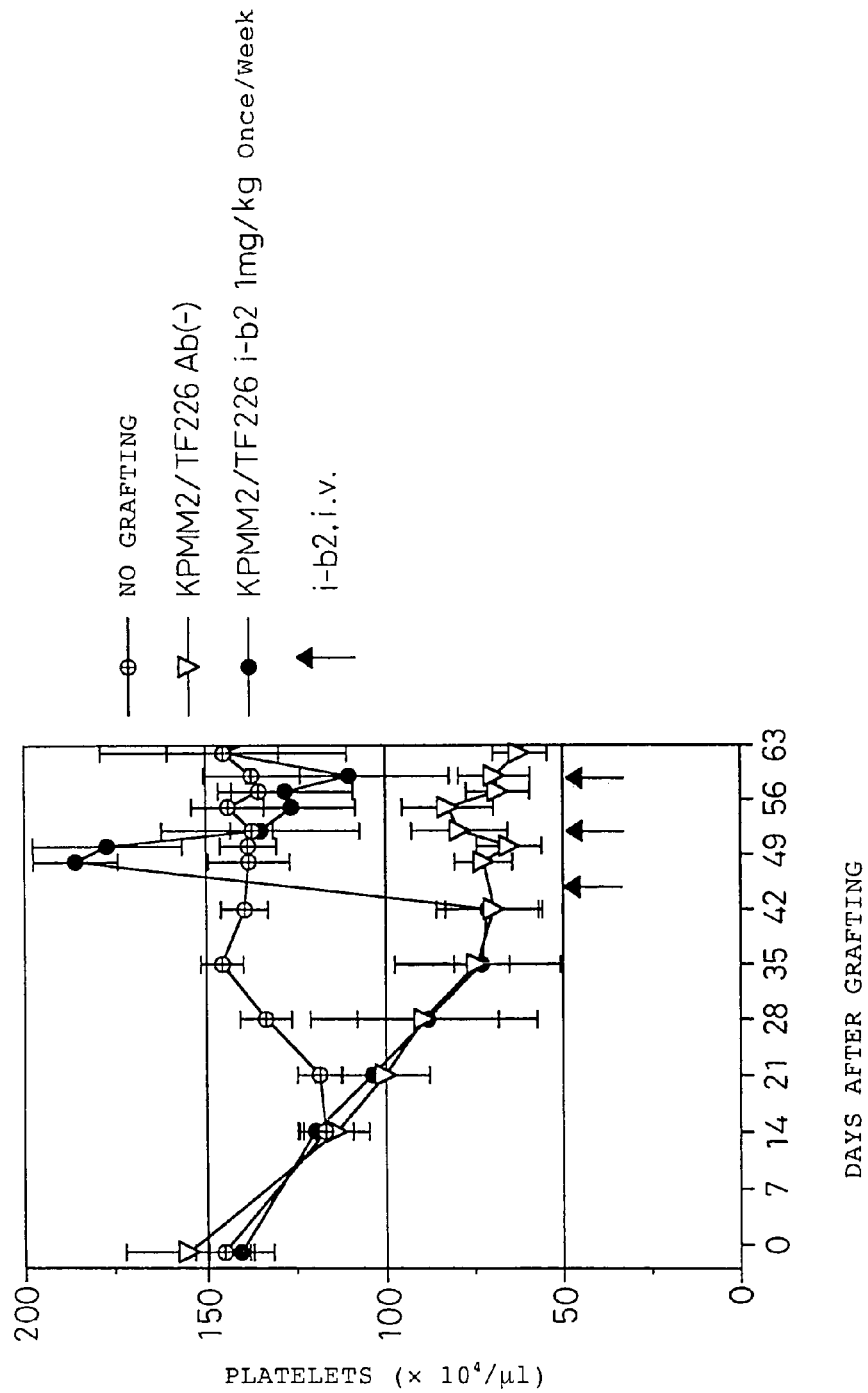
FIG. 11 is a graph showing changes in platelet counts with time in the mice that are administered anti-human tissue factor antibody at 1 mg/kg once weekly for three weeks from day 45 after implantation of tumor cells to which gene of human tissue factor has been introduced.
Figure 12:
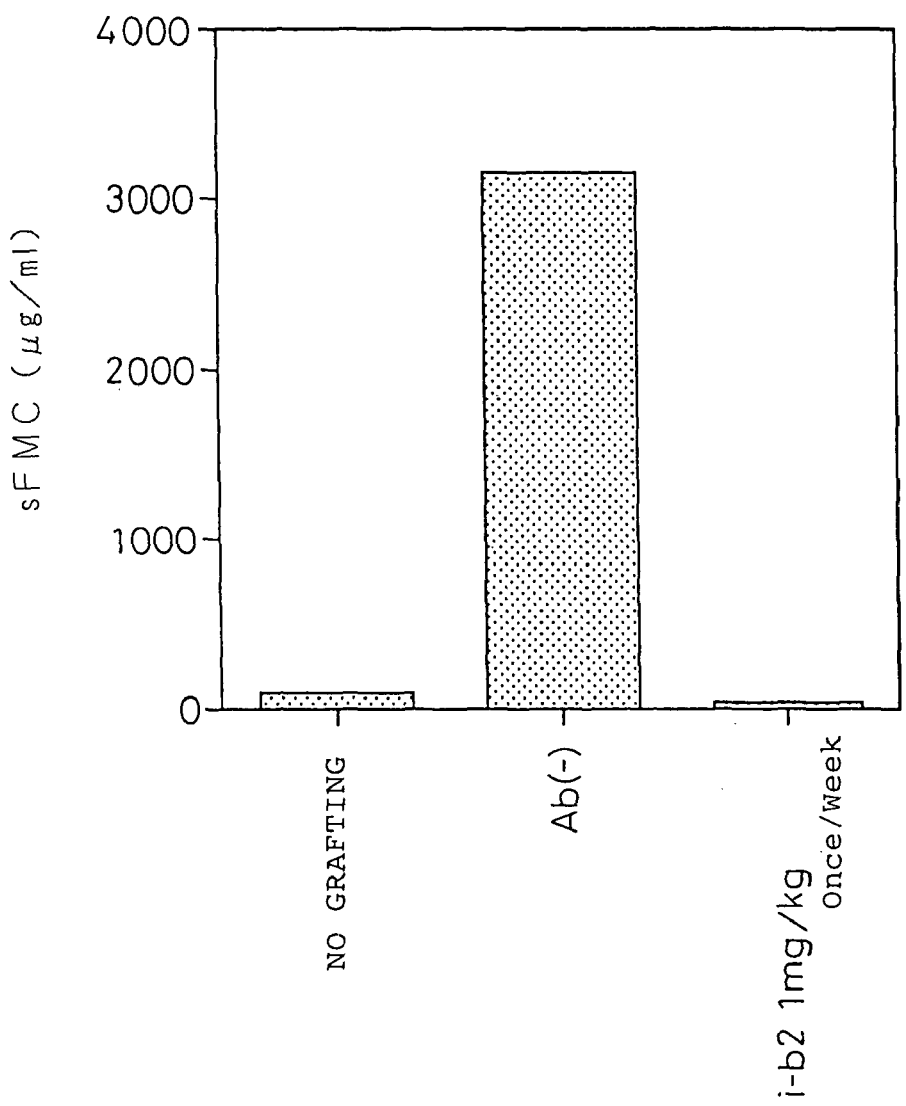
FIG. 12 is a graph showing the plasma concentration of soluble fibrin monomer complex (sFMC) on day 6 after the final administration of anti-human tissue factor antibody in the mice that are administered said antibody at 1 mg/kg once weekly for three weeks from day 45 after implantation of tumor cells to which gene of human tissue factor has been introduced.
Figure 13:
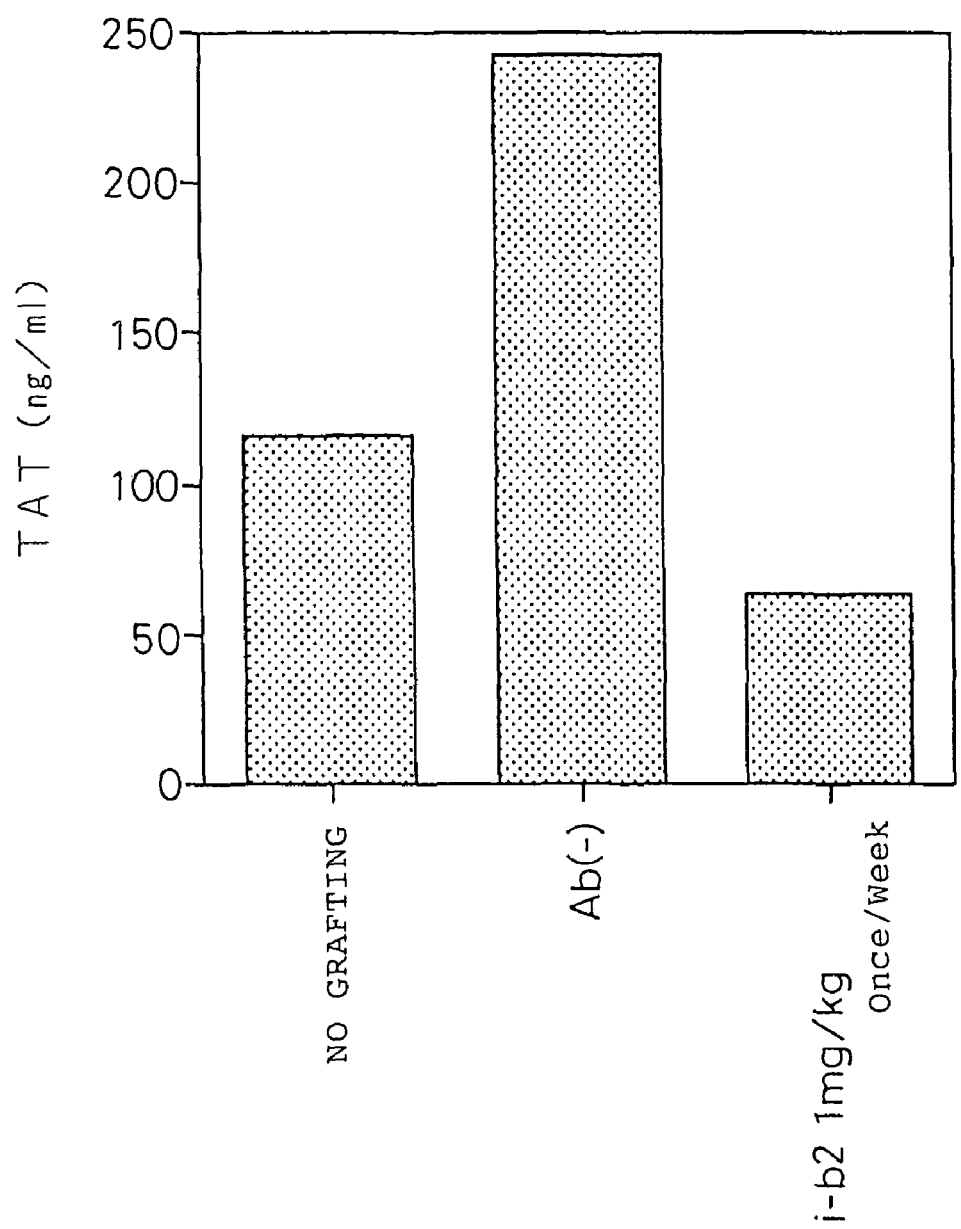
FIG. 13 is a graph showing the plasma concentration, of thrombin-antithrombin III complex (TAT) on day 6 after the final administration of anti-human tissue factor antibody in the mice that are administered said antibody at 1 mg/kg once weekly for three weeks from day 45 after implantation of tumor cells to which gene of human tissue factor has been introduced.

The result of the experiment that used the above humanized anti-human TF antibody version "i-b2" is shown in Example 2 and FIGS. 11 to 13. According to this experiment, in the animal model system shown in Example 1, after the platelet count of the mice that were implanted with the tumor cell containing the human TF gene decreased to about half of that of the mice that were not implanted with the same (5 to 6 weeks after implantation), 1 mg/kg of the humanized anti-human TF antibody version "i-b2" was repeatedly administered intravenously once a week, with a result that the platelet count was maintained at a level equal to that in the mice that were not implanted with the tumor cell till the end of the experiment, i.e., three weeks after the start of the administration.

The administration of the humanized anti-human TF antibody of the present invention suppressed the increase in the concentrations of soluble fibrin monomer complex (sFMC) and thrombin-antithrombin III complex (TAT). The result confirmed that the administration of anti-human TF antibody of the present invention prevents the persistence of a hypercoagulable state and maintains a normal state.

8-2. Confirmation of the Therapeutic Effect on a Hypercoagulable State Resulting from Infections An elongation of prothrombin time, a decrease in the plasma concentration of fibrinogen, an increase in the serum concentration of fibrin degradation products, and the like can be ascribed to the hypercoagulable state. The administration of anti-human TF antibody of the present invention suppressed the elongation of prothrombin time, the decrease in plasma concentration of fibrinogen, and the increase in the serum concentration of fibrin degradation products induced by the continuous infusion of LPS. This result demonstrates that the anti-human TF antibody of the present invention has a preventive and/or therapeutic effect on the hypercoagulable state resulting from infections.

In Example 3, this effect is described in detail.

8-3. Confirmation of the Preventive and/or Therapeutic Effect on Venous Thrombosis In Example 4, it is described in detail that the anti-human TF antibody of the present invention has a preventive and/or therapeutic effect on venous thrombosis.

8-4. Confirmation of the Preventive and/or Therapeutic Effect on Arterial Thrombosis In Example 5, it is described in detail that the anti-human TF antibody of the present invention has a preventive and/or therapeutic effect on arterial thrombosis.

8-5. Confirmation of the Preventive and/or Therapeutic Effect on Diseases Resulting from the Medial Thickening of Blood Vessels In Example 6, it is described in detail that the anti-human TF antibody of the present invention has a preventive and/or therapeutic effect on diseases resulting from the medial thickening of blood vessels.

9. Method of Administration and Formulation

The therapeutic agent of the present invention is used for the purpose of preventing, treating or improving diseases having a persistent hypercoagulable state, a hypercoagulable state resulting from infections, venous thrombosis, arterial thrombosis, and diseases resulting from the hypertrophy of vascular media.

Effective dosage per administration is selected from the range of 0.001 mg to 1000 mg/kg body weight. Alternatively, the dosage of 0.01 to 100 mg/kg, preferably 0.1 to 10 mg/kg may be selected. However, the therapeutic agent containing anti-human TF antibody of the present invention is not limited to these dosages.

Preferably the method of administration is, but is not limited to, intravenous injection, intravenous drip, and the like.

The therapeutic agent of the present invention comprising anti-human TF antibody as an active ingredient may be formulated using a standard method (Remington's Pharmaceutical Science, the latest edition, Mark Publishing Company, Easton, USA), and may contain pharmaceutically acceptable carriers and/or additives.

Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, agar, polyethylene glycol, diglycerin, glycerin, propylene glycol, Vaseline, paraffin, stearyl alcohol, stearic acid, human serum albumin (HSA), mannitol, sorbitol, lactose, a pharmaceutically acceptable surfactant and the like.

Additives used are chosen from, but are not limited to, the above or combinations thereof, as appropriate, depending on the dosage form of the present invention. For example, when used as injections, purified anti-human TF antibody may be dissolved in a solvent such as physiological saline, a buffer, and a glucose solution, to which an anti-adsorbent such as Tween 80, Tween 20, gelatin, and human serum albumin may be added. Alternatively, they may be lyophilized so as to be dissolved and reconstituted into a dosage form before use. As the excipient for lyophilization, sugar alcohols and sugars such as mannitol and glucose may be used.

EXAMPLES

The present invention will now be explained more specifically with reference to the examples.

Example 1

Generation of Experimental Mice

A vector in which a gene encoding human tissue factor (SEQ ID NO: 103) had been inserted into an animal expression vector pCOS1 (hTF-pCOS1) was digested with a restriction enzyme PruI and linearized, which was then introduced into a human myeloma cell line KPMM2 (FERM P-14170) by electroporation.

pCOS1 was constructed by removing the antibody gene from HEF-PMh-gγ1 (WO 92/19759) by digesting with EcoRI and SmaI and then by ligating the EcoRI-NotI-BamHI adaptor (Takara Shuzo). This was cultured in a RPMI1640 medium (containing 20% FCS hIL-6: 4 ng/ml) containing 1 mg/ml G418, and the cells that grew were confirmed to be the expression of human tissue factor using anti-human tissue factor antibody (American Diganostica) by flow cytometry. This gave a cell line KPMM2/TF226 that has introduced a human tissue factor gene therein.

The parent strain (KPMM2/parent) before the introduction of the above human tissue factor gene and the gene-introduced strain KPMM2/TF226 were cultured in a RPMI-1640 medium containing 4 ng/ml human IL-6 and 20% bovine fetal serum. The thus-grown KPMM2/TF226 cells and the parent KPMM2/parent cells, separately, were implanted subcutaneously at $1 \times 10^7$ cells into the flanks of SCID mice (available from CLEA Japan, male, 7-week old, mean body weight: about 22 g), and changes with time in tumor volume, platelet counts in the blood, and plasma concentrations of human tissue factor, fibrinogen, soluble fibrin monomer complex (sFMC), and thrombin-antithrombin III complex (TAT) were investigated.

Figure 5:
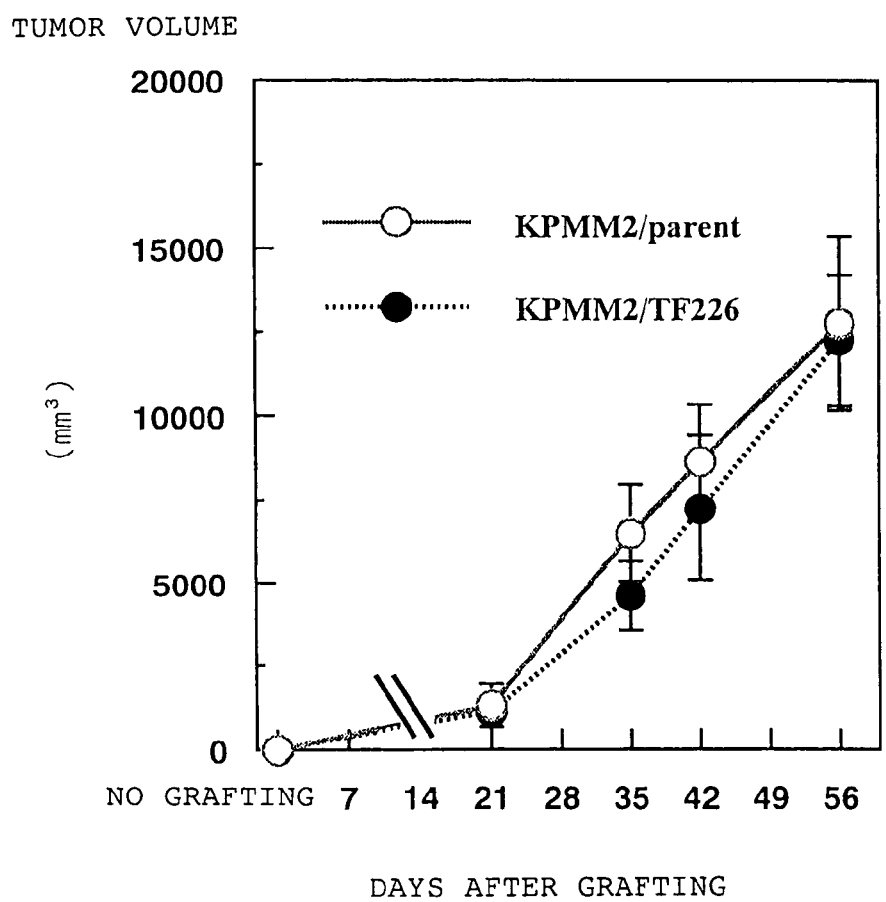
FIG. 5 is a graph showing changes in tumor volume with time after the implantation of tumor cells in the mice implanted with the cells to which gene of human tissue factor has been introduced (dotted line) and in the mice implanted with the cells to which said gene has not been introduced (solid line).
Figure 6:
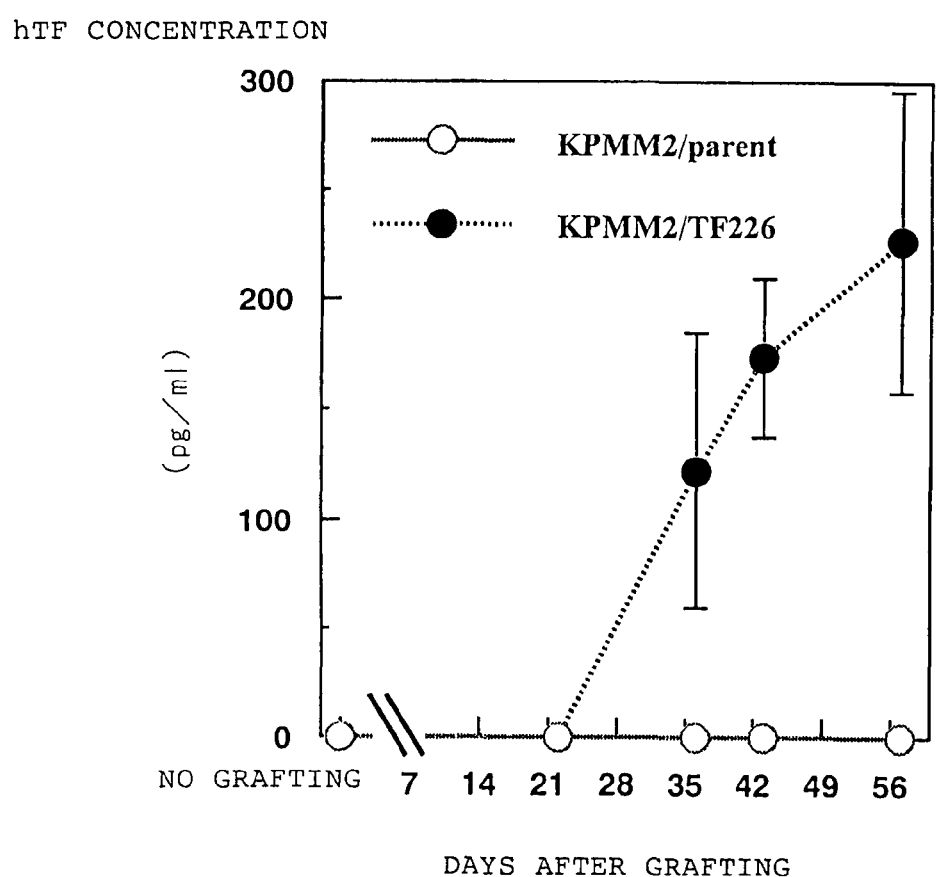
FIG. 6 is a graph showing changes in the plasma concentration of human tissue factor with time after the implantation of tumor cells in the mice implanted with the cells to which gene of human tissue factor has been introduced (dotted line) and in the mice implanted with the cells to which said gene has not been introduced (solid line).
Figure 7:
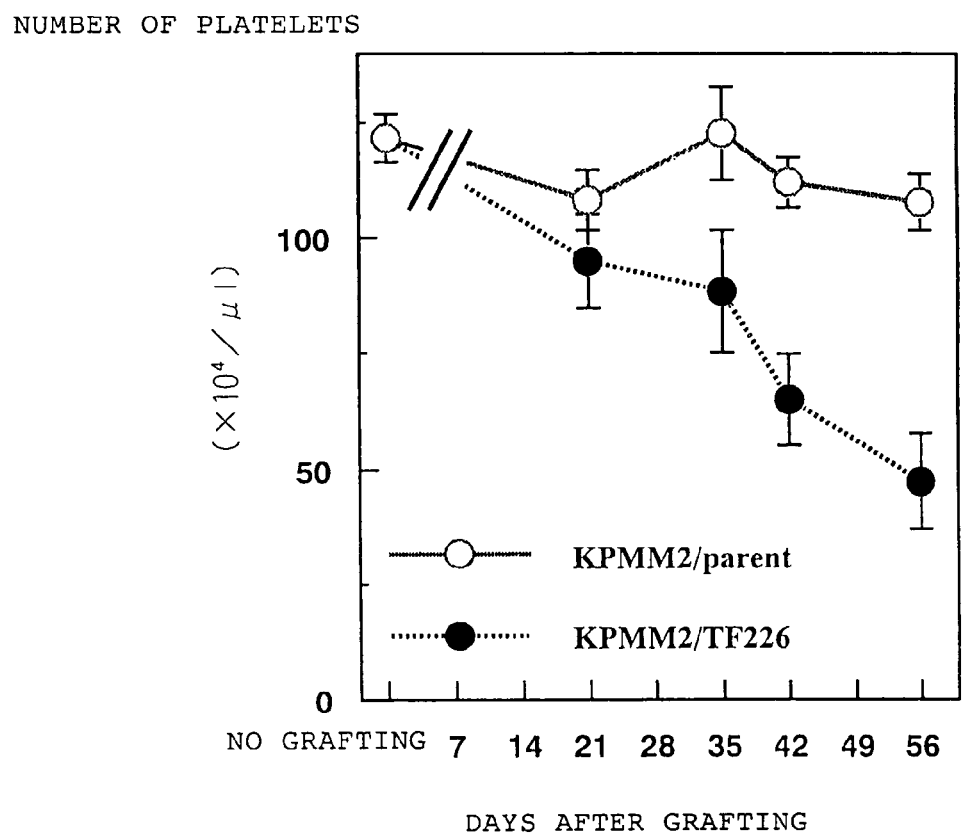
FIG. 7 is a graph showing changes in platelet counts with time after the implantation of tumor cells in the mice implanted with the cells to which gene of human tissue factor has been introduced (dotted line) and in the mice implanted with the cells to which said gene has not been introduced (solid line).
Figure 8:
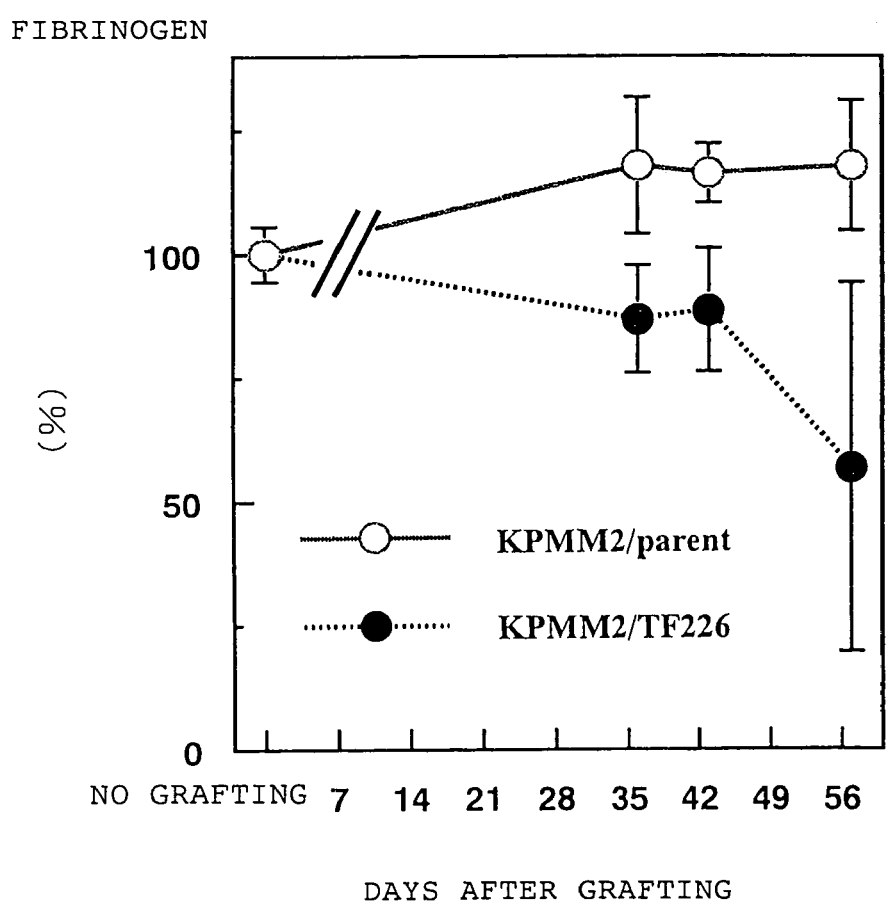
FIG. 8 is a graph showing changes in the plasma concentration of fibrinogen with time after the implantation of tumor cells in the mice implanted with the cells to which gene of human tissue factor has been introduced (dotted line) and in the mice implanted with the cells to which said gene has not been introduced (solid line). The points indicate relative values, in which the concentration of fibrinogen in the control mice to which tumor cells have not been implanted (normal) is expressed as 100%.

As a result, as shown in FIG. 5, tumor volume increased with time in all mice. As shown in FIG. 6, however, the plasma concentration of human tissue factor increased with time in the mice having implanted therein cells to which the human tissue factor gene had been introduced, but did not increase at all in the mice having implanted therein cells to which the human tissue factor gene had not been introduced. As shown in FIG. 7 and FIG. 8, in the mice having implanted therein cells to which the human tissue factor gene had been introduced, each of platelets and fibrinogen decreased with time, indicating that these coagulation components in the blood were consumed. In contrast, in the mice having implanted therein cells to which the human tissue factor gene had not been introduced, no decrease (consumption) in these coagulation components in the blood was noted.

Figure 9:
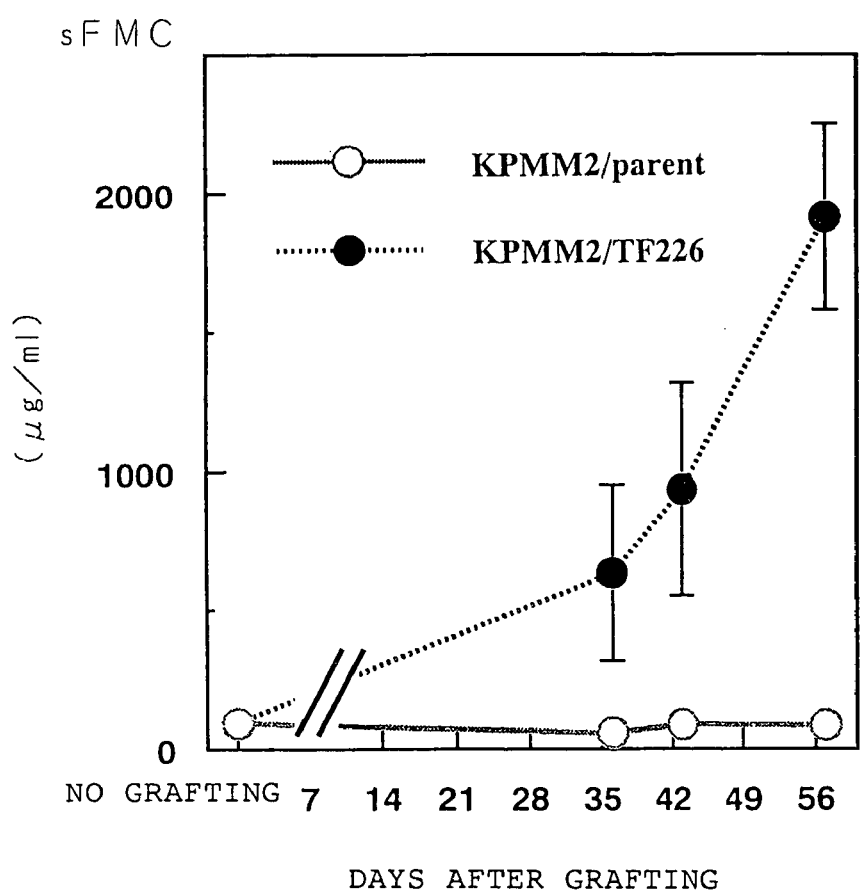
FIG. 9 is a graph showing changes in the plasma concentration of soluble fibrin monomer complex (sFMC) with time after the implantation of tumor cells in the mice implanted with the cells to which gene of human tissue factor has been introduced (dotted line) and in the mice implanted with the cells to which said gene has not been introduced (solid line).
Figure 10:
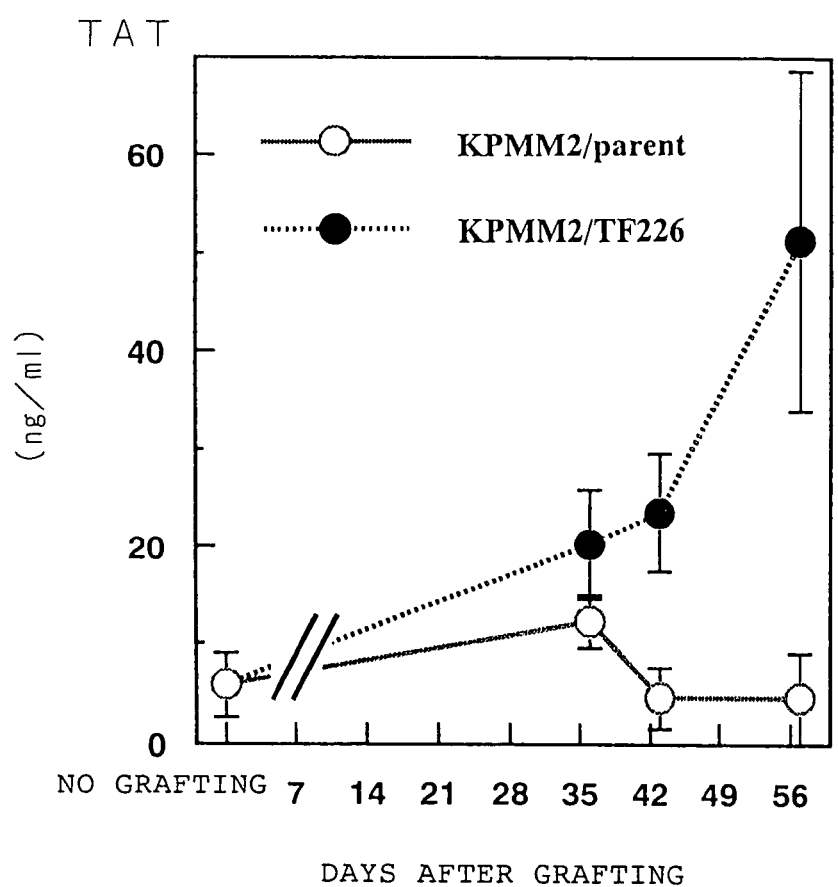
FIG. 10 is a graph showing changes in the plasma concentration of thrombin-antithrombin III complex (TAT) with time after the implantation of tumor cells in the mice implanted with the cells to which gene of human tissue factor has been introduced (dotted line) and in the mice implanted with the cells to which said gene has not been introduced (solid line).

As shown in FIG. 9 and FIG. 10, in the mice having implanted therein cells to which the human tissue factor gene had been introduced, the plasma concentration of each of soluble fibrin monomer complex (sFMC) and thrombin-antithrombin III complex (TAT) increased with time, indicating that the hypercoagulable state is persistent. In contrast, in the mice having implanted therein cells to which the human tissue factor gene had not been introduced, no increases in the above coagulation components in the blood were noted.

From the above results, it was confirmed that, in the mice having implanted therein cells to which the human tissue factor gene had been introduced, the hypercoagulable state is persistent, confirming that the animal of the present invention is useful as a model of a chronic hypercoagulable state.

Example 2

The effect of the humanized anti-human TF antibody version "i-b2" was investigated in the model described in Example 1. Five to six weeks after the implantation of KPMM2/TF226 to SCID mice (CLEA Japan, male, 7-week old, mean body weight: about 22 g), at when platelet counts fell to about half that of the non-tumor-implanted group, confirming the persistence of a hypercoagulable state, and thus from day 45 after the implanted 1 mg/kg of humanized anti-human TF antibody version "i-b2" was intravenously administered once a week. As a result, on day 3 after the administration of humanized anti-human TF antibody version "i-b2", platelet counts recovered to a level higher than that in the non-tumor-implanted group, and platelet counts were maintained at a level equal to that in the non-tumor-implanted group during the period from the start of the administration to week 3 when the experiment ended.

On day 6 after the third administration of humanized anti-human TF antibody version "i-b2", the plasma concentrations of soluble fibrin monomer complex (sFMC) and of thrombin-antithrombin III complex (TAT) were determined, and it was found that the administration of the antibody suppressed their increases (FIG. 12 and FIG. 13). These results indicated that humanized anti-human TF antibody version "i-b2" had the effect of stably maintaining coagulation at a normal level, by a once-per-week administration in the model in which a hypercoagulable state persists for a long period.

Example 3

LPS dissolved in physiological saline was continuously injected into a vein at a done of 1 mg/kg/hr (2 ml/kg/hr) for 6 hours to cynomolgus monkeys (imported from Chuang Primates Experimental Animal Research Center, Nanning, the People's Republic of China, equal numbers of males and females, estimated age: 5-7 years old, body weight: 2.99-5.81 kg) under isoflurane anesthesia. Intravenous administration of humanized anti-human TF antibody "version i-b2" at 0.3 mg/kg (1 ml/kg) to monkeys of the humanized anti-human TF antibody-administration group, and that of a solvent (20 mM sodium acetate/150 mM NaCl, pH 6.0) to monkeys of the control group were made respectively 10 minutes before the start of continuous injection of LPS.

At the end of continuos injection of LPS, citrated blood and normal blood were drawn via the catheter mounted to the femoral artery, and prothrombin time, plasma concentration of fibrinogen and serum concentration of fibrin degradation products were determined. As shown in Table 4, LPS injection resulted in the elongation of prothrombin time, decreases in plasma concentration of fibrinogen, and increases in serum concentration of fibrin degradation products, i.e. a hypercoagulable state, but in the monkeys that had received humanized anti-human TF antibody "version i-b2", these changes were strongly suppressed. These results reveal that humanized anti-human TF antibody "version i-b2" can suppress the hypercoagulable state resulting from infections.

TABLE 4

Effect of humanized anti-human TF antibody on hypercoagulability by LPS injection

| | Control group (n = 4) | | Humanized anti-human TF antibody administration group (n = 4) | |
| --- | --- | --- | --- | --- |
| | Before LPS injection | After LPS injection | Before LPS injection | After LPS injection |
| Prothrombin time (seconds) | 11.1 ± 0.3 | 15.8 ± 2.3 | 10.9 ± 0.3 | 11.7 ± 0.6 |
| Plasma concentration of fibrinogen (mg/dl) | 150 ± 20 | 90 ± 20 | 170 ± 10 | 160 ± 20 |
| Serum concentration of fibrin degradation (μg/ml) | 0 ± 0 | 43 ± 14 | 0 ± 0 | 8 ± 4 |

* Mean ± standard error

Example 4

In a model of venous thrombosis induced by venostasis and a venous wall injury, the effect of humanized anti-human TF antibody on the venous thrombosis was evaluated. The venostasis was created by the ligation of the blood vessel. The venous wall injury was induced using "polidocanol (a therapeutic agent for esophageal varices, Kreussler)".

Cynomolgus monkeys with an estimated age of 3-4 years old, weighing 2.97-3.99 kg (obtained from Chuang Primate Experimental Animal Research Center, the people's Republic of China) were used in the venous thrombosis model. The monkeys were anesthetized with mixture of isoflurane and nitrous oxide to expose the bilateral jugular veins. A segment of the exposed jugular vein was completely ligated with suture around the site proximal to the heart, and was reversibly legated with suture around the site nearer to the head so as to be loosened afterward. A catheter was inserted into the segment between the both ligation of the exposed jugular vein, from the nearer site to the heart in the direction toward the head. Blood in the segment between the ligations of the exposed jugular vein was removed through the catheter and the inside was washed with physiological saline. Via the catheter, 0.5% polidocanol was injected into the segment between the ligations of the exposed blood vessel. The catheter was removed and, at the same time, the segment of the blood vessel was reversibly ligated at the immediate upper part of the catheter insertion site.

Five minutes later, the reversible ligation at the heart side was loosened to remove polidocanol. The reversible ligation at the head side was loosened to drain a small amount of blood, and then the segment of the exposed blood vessel was completely at the immediate upper part of the catheter insertion site. After the segment was filled with blood, the exposed jugular vein was completely ligated at the part nearer to the head. The segment between the both complete ligations was adjusted to be 1.5 cm in length. Thirty minutes later, the wet weight of the formed clots was measured. For the assessment, the sum of the wet weight of the clots in the bilateral jugular veins was used. Humanized anti-human TF antibody "version i-b2" was intravenously administered at a dose of 0.3 mg/kg and 1.5 mg/kg 2 hours before the start of the venous thrombus formation.

The results are shown in Table 5. The administration of humanized anti-human TF antibody led to the reduction in the weight of the clots formed. Therefore, these result indicate that humanized anti-human TF antibody has a prophylactic effect on the venous thrombus formation in this model.

TABLE 5

Effect of humanized anti-human TF antibody in the venous thrombosis cynomolgus monkey

|  | Test agent not administered (n = 2) | Humanized anti-human TF antibody 0.3 mg/kg i.v. (n = 2) | Humanized anti-human TF antibody 1.5 mg/kg i.v. (n = 2) |
|---|---|---|---|
| Sum of the wet weight of venous clots in the left and right carotid veins (mg) | 20.8<br>21.9 | 1.4<br>1.1 | 0.0<br>0.4 |
| Mean | 21.4 | 1.3 | 0.2 |

Example 5

In a model of arterial thrombosis induced by angiostenosis and an arterial wall injury, the effect of humanized anti-human TF antibody on the arterial thrombosis was evaluated. The angiostenosis and the arterial wall injury were made by tightly ligating a blood vessel with a 20G needle pinched therein with its tip rounded and then removing the needle. This is a model that mimics angiostenosis due to arteriosclerosis and the arterial wall injury due to the plaque rupture.

Cynomolgus monkeys with an estimated age of 3-5 years old, weighing 3.55-3.99 kg (obtained from Chuang Primates Experimental Animal Research Center, the People's Republic of China) were used in the arterial thrombosis model. The monkeys were anesthetized with ketamine hydrochloride (intramuscular administration) and butofanol (intramuscular administration) to expose the right common carotid artery. The probe of a doppler flowmeter was placed around the exposed blood vessel, and blood flow was monitored for about 5 minutes. After confirming the constant flow of the bloodstream, angiostenosis and the arterial wall injury were induced around the proximal site to the head side of the probe.

The blood flow was observed for the subsequent 15 minutes, and the time of vascular occlusion due to thrombus formation was determined. After loosening the ligation at the right common carotid artery, humanized anti-human TF antibody was administered to the monkeys of the antibody administration group. In the left common carotid artery as well, the time of vascular occlusion due to thrombus formation was determined. Humanized anti-human TF antibody "version i-b2" was intravenously administered at a dose of 0.3 mg/kg and 1.5 mg/kg one hour before the start of the thrombus formation at the left common carotid artery.

The results are shown in Table 6. The administration of humanized anti-human TF antibody led to the reduction in the time of vascular occlusion. Therefore, these results indicate that humanized anti-human TF antibody has a prophylactic effect on the arterial thrombus formation in this model.

TABLE 6

Effect of humanized anti-human TF antibody in the arterial thrombosis cynomolgus monkey

|  | Test agent not administered (n = 2) | Humanized anti-human TF antibody 0.3 mg/kg i.v. (n = 2) | Humanized anti-human TF antibody 1.5 mg/kg i.v. (n = 2) |
|---|---|---|---|
| The time of vascular occlusion during 15-min observation after test agent administration (minutes) [left common carotid artery] | 12.2 | 7.2 | 3.5 |
| The time of vascular occlusion during 15-min observation after test agent administration (minutes) [left common carotid artery-right common carotid artery] | +0.9 | −4.4 | −6.2 |

* All are the mean of the group.

Example 6

Cynomolgus monkeys (purchased from KEARI Inc., monkeys raised in Vietnam, the estimated age of 4-5 years) were anesthetized under 5-10 mg/kg of Ketalar, im, and 15-20 mg/kg of pentobarbital, iv, and the neck was incised to expose the carotid artery. Via the external carotid artery, a Fogarty catheter (3-5F) was inserted and the balloon was inflated to scrape the vascular intima for five times. After scraping, the catheter was extracted and the wound was sutured. One month later, the animals were euthanized and the carotid artery was removed. At this time, the contralateral carotid artery that was not balloon-injured was extracted in a similar manner.

Humanized anti-human TF antibody "version i-b2" was intravenously administered at a dose of 0.3 mg/kg over 1 minutes, 10 minutes before the vascular injury. The extracted artery was fixed in formalin, histological specimens were prepared, and stained with a HE stain and Elastica van Gieson stain, followed by image analysis to measure the area of the intima. As a result, as shown in Table 7, humanized anti-human TF antibody "version i-b2" strongly suppressed the hypertrophy of the intima. This indicated that humanized anti-human TF antibody "version i-b2" prevents the narrowing of the area of the lumen during the remote period by suppressing the growth of the blood vessel tissue itself, suggesting that it can effectively prevent restenosis.

TABLE 7

|  | Animal No. | Non-injured blood vessel Area of media (mm$^2$) | Injured blood vessel Area of media (mm$^2$) |
|---|---|---|---|
| Control group | 1 | 1.06 | 2.15 (203%) |
|  | 2 | 0.74 | 1.45 (196%) |
|  | 3 | 0.82 | 1.78 (217%) |
| Anti-human TF antibody | 4 | 0.75 | 1.15 (153%) |
|  | 5 | 0.78 | 0.96 (123%) |
|  | 6 | 0.86 | 0.98 (114%) |

(Percentage relative to the non-injured side)

Example 7

The effect of humanized anti-human TF antibody "version i-b2" and low molecular weight heparin was investigated in the model described in Example 1. Six to seven weeks after the grafting of KPMM2/TF226 to SCID mice (CLEA Japan, male, 7 weeks old, mean body weight: about 24 g), platelet counts reduced to about half that of the non-tumor-grafted group, confirming the persistence of the hypercoagulable state. Hence, from day 49 after the grafting 1 mg/kg of humanized anti-human TF antibody version "i-b2" was intravenously administered or low molecular weight heparin at 601.5 IU/kg, 1900.3 IU/kg, and 6487.3 IU/kg was continuously administered by subcutaneously embedding an osmotic pump that permits sustained release for 24 hours. As a result, on day 1 after the administration of humanized anti-human TF antibody version "i-b2", platelet counts recovered, and on day 3 platelet counts were higher than that in the non-tumor-grafted group, and day 3 the effect was maintained even after day 7. In contrast, in the administration group of 6487,3 IU/kg of low molecular weight heparin, a slight recovery in platelet counts was observed one and two days after the start of the continuous administration, but on day 3 the effect disappeared though there was a slight recovery in platelets counts (FIG. 14).

Reference Example 1

Method of Preparing Soluble Human TF

Soluble human TF (shTF) was prepared in the following manner.

The gene encoding the human TF penetrating region in which amino acids at position 220 and thereafter had been replaced with the FLAG peptide M2 was inserted to a mammalian cell expression vector (containing the neomycin resistant gene and the DHFR gene), and introduced into CHO cells. For the cDNA sequence of human TF, reference was made to an article by James H. Morrissey et al. (Cell (1987) 50: 129-135). The gene sequence and the amino acid sequence of this soluble human TF are shown in SEQ ID NOs: 101 and 102. After drug selection with G418, the expressed cells were selected, which were then subjected to expression amplification with methotrexate, and the shTF-expressing cells were established.

The cells were cultured in the serum-free medium CHO—S-SFMII (GIBCO) to obtain a culture supernatant containing shTF. It was diluted 2-fold with an equal volume of a 40 mM Tris-HCl buffer (pH 8.5), which was added to the Q-Sepharose Fast Flow column (100 ml, Pharmacia Biotech) equilibrated with a 20 mM Tris-HCl buffer (pH 8.5). After washing with the same buffer containing 0.1 M NaCl, the concentration of NaCl was changed to 0.3 M, and shTF was eluted from the column. To the shTF fraction obtained, ammonium sulfate was added to a final concentration of 2.5 M, and was centrifuged (10,000 rpm, 20 minutes) to precipitate the contaminating proteins. The supernatant was added to Butyl TOYOPEARL (30 ml, TOSOH), and then was washed with a 50 mM Tris-HCl buffer (pH 6.8) containing 2.5 M ammonium sulfate. In the 50 mM Tris-HCl buffer (pH 6.8), the concentration of ammonium sulfate was linearly reduced from 2.5 M to 0 M to permit the elution of shTF. The peak fractions containing shTF were concentrated by the Centri-Prep 10 (Amicon). The concentrate was added to the TSKgel G3000SWG column (21.5×600 mm, TOSOH) equilibrated with a 20 mM Tris-HCl buffer (pH 7.0) containing 150 mM NaCl, and the peak fraction of shTF was collected. It was filter sterilized with a 0.22 μm membrane filter and the product was set as the soluble human TF (shTF). The concentration of the sample was calculated assuming that the molar extinction coefficient of the sample $\epsilon$=40,130 and molecular weight=43,210.

Reference Example 2

Preparation of Anti-TF Monoclonal Antibody

1. Purification of Human TF

The purification of TF from human placenta was carried out according to the method of Ito (Ito, T. et al., J. Biol. Chem., 114: 691-696, 1993). Thus, human placenta was homogenized in Tris buffered saline (TBS, pH 7.5) containing 1.0 mM benzamidine hydrochloride, 1 mM phenylmethylsulfonyl fluoride, 1 mM diisopropylfluoro phosphate, and 0.02% sodium azide, and then the precipitate was defatted with cold acetone. The defatted powder obtained was suspended in the above buffer containing 2% Triton X-100 to solubilize TF.

The supernatant was subjected to affinity chromatography using Concanavalin A-Sepharose 4B column (Pharmacia) and anti-TF antibody-bound Sepharose 4B column (Pharmacia), and purified TF was obtained. This was concentrated with an ultrafiltration membrane (PM-10, Amicon) and was stored as the purified sample at 4° C.

TF content in the purified sample was quantitated by Sandwich ELISA that combined a commercially available anti-TF monoclonal antibody (American Diagnostica) and polyclonal antibody (American Diagnostica) with recombinant TF as a standard.

The purity in the purified sample was confirmed by subjecting the sample to SDS-PAGE using a 4-20% density gradient polyacrylamide gel, and silver-staining the product.

2. Immunization and the Preparation of Hybridoma

After mixing the purified human TF (about 70 µg/ml) with an equal volume of Freund's complete adjuvant (Difco), it was immunized subcutaneously into the abdomen of 5-week old Balb/c male mice (Nippon Charles River) at 10 µg TF/mouse. On day 12, 18, and 25, TF mixed with Freund's incomplete adjuvant was subcutaneously boosted at 5 µg/mouse TF, and as a final immunization the TF solution diluted with PBS was intraperitoneally given at 5 µg/mouse on day 32.

Three days after the final immunization, the spleen cells were prepared from four mice, and were fused to the mouse myeloma cell line P3U1 at ⅕ cell count thereof by the polyethylene glycol method. The fused cells were suspended into the RPMI-1640 medium (hereinafter referred to as RPMI-medium) (Lifetech Oriental) containing 10% fetal bovine serum, which was inoculated in 400 wells per mouse (about 400 cells/well) of a 96-well plate. On day 1, 2, 3, and 5 after the fusion, half the volume of the medium was exchanged with the RPMI-medium (hereinafter referred to as HAT-medium) containing HAT (Dainippon Seiyaku) and condimed H1 (Boehringer Mannheim GmbH) to perform HAT selection of the hybridoma.

The hybridomas selected by the screening method described below were cloned by conducting limiting dilution twice.

For the limiting dilution, 0.8 cells was inoculated per well in two 96-well plates. For the wells in which single colony was confirmed by microscopic examination, clones were selected by the following measurement of the binding activity to TF and neutralizing activity against TF. The clones obtained were acclaimed from the HAT-medium to the RPMI-medium. After the absence of reduction in antibody production ability due to acclimation was confirmed, limiting dilution was performed again for complete cloning. By the foregoing procedure, hybridomas that produce six antibodies (ATR-2, 3, 4, 5, 7, and 8) that strongly inhibit the binding of TF/Factor VIIa complex and Factor X were established.

3. Ascites Formation and Antibody Purification

The ascites formation of the established hybridomas were carried out according to the standard method. Thus, $10^6$ hybridomas that were subcultured in vitro were intraperitoneally grafted into BALB/c male mice that had previously received twice intravenous administration of mineral oil. Ascites was collected from the mice that showed a bloated abdomen 1-2 weeks after the grafting.

The purification of antibody from ascites was carried out using the ConSepLC100 system (Millipore) equipped with the Protein A column (Nippon Gaishi).

4. Cell-ELISA

Human bladder carcinoma cells J82 (Fair D. S. et al., J. Biol. Chem., 262: 11692-11698, 1987) that are known to express TF at a high level were obtained from ATCC, and subcultured and maintained in the RPMI-medium under the condition of 37° C., 5% $CO_2$, and 100% humidity.

Cell-ELISA plates were prepared by inoculating J82 cells to a 96-well plate at $10^5$ cells/well, culturing for one day under the above condition, removing the medium and then washing twice with phosphate buffered saline (PBS), adding a 4% paraformaldehyde solution (PFA), and allowing to stand on ice for 10 minutes for immobilization. After PFA was removed, the plate was washed with PBS, the Tris buffer (Blocking buffer) containing 1% BSA and 0.02% sodium azide was added thereto, and the plate was stored at 4° C. until use.

Cell-ELISA was carried out in the following manner. Thus, the Blocking buffer was removed from the plate prepared as above, to which an anti-TF antibody solution or a hybridoma culture supernatant was added and was reacted at room temperature for 1.5 hours. After washing with PBS containing 0.05% Tween 20, alkaline phosphatase-conjugated goat anti-mouse IgG (H+L) (Zymed) was reacted for 1 hour. After washing, 1 mg/ml p-nitrophenyl phosphate disodium (Sigma) was added, and one hour later absorbance at 405/655 nm was measured to determine the amount of anti-TF antibody that bound to the J82 cells.

5. Assay System of Neutralizing Activity Against TF with Factor Xa Activity as an Index To 50 µl of Tris buffered saline (TBS: pH 7.6) containing 5 mM $CaCl_2$ and 0.1% bovine serum albumin, 10 µl of a human placenta-derived thromboplastin solution (5 mg/ml) (Thromborel S) (Boehring) and 10 µl of a Factor VIIa solution (82.5 ng/ml) (American Diagnostics) were added, and reacted at room temperature for 1 hour to permit the formation of the TF/Factor VIIa complex. After 10 µl of a predetermined concentration of a diluted anti-TF antibody solution or the hybridoma culture supernatant and 10 µl of a Factor X solution (3.245 µg/ml) (Celsus Laboratories) were added and reacted for 45 minutes, 10 µl of 0.5 M EDTA was added to stop the reaction. Fifty µl of 2 mM S-2222 solution (Daiichi Kagaku Yakuhin) was added thereto, and changes in absorbance at 405/655 nm over 30 minutes were measured and was set as the Factor X-producing activity of TF. In this method, the activity of antibody that inhibits the binding of the TF/Factor VIIa complex and Factor X can be determined.

6. Assay System of Inhibiting Activity Against Plasma-Coagulation

Fifty µl of an appropriately diluted anti-TF antibody solution was mixed with 100 µl of a commercially available normal human plasma (Kojin Bio) and reacted at 37° C. for 3 minutes. Then 50 µl of human placenta-derived thromboplastin solution (1.25 mg/ml) was added thereto, and the time to coagulation of the plasma was measured using the plasma coagulation measuring instrument (CR-A: Amelung).

7. Determination of Antibody Isotype

For the culture supernatant of the hybridoma and the purified antibody, the mouse monoclonal antibody isotyping kit (manufactured by Amersham) was used to confirm the isotype of antibody. The result is shown below.

TABLE 5

| Immunoglobulin isotype of anti-TF monoclonal antibody | |
|---|---|
| ATR-2 | IgG1, k |
| ATR-3 | IgG1, k |
| ATR-4 | IgG1, k |
| ATR-5 | IgG1, k |
| ATR-7 | IgG2a, k |
| ATR-8 | IgG2a, k |

Reference Example 3

Cloning of DNA encoding the V Region of a Mouse Monoclonal Antibody Against Human TF (1) Preparation of mRNA mRNA was prepared from hybridoma ATR-5 (IgG1κ) obtained in Reference Example 2 using the QuickPrep mRNA Purification Kit (Pharmacia Biotech). Each hybridoma cell was completely homogenized in the extraction buffer according to instructions attached to the kit, and then mRNA was purified by the oligo (dT)-cellulose spun column, followed by ethanol precipitation. The mRNA precipitate was dissolved in the elution buffer.

(2) Preparation and Amplification of cDNA of the Gene Encoding a Mouse Antibody V Region (i) Cloning of H Chain V Region cDNA The cloning of the gene encoding the H chain V region of a mouse monoclonal antibody against human TF was carried out using the 5'-RACE method (Frohman, M. A. et al., Proc. Natl. Acad. Sci. USA 85: 8998-9002, 1988; Belyaysky, A. et al., Nucleic Acids Res. 17: 2919-2932, 1989). For the 5'-RACE method, the Marathon cDNA Amplification Kit (CLONTECH) was used and the procedure carried out according to the instructions attached to the kit.

Using about 1 μg of mRNA prepared as above as a template, the cDNA synthesis primer attached to the kit was added, which was reacted with a reverse transcriptase at 42° C. for 60 minutes to effect reverse transcription to cDNA. This was reacted with DNA polymerase I, DNA ligase, and RNaseH at 16° C. for 1.5 hour, and with T4 DNA polymerase at 16° C. for 45 minutes thereby to synthesize a double stranded cDNA. The double stranded cDNA was extracted with phenol and chloroform, and recovered by ethanol precipitation.

By overnight reaction with T4 DNA ligase at 16° C., a cDNA adapter was ligated to both ends of the double stranded cDNA. The reaction mixture was diluted 50-fold with a 10 mM Tricine-KOH (pH 8.5) containing 0.1 mM EDTA. Using this as a template, the gene encoding the H chain V region was amplified by PCR. The adapter primer 1 attached to the kit was used for the 5'-end primer, and for the 3'-end primer the MHC-G1 primer (SEQ ID NO: 1) (S. T. Jones, et al., Biotechnology, 9: 88-89, 1991) were used.

PCR solutions for the ATR-5 antibody H chain V region contained, in 100 μl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 30-50 pmole of adapter primer 1, as well as MHC-G1 primer, and 1-5 μl of a reaction mixture of cDNA to which the cDNA adapter was ligated.

All PCRs were carried out using the DNA Thermal Cycler 480 (Perkin-Elmer), and the PCR was performed for thirty cycles at a temperature cycle of 94° C. for 30 seconds, 55° C. for 30 seconds, and 74° C. for 1 minute.

(ii) Cloning of L Chain V Region cDNA

The cloning of the gene encoding the L chain V region of a mouse monoclonal antibody against human TF was carried out using the 5'-RACE method (Frohman, M. A. et al., Proc. Natl. Acad. Sci. USA 85: 8998-9002, 1988; Belyaysky, A. et al., Nucleic Acids Res. 17: 2919-2932, 1989). For the 5'-RACE method, the Marathon cDNA Amplification Kit (CLONTECH) was used and carried out according to the instructions attached to the kit. Using about 1 μg of mRNA prepared as above as a template, the cDNA synthesis primer was added, which was reacted with a reverse transcriptase at 42° C. for 60 minutes to effect reverse transcription to cDNA.

This was reacted with DNA polymerase I, DNA ligase, and RNaseH at 16° C. for 1.5 hour, and with T4 DNA polymerase at 16° C. for 45 minutes thereby to synthesize a double stranded cDNA. The double stranded cDNA was extracted with phenol and chloroform, and recovered by ethanol precipitation. By overnight reaction with T4 DNA ligase at 16° C., a cDNA adapter was ligated to both ends of the double stranded cDNA. The reaction mixture was diluted 50-fold with a 10 mM Tricine-KOH (pH 8.5) containing 0.1 mM EDTA. Using this as a template, the gene encoding the L chain V region was amplified by PCR. The adapter primer 1 was used for the 5'-end primer, and for the 3'-end primer the MKC primer (SEQ ID NO: 2) (S. T. Jones, et al., Biotechnology, 9: 88-89, 1991) was used.

PCR solutions contained, in 100 μl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 30-50 pmole of adapter primer 1, as well as MKC primer, and 1 μl of a reaction mixture of cDNA to which the cDNA adapter was ligated.

All PCRs were carried out using the DNA Thermal Cycler 480 (Perkin-Elmer), and the PCR was performed for thirty cycles at a temperature cycle of 94° C. for 30 seconds, 55° C. for 30 seconds, and 74° C. for 1 minute.

(3) Purification and Fragmentation of PCR Products

The above PCR reaction mixture was extracted with phenol and chloroform, and the amplified DNA fragments were recovered by ethanol precipitation. DNA fragments were digested with the restriction enzyme XmaI (New England Biolabs) at 37° C. for 1 hour. The XmaI-digestion mixture was separated by agarose gel electrophoresis using 2%-3% NuSieve GTG agarose (FMC BioProducts), and the agarose strips containing about 500 bp long DNA fragments as the H chain V region and about 500 bp Long DNA fragments as the L chain V region were excised. The agarose strips were extracted with phenol and chloroform, DNA fragments were precipitated with ethanol, which were then dissolved in 10 μl of 10 mM Tris-HCl (pH 8.0) containing 1 mM EDTA (hereinafter referred to as TE).

The XmaI-digested DNA fragments prepared as above containing a genes encoding a mouse H chain V region and L chain V region and the pUC19 plasmid vector prepared by digesting with XmaI were ligated using the DNA ligation kit ver.2 (Takara Shuzo) by reacting at 16° C. for 1 hour according to the instructions attached to the kit.

The ligation mixture was added to 100 μl of *E. coli* JM109 competent cells (Nippongene) and was incubated for 30 minutes on ice and for 1 minute at 42° C.

Then, 300 μl of the Hi-Competence Broth (Nippongene) was added thereto, incubated at 37° C. for 1 hour. Then, *Escherichia coli* was plated on a LB agar medium (Molecular Cloning: A Laboratory Manual, Sambrook, et al., Cold Spring Harbor Laboratory Press, 1989) containing 100 μg/ml ampicillin (hereinafter referred to as LBA agar medium), and incubated overnight at 37° C. to obtain an *E. coli* transformant.

The transformant was cultured overnight in 3 ml or 4 ml of a LB medium containing 50 μg/ml ampicillin (hereinafter referred to as LBA medium) at 37° C., and from the cell fractions, plasmid DNA was prepared using the QIAprep Spin Plasmid Kit (QIAGEN), and then the nucleotide sequence was determined.

(4) Determination of the Nucleotide Sequence of the Gene Encoding a Mouse Antibody V Region The nucleotide sequence of the cDNA coding region in the above plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) (SEQ ID NO: 3) and M13 Primer RV (Takara Shuzo) (SEQ ID NO: 4) were used, and the sequence was determined by confirming the nucleotide sequence in both directions.

Thus obtained plasmids containing the gene encoding the mouse H chain V region derived from the hybridoma ATR-5 was designated as ATR-5Hv/pUC19, and the thus obtained plasmids containing the gene encoding a mouse L chain V region derived from the hybridoma ATR-5 was designated as ATR-5Lv/pUC19. The nucleotide sequences of the genes encoding the H chain V region of each mouse antibody contained in the plasmid ATR-5Hv/pUC19 (including the corresponding amino acid sequences) is shown in SEQ ID NO: 5 and 99, respectively, and the nucleotide sequences of the genes encoding the L chain V region of each mouse antibody contained in the plasmid ATR-5Lv/pUC19 (including the corresponding amino acid sequences) is shown in SEQ ID NO: 6 and 100, respectively.

Reference Example 4

Construction of Chimeric Antibody

A chimeric ATR-5 antibody was generated in which the mouse ATR-5 antibody V region was ligated to the human antibody C region. A chimeric antibody expression vector was constructed by ligating the gene encoding the ATR-5 antibody V region to an expression vector encoding the human antibody C region.

(1) Construction of a Chimeric Antibody H Chain V Region

The ATR-5 antibody H chain V region was modified by the PCR method in order to ligate it to an expression vector encoding the human antibody H chain C region. The 5'-end primer ch5HS (SEQ ID NO: 7) was designed so as to hybridize the 5'-end of DNA encoding the V region and to have the Kozak consensus sequence (Kozak, M. et al., J. Mol. Biol. 196: 947-950, 1987) and a recognition sequence of the restriction enzyme SalI. The 3'-end primer ch5HA (SEQ ID NO: 8) was designed so as to hybridize 3'-end of DNA encoding the J region and to have a recognition sequence of the restriction enzyme NheI.

The PCR solutions contained, in 100 µl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 50 pmole of the ch5HS primer and the ch5HA primer, as well as 1 µl of the plasmid ATR5Hv/pUC19 as a template DNA. For PCR, the DNA Thermal Cycler 480 (Perkin-Elmer) was used, and the PCR was performed for thirty cycles at a temperature cycle of 94° C. for 30 seconds, 55° C. for 30 seconds, and 74° C. for 1 minute.

The PCR reaction mixture was extracted with phenol and chloroform, and the amplified DNA fragments were recovered by ethanol precipitation. The DNA fragments were digested with the restriction enzyme NheI (Takara Shuzo) at 37° C. for 1 hour, and then with the restriction enzyme SalI (Takara Shuzo) at 37° C. for 1 hour. The digestion mixture was separated by agarose gel electrophoresis using a 3% NuSieve GTG agarose (FMC BioProducts), and the agarose strips containing about 450 bp long DNA fragments were excised. The agarose strips were extracted with phenol and chloroform, and the DNA fragments were precipitated with ethanol, which were then dissolved in 20 µl of TE.

As the cloning vector, an altered promoter vector (hereinafter referred to as CVIDEC) was used in which the recognition sequences of the restriction enzymes NheI, SalI, and SplI, BglII were introduced. The gene fragment prepared as above encoding the mouse H chain V region and the CVIDEC vector prepared by digesting with NheI and SalI were ligated using the DNA ligation kit ver.2 (Takara Shuzo) by reacting at 16° C. for 1 hour according to the instructions attached to the kit.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on the LBA agar medium and incubated overnight at 37° C. to obtain an *E. coli* transformant. The transformant was cultured overnight at 37° C. in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) (SEQ ID NO: 3) and M13 Primer RV (Takara Shuzo) (SEQ ID NO: 4) were used, and the sequence was determined by confirming the nucleotide sequence in both directions. The plasmid that contains the gene encoding the ATR-5 antibody H chain V region, a SalI recognition sequence and the Kozak consensus sequence at the 5'-end, and a NheI recognition sequence at the 3'-end was designated as chATR5Hv/CVIDEC.

(2) Construction of a Chimeric Antibody L Chain V Region

The ATR-5 antibody L chain V region was modified by the PCR method in order to ligate it to an expression vector encoding the human antibody L chain C region. The 5'-end primer ch5LS (SEQ ID NO: 9) was designed so as to hybridize to the 5'-end of the DNA encoding the V region and to have the Kozak consensus sequence (Kozak, M. et al., J. Mol. Biol. 196: 947-950, 1987) and a recognition sequence of the restriction enzyme BglII. The 3'-end primer ch5LA (SEQ ID NO: 10) was designed so as to hybridize to the 3'-end of the DNA encoding the J region and to have a recognition sequence of the restriction enzyme SplI.

The PCR solutions contained, in 100 µl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 50 pmole of the ch5LS primer and the ch5LA primer, as well as 1 µA of the plasmid ATR5Lv/pUC19 as a template DNA. For PCR the DNA Thermal Cycler 480 (Perkin-Elmer) was used, and the PCR was performed for thirty cycles at a temperature cycle of 94° C. for 30 seconds, 55° C. for 30 seconds, and 74° C. for 1 minute.

The PCR reaction mixture was extracted with phenol and chloroform, and the amplified DNA fragments were recovered by ethanol precipitation. The DNA fragments were digested with the restriction enzyme SplI (Takara Shuzo) at 37° C. for 1 hour, and then with the restriction enzyme BglII (Takara Shuzo) at 37° C. for 1 hour. The digestion mixture was separated by agarose gel electrophoresis using a 3% NuSieve GTG agarose (FMC BioProducts), and the agarose strips containing about 400 bp long DNA fragments were excised. The agarose strips were extracted with phenol and chloroform, the DNA fragments were precipitated with ethanol, which were then dissolved in 20 µl of TE.

The gene fragment prepared as above encoding the mouse L chain V region and the CVIDEC vector prepared by digesting with SpII and BglII were ligated using the DNA ligation kit ver.2 (Takara Shuzo) by reacting at 16° C. for 1 hour according to the instructions attached to the kit.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on a 100 µg/ml LBA agar medium and incubated overnight at 37° C. to obtain an E. coli transformant. The transformant was cultured overnight at 37° C. in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions. The plasmid that contains the gene encoding the ATR-5 antibody L chain V region and that has a BglII recognition sequence and the Kozak consensus sequence at the 5'-end and a SpII recognition sequence at the 3'-end was designated as chATR5Lv/CVIDEC.

(3) Construction of a Chimeric Antibody Expression Vector

A chimeric antibody expression vector was constructed using an antibody expression vector introduced from IDEC Pharmaceuticals. As the vector, the IgG1-type antibody expression vector H5KG1(V) and the IgG4-type antibody expression vector N5KG4P were used. The chimeric ATR-5 antibody expression vector was generated by ligating a gene encoding the H chain V region of ATR-5 to the SalI-NheI site located immediately before the human antibody H chain C region of the expression vector N5KG1(V) or N5KG4P and ligating a gene encoding the L chain V region of ATR-5 to the BglII-SpII site located immediately before the human antibody L chain C region of the expression vector N5KG1(V) or N5KG4P.

(i) Introduction of H Chain V Region

The plasmid chATR5Hv/CVIDEC was digested with the restriction enzyme NheI (Takara Shuzo) at 37° C. for 3 hours, and with the restriction enzyme SalI (Takara Shuzo) at 37° C. for 3 hours. The digestion mixture was separated by agarose gel electrophoresis using 1.5% NuSieve GTG agarose (FMC BioProducts), and the agarose strips containing about 450 bp long DNA fragments were excised. The agarose strips were extracted with phenol and chloroform, and the DNA fragments were precipitated with ethanol, which were then dissolved in 20 µl of TE.

The expression vector N5KG1(V) and N5KG4P were digested with the restriction enzyme NheI (Takara Shuzo) at 37° C. for 3 hours, and with the restriction enzyme SalI (Takara Shuzo) at 37° C. for 3 hours. The digestion mixture was separated by agarose gel electrophoresis using 1.5% NuSieve GTG agarose (FMC BioProducts), and the agarose strips containing about 9000 bp long DNA fragments were excised. The agarose strips were extracted with phenol and chloroform, and the DNA fragments were precipitated with ethanol, which were then dissolved in 20 µl of TE.

The SalI-NheI DNA fragment prepared as above containing the gene encoding the H chain V region and N5KG1(V) or N5KG4P digested with SalI and NheI were ligated using the DNA ligation kit ver.2 (Takara Shuzo) by reacting at 16° C. for 1 hour according to the attached instructions.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on a 100 µg/ml LBA agar medium and incubated overnight at 37° C. to obtain an E. coli transformant. The transformant was cultured overnight at 37° C. in 3 ml of the LBA medium, and from the cell fractions, plasmid DNA was prepared using the QIAprep Spin Plasmid Kit (QIAGEN). These plasmids containing the genes encoding the chimeric ATR-5 antibody H chain were designated as chATR5Hv/N5KG1(V) and chATR5Hv/N5KG4P, respectively.

(ii) Introduction of the L Chain V Region

The plasmid chATR5Lv/CVIDEC was digested with the restriction enzymes BglII (Takara Shuzo) and SpII (Takara Shuzo) at 37° C. for 1.5 hour. The digestion mixture was separated by agarose gel electrophoresis using 1.5% NuSieve GTG agarose (FMC BioProducts), and the agarose strips containing about 400 bp long DNA fragments were excised. The agarose strips were extracted with phenol and chloroform, and the DNA fragments were precipitated with ethanol, which were then dissolved in 20 µl of TE.

The plasmids chATR5Hv/N5KG1(V) and chATR5Hv/N5KG4P were digested with the restriction enzymes BglII (Takara Shuzo) and SpII (Takara Shuzo) at 37° C. for 1.5 hour. The digestion mixture was separated by agarose gel electrophoresis using 1.5% NuSieve GTG agarose (FMC BioProducts), and the agarose strips containing about 9400 bp long DNA fragments were excised. The agarose strips were extracted with phenol and chloroform, DNA fragments were precipitated with ethanol, which were then dissolved in 20 µl of TE.

The SpII-BglII DNA fragment prepared as above containing the gene encoding the L chain V region and chATR5Hv/N5KG1(V) or chATR5Hv/N5KG4P digested with SpII and BglII were ligated using the DNA ligation kit ver.2 (Takara Shuzo) by reacting at 16° C. for 1 hour according to the attached instructions.

The ligation mixture was added to 100 µl of E. coli JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the E. coli was plated on a 100 µg/ml LBA agar medium and incubated overnight at 37° C. to obtain an E. coli transformant. The transformant was cultured overnight at 37° C. in 1 l of the 2xYT medium containing 50 µg/ml ampicillin, and from the cell fractions, plasmid DNA was prepared using the Plasmid Maxi Kit (QIAGEN). These plasmids containing the gene encoding the chimeric ATR-5 antibody were designated as chATR5/N5KG1(V) and chATR5/N5KG4P, respectively.

(4) Transfection Into COS-7 Cells

In order to evaluate the activity of binding to the antigen and the neutralizing activity of chimeric antibody, the above expression plasmid was transfected to COS-7 cells and the antibody was transient expressed.

The plasmid chATR5/N5KG1(V) or chATR5/N5KG4P was transduced into COS-7 cells by electroporation using the Gene Pulser instrument (Bio Rad). Fifty µg of the plasmid was added to 0.78 ml of the COS-7 cells suspended in the Dulbecco PBS (−) (hereinafter referred to as PBS) at a cell concentration of $1 \times 10^7$ cells/ml, which was subjected to pulses of 1,500 V and 25 µF capacity.

After 10 minutes of the recovery period at room temperature, the electroporated cells were suspended in a DMEM medium containing 5% Ultra low IgG fetal bovine serum (GIBCO), and cultured using a 10 cm culture dish in a 5% $CO_2$ incubator. After culturing for 24 hours, the culture supernatant was aspirated off, and then a serum-free medium HBCHO (Irvine Scientific) was added. After further culturing for 72 hours, the culture supernatant was collected and centrifuged to remove cell debris.

(5) Purification of Antibody

From the culture supernatant of the COS-7 cells, chimeric antibody was purified using the rProtein A Sepharose Fast Flow (Pharmacia Biotech) as follows.

One ml of rProtein A Sepharose Fast Flow was filled into a column and the column was equilibrated by 10 volumes of TBS. The culture supernatant of COS-7 cells was applied to the equilibrated column, which was then washed with 10 volumes of TBS.

The adsorbed antibody fraction was then eluted by 13.5 ml of 2.5 mM HCl (pH 3.0), and the eluate was immediately neutralized by adding 1.5 ml of 1 M Tris-HCl (pH 8.0).

By performing ultrafiltration twice for the purified antibody fraction using the Centriprep 100 (Amicon), the solvent was replaced to 50 mM Tris-HCl (pH 7.6) containing 150 mM NaCl (hereinafter referred to as TBS), and was finally concentrated to about 1.5 ml.

(6) Establishment of a Stably-Producing CHO Cell Line

In order to establish a cell line that stably produces chimeric antibody, the above expression plasmid was introduced into CHO cells (DG44) acclimated to the CHO—S-SFMII serum-free medium (GIBCO).

The plasmid chATR5/N5KG1(V) or chATR5/N5KG4P was cleaved with the restriction enzyme SspI (Takara Shuzo) to linearize DNA, and after extraction with phenol and chloroform, DNA was recovered by ethanol precipitation. The linearized plasmid was transduced into the DG44 cells by electroporation using the Gene Pulser instrument (Bio Rad). Ten μg of the plasmid was added to 0.78 ml of DG44 cells suspended in PBS at a cell concentration of $1 \times 10^7$ cells/ml, which was subjected to pulses of 1,500 V and 25 μF capacity.

After 10 minutes of the recovery period at room temperature, the electroporated cells were suspended in a CHO—S—SFMII medium (GIBCO) containing hypoxanthine/thymidine (GIBCO), and cultured using two 96-well plates (Falcon) in a 5% $CO_2$ incubator. On the day after the start of culturing, the medium was changed to a selection medium containing the CHO—S—SFMII medium (GIBCO) containing hypoxanthine/thymidine (GIBCO) and 500 μg/ml GENETICIN (G418Sulfate, GIBCO) to select cells into which the antibody gene had been introduced. After changing the selection medium, the cells were examined under a microscope about two weeks later. After a favorable cell growth was observed, the amount of antibody produced was measured by the ELISA described below for determining antibody concentration, and cells having a high production yield of antibody were selected.

Reference Example 5

Construction of Humanized Antibody (1) Construction of Humanized Antibody H Chain
(i) Construction of the Humanized H Chain Version "a"

Humanized ATR-5 antibody H chain was generated using CDR-grafting by the PCR method. In order to generate the humanized antibody H chain version "a" having the FRs derived from human antibody L39130 (DDBJ, Gao L. et al., unpublished, 1995), seven PCR primers were used. The CDR-grafting primers hR5Hv1S (SEQ ID NO: 11), hR5Hv2S (SEQ ID NO: 12), and hR5Hv4S (SEQ ID NO: 13) have a sense DNA sequence, and the CDR grafting primers hR5Hv3A (SEQ ID NO: 14) and hR5Hv5A (SEQ ID NO: 15) have an antisense DNA sequence, each primer having a 18-35 bp complementary sequence on both ends thereof.

hR5Hv1S was designed to have the Kozak consensus sequence (Kozak, M. et al., J. Mol. Biol. 196: 947-950, 1987) and a SalI recognition site, and hR5Hv5A was designed to have a NheI recognition site. The exogenous primer hR5HvPrS (SEQ ID NO: 16) has a homology with the CDR-grafting primer hR5Hv1S, and hR5HvPrA (SEQ ID NO: 17) has a homology with the CDR-grafting primer hR5Hv5A.

The CDR-grafting primers hR5Hv1S, hR5Hv2S, hR5Hv3A, hR5Hv4S, and hR5Hv5A, and exogenous primers hR5HvPrS and hR5HvPrA were synthesized and purified by Pharmacia Biotech.

PCR was performed using the KOD DNA polymerase (Toyo Boseki) and using the attached buffer under the condition of containing 120 mM Tris-HCl (pH 8.0), 10 mM KCl, 6 mM $(NH_4)_2SO_4$, 0.1% Triton X100, 0.001% BSA, 0.2 mM dNTPs (dATP, dGTP, dCTP, dTTP), 1 mM $MgCl_2$, 2.5 units of KOD DNA polymerase (Toyo Boseki), and 5 pmole each of the CDR-grafting primers hR5Hv1S, hR5Hv2S, hR5Hv3A, hR5Hv4S, and hR5Hv5A in 98 μl, for 5 cycles at a temperature cycle of 94° C. for 30 seconds, 50° C. for 1 minute, and 72° C. for 1 minute. After further addition of 100 pmole of exogenous primers hR5HvPrS and hR5HvPrA, PCR was performed for 25 cycles in a system of 100 μl with the same temperature cycle. DNA fragments amplified by the PCR method were separated by agarose gel electrophoresis using a 2% NuSieve GTG agarose (FMC BioProducts).

The agarose strips containing about 430 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 17 μl of water. The PCR reaction mixture obtained was digested with NheI and SalI, and was ligated to the plasmid vector CVIDEC prepared by digesting with NheI and SalI, using the DNA ligation kit ver.2 (Takara Shuzo) according to the instructions attached to the kit.

The ligation mixture was added to 100 μl of *E. coli* JM109 competent cells (Nippongene) and was incubated for 30 minutes on ice and for 1 minute at 42° C. Then, 300 μl of the Hi-Competence Broth (Nippongene) was added thereto, incubated at 37° C. for 1 hour, and then the *E. coli* was plated on the LBA agar medium and incubated overnight at 37° C. to obtain an *E. coli* transformant. The transformant was cultured overnight at 37° C. in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions.

Since mutation and/or deletion were observed before or after the EcoT221 recognition site, each of fragments having the correct sequence was ligated and then subcloned again to CVIDEC to determine the nucleotide sequence. The plasmid having the correct sequence was designated as hATR5Hva/CVIDEC. The nucleotide sequence and the corresponding amino acid sequence of the humanized H chain version "a" contained in the plasmid hATR5Hva/CVIDEC are shown in SEQ ID NO: 18. The amino acid sequence of version "a" is also shown in SEQ ID NO: 19.

(ii) Construction of Humanized H Chain Versions "b" and "c"

Versions "b" and "c" were generated by replacing the FR3 of version "a" with the FR3 derived from another human antibody using the FR-shuffling method. In order to replace the FR3 in version "b" with one derived from human antibody Z34963 (DDBJ, Borretzen M. et al., Proc. Natl. Acad. Sci. USA, 91: 12917-12921, 1994), the four DNA primers encoding the FR3 were generated. The FR-shuffling primers F3RFFS (SEQ ID NO: 20) and F3RFBS (SEQ ID NO: 21) have a sense DNA sequence and F3RFFA (SEQ ID NO: 22) and F3RFBA (SEQ ID NO: 23) have an antisense DNA sequence.

F3RFFS and F3RFFA have a sequence complementary to each other, and have BalI and XhoI recognition sequences on both ends. In order to replace the FR3 in version "c" with one derived from human antibody P01825 (SWISS-PROT, Poljak R J. et al., Biochemistry, 16: 3412-3420, 1977), four DNA primers encoding the FR3 were generated. The FR-shuffling primers F3NMFS (SEQ ID NO: 24) and F3NMBS (SEQ ID NO: 25) have a sense DNA sequence and F3NMFA (SEQ ID NO: 26) and F3NMBA (SEQ ID NO: 27) have an antisense DNA sequence. F3RFBS and F3RFBA have a sequence complementary to each other, and have XhoI and NcoI recognition sequences on both ends.

F3RFFS, F3RFBS, F3RFFA, F3RFBA, F3NMFS, F3NMBS, F3NMFA, and F3NMBA were synthesized by Pharmacia Biotech. F3RFFS and F3RFFA, and F3RFBS and F3RFBA were annealed, and were digested with BalI and XhoI, and NcoI and XhoI, respectively. They were introduced to the plasmid hATR5Hva/CVIDEC (BalI/NcoI) prepared by digesting with BalI and NcoI, and the nucleotide sequence was determined. The plasmid having the correct sequence was designated as hATR5Hvb/CVIDEC. The nucleotide sequence and the corresponding amino acid sequence of the humanized H chain version "b" contained in the plasmid hATR5Hvb/CVIDEC are shown in SEQ ID NO: 28. The amino acid sequence of version "b" is also shown in SEQ ID NO: 29.

F3NMFS and F3NMFA, and F3NMBS and F3NMBA were annealed, and were digested with BalI and XhoI, and NcoI and XhoI, respectively. They were introduced to the plasmid hATR5Hva/CVIDEC (BalI/NcoI) prepared by digesting with BalI and NcoI, and the nucleotide sequence was determined. The plasmid having the correct sequence was designated as hATR5Hvc/CVIDEC. The nucleotide sequence and the corresponding amino acid sequence of the humanized H chain version "c" contained in the plasmid hATR5Hvc/CVIDEC are shown in SEQ ID NO: 30. The amino acid sequence of version "c" is also shown in SEQ ID NO: 31.

(iii) Construction of Humanized H Chain Versions "d" and "e"

Versions "d" and "e" were generated by replacing the FR3 of version "a" with the FR3 derived from another human antibody using the FR-shuffling method. In order to replace the FR3 in version "d" with one derived from human antibody M62723 (DDBJ, Pascual V. et al., J. Clin. Invest., 86: 1320-1328, 1990), four DNA primers encoding the FR3 were generated. The FR-shuffling primer F3EPS (SEQ ID NO: 32) has a sense DNA sequence and F3EPA (SEQ ID NO: 33) has an antisense DNA sequence, and the 3'-end of the primers has a complementary sequence of 18 bp.

Exogenous primers F3PrS (SEQ ID NO: 34) and F3PrA (SEQ ID NO: 35) have a homology with the FR-shuffling primers F3EPS and F3EPA, and can also be used for other FR3's FR-shuffling. In order to replace the FR3 in version "e" with one derived from the human antibody Z80844 (DDBJ, Thomsett A R. et al., unpublished), two DNA primers encoding the FR3 were generated. The FR-shuffling primers F3VHS (SEQ ID NO: 36) has a sense DNA sequence and F3VHA (SEQ ID NO: 37) has an antisense DNA sequence, and the 3'-end of the primers has a complementary sequence of 18 bp. F3EPS, F3EPA, F3PrS, F3PrA, F3VHS and F3VHA were synthesized by Pharmacia Biotech.

PCR was performed using the KOD DNA polymerase (Toyo Boseki) using the attached buffer under the condition of containing 5 μl each of 1 μM FR-shuffling primers F3EPS and F3EPA, or F3VHS and F3VHA, 0.2 mM dNTPs, 1.0 mM $MgCl_2$, and 2.5 units of KOD DNA polymerase in 100 μl of the reaction mixture, for 5 cycles at a temperature cycle of 94° C. for 30 seconds, 50° C. for 1 minute, and 74° C. for 1 minute. After further addition of 100 pmole of exogenous primers F3PrS and F3PrA, PCR was performed for 25 cycles with the same temperature cycle.

DNA fragments amplified by the PCR method were separated by agarose gel electrophoresis using a 2% Nu Sieve GTG agarose (FMC BioProducts). The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 μl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined.

The plasmids having the correct sequence were designated as hATR5Hvd/CVIDEC and hATR5Hve/CVIDEC. The nucleotide sequence and the corresponding amino acid sequence of the humanized H chain version "d" contained in the plasmid hATR5Hvd/CVIDEC are shown in SEQ ID NO: 38, and the amino acid sequence of version "d" is also shown in SEQ ID NO: 39. The nucleotide sequence and the corresponding amino acid sequence of the humanized H chain version "e" contained in the plasmid hATR5Hve/CVIDEC are shown in SEQ ID NO: 40, and the amino acid sequence of version "e" is also shown in SEQ ID NO: 41.

(iv) Construction of Humanized H Chain Versions "f" and "g"

Versions "f" and "g" were generated by replacing the FR3 of version "a" with the FR3 derived from another human antibody using the FR-shuffling method. In order to replace the FR3 in version "f" with one derived from human antibody L04345 (DDBJ, Hillson J L. et al., J. Exp. Med., 178: 331-336, 1993) and to replace the FR3 in version "g" with one derived from human antibody S78322 (DDBJ, Bejcek B E. et al., Cancer Res., 55: 2346-2351, 1995), two primers each encoding the FR3 were synthesized. The FR-shuffling primer F3SSS (SEQ ID NO: 42) of version "f" has a sense DNA sequence and F3SSA (SEQ ID NO: 43) has an antisense DNA sequence, and the 3'-end of the primers has a complementary sequence of 18 bp.

F3CDS (SEQ ID NO: 44) of version "g" has a sense DNA sequence and F3CDA (SEQ ID NO: 45) has an antisense DNA sequence, and the 3'-end of the primers has a complementary sequence of 18 bp. F3SSS, F3SSA, F3CDS, and F3CDA were synthesized and purified by Pharmacia Biotech. PCR was performed using the KOD DNA polymerase (Toyo Boseki) using the attached buffer under the condition of containing 5 µl each of 1 µM FR-shuffling primers F3SSS and F3SSA, or F3CDS and F3CDA, 0.2 mM dNTPs, 1.0 mM MgCl₂, and 2.5 units of KOD DNA polymerase in 100 µl of the reaction mixture, for 5 cycles at a temperature cycle of 94° C. for 30 seconds, 50° C. for 1 minute, and 74° C. for 1 minute. After further addition of 100 pmole of exogenous primers F3PrS and F3PrA, PCR was performed for 25 cycles with the same temperature cycle.

DNA fragments amplified by the PCR method were separated by agarose gel electrophoresis using a 2% NuSieve GTG agarose (FMC BioProducts). The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 µl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined.

The plasmids having the correct sequence were designated as hATR5Hvf/CVIDEC and hATR5Hvg/CVIDEC. The nucleotide sequence and the corresponding amino acid sequence of the humanized H chain version "f" contained in the plasmid hATR5Hvf/CVIDEC, and the amino acid sequence of version "f" are shown in SEQ ID NO: 46 and 47. The nucleotide sequence and the corresponding amino acid sequence of the humanized H chain version "g" contained in the plasmid hATR5Hvg/CVIDEC, and the amino acid sequence of version "g" are shown in SEQ ID NO: 48 and 49.

(v) Construction of the Humanized H Chain Version "h"

Version "h" was generated by replacing the FR3 of version "a" with the FR3 derived from another human antibody using the FR-shuffling method. In order to replace the FR3 in version "h" with one derived from the human antibody Z26827 (DDBJ, van Der Stoep et al., J. Exp. Med., 177: 99-107, 1993), two primers each encoding the FR3 were synthesized. The FR-shuffling primer F3ADS (SEQ ID NO: 50) of version "h" has a sense DNA sequence and F3ADA (SEQ ID NO: 51) has an antisense DNA sequence, and the 3'-end of the primers has a complementary sequence of 18 bp.

F3ADS and F3ADA were synthesized and purified by Pharmacia Biotech. PCR was performed using the KOD DNA polymerase (Toyo Boseki) using the attached buffer under the condition of containing 5 µl each of 1 µl FR-shuffling primers F3ADS and F3ADA, 0.2 mM dNTPs, 1.0 mM MgCl₂, and 2.5 units of KOD DNA polymerase in 100 µl of the reaction mixture, for 5 cycles at a temperature cycle of 94° C. for 30 seconds, 50° C. for 1 minute, and 74 C for 1 minute. After further addition of 100 pmole of exogenous primers F3PrS and F3PrA, PCR was performed for 25 cycles with the same temperature cycle. DNA fragments amplified by the PCR method were separated by agarose gel electrophoresis using a 2% NuSieve GTG agarose (FMC BioProducts).

The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 µl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined. The plasmids having the correct sequence were designated as hATR5Hvh/CVIDEC. The nucleotide sequence and the corresponding amino acid sequence of the humanized H chain version "h" contained in the plasmid hATR5Hvh/CVIDEC, and the amino acid sequence of version "h" are shown in SEQ ID NO: 52. The amino acid sequence of version "h" is shown in SEQ ID NO: 53.

(vi) Construction of Humanized H Chain Versions "i" and "j"

Versions "i" and "j" were generated by replacing the FR3 of version "a" with the FR3 derived from another human antibody using the FR-shuffling method. In order to replace the FR3 in version "i" with one derived from the human antibody U95239 (DDBJ, Manheimer-Lory A A J., unpublished) and to replace the FR3 in version "j" with one derived from the human antibody L03147 (DDBJ, Collect T A. et al., Proc. Natl. Acad. Sci. USA, 89: 10026-10030, 1992), two primers each encoding the FR3 were synthesized. The FR-shuffling primer F3MMS (SEQ ID NO: 54) of version "i" has a sense DNA sequence and F3MMA (SEQ ID NO: 55) has an antisense DNA sequence, and the 3'-end of the primers has a complementary sequence of 18 bp.

F3BMS (SEQ ID NO: 56) of version "j" has a sense DNA sequence and F3BMA (SEQ ID NO: 57) has an antisense DNA sequence, and the 3'-end of the primers has a complementary sequence of 18 bp. F3MMS, F3MMA, F3BMS, and F3BMA were synthesized and purified by Pharmacia Biotech. PCR was performed using the Ampli Taq Gold (Perkin-Elmer) using the attached buffer under the condition of containing 5 µl each of 1 µM FR-shuffling primers F3MMS and F3MMA, or F3BMS and F3BMA, 0.2 mM dNTPs, 1.0 mM MgCl₂, and 2.5 units of Ampli Taq Gold in 100 µl of the reaction mixture, for 5 cycles at a temperature cycle of 94° C. for 30 seconds, 50° C. for 1 minute, and 74° C. for 1 minute. After further addition of 100 pmole of exogenous primers F3PrS and F3PrA, PCR was performed for 25 cycles with the same temperature cycle.

DNA fragments amplified by the PCR method were separated by agarose gel electrophoresis using a 2% Nu Sieve GTG agarose (FMC BioProducts). The agarose strips containing about 424 bp long DNA fragments were excised, to which 3 volumes (ml/g) of TE was added, and then were extracted with phenol, phenol/chloroform, and chloroform to purify the DNA fragments. After precipitating the purified DNA with ethanol, one third the volume thereof was dissolved in 14 µl of water. The PCR reaction mixture obtained was digested with BalI and NcoI, and was introduced to the plasmid hATR5Hva/CVIDEC (BalI/NcoI) prepared by digesting with BalI and NcoI, and the nucleotide sequence was determined.

The plasmids having the correct sequence were designated as hATR5Hvi/CVIDEC and hATR5Hvj/CVIDEC. The nucleotide sequence and the corresponding amino acid sequence of the humanized H chain version "i" contained in the plasmid hATR5Hvi/CVIDEC, and the amino acid sequence of version "i" are shown in SEQ ID NO: 58 and 59. The nucleotide sequence and the corresponding amino acid sequence of the humanized H chain version "j" contained in the plasmid hATR5Hvj/CVIDEC, and the amino acid sequence of version "j" are shown in SEQ ID NO: 60 and 61.

(vii) Construction of Humanized H Chain Versions "b1" and "d1"

Versions "b1" and "d1" were generated by replacing the FR2 of versions "b" and "d" with the FR2 derived from another human antibody using the FR-shuffling method. In order to replace the FR2 with one derived from the human antibody P01742 (SWISS-PROT, Cunningham B A. et al., Biochemistry, 9: 3161-3170, 1970), two DNA primers encoding the FR2 were synthesized. The FR-shuffling vector F2MPS (SEQ ID NO: 62) has a sense DNA sequence and F2MPA (SEQ ID NO: 63) has an antisense DNA sequence. They also have a sequence complementary to each other, and have recognition sequences of EcoT22I and BalI on both ends thereof.

F2MPS and F2MPA were synthesized and purified by Pharmacia Biotech. F2MPS and F2MPA were annealed and were digested with EcoT22I and BalI. They were introduced to plasmids hATR5Hvb/CVIDEC (EcoT22I/BalI) and hATR5Hvd/CVIDEC (EcoT22I/BalI) prepared by digesting with EcoT22I and BalI, and the nucleotide sequence was determined. The plasmids having the correct sequence were designated as hATR5Hvb1/CVIDEC and hATR5Hvd1/CVIDEC. The nucleotide sequence and the corresponding amino acid sequence of the humanized H chain version "b1" contained in the plasmid hATR5Hvb1/CVIDEC, and the amino acid sequence of version "b1" are shown in SEQ ID NO: 64 and 65. The nucleotide sequence and the corresponding amino acid sequence of the humanized H chain version "d1" contained in the plasmid hATR5Hvd1/CVIDEC, and the amino acid sequence of version "d1" are shown in SEQ ID NO: 66 and 67.

(viii) Construction of Humanized H Chain Versions "b3" and "d3"

Versions "b3" and "d3" were generated by replacing the FR2 of versions "b" and "d" with the FR2 derived from another human antibody using the FR-shuffling method. In order to replace the FR2 with one derived from the human antibody Z80844 (DDDJ, Thomsett A R. et al., unpublished), two DNA primers encoding the FR2 were synthesized. The FR-shuffling vector F2VHS (SEQ ID NO: 68) has a sense DNA sequence and F2VHA (SEQ ID NO: 69) has an antisense DNA sequence. They also have a sequence complementary to each other, and have recognition sequences of EcoT22I and BalI on both ends thereof. The synthesis and purification of F2VHS and F2VHA was referred to Pharmacia Biotech.

F2VHS and F2VHA were annealed and were digested with EcoT22I and BalI. They were introduced to plasmids hATR5Hvb/CVIDEC (EcoT22I/BalI) and hATR5Hvd/CVIDEC (EcoT22I/BalI) prepared by digesting with EcoT22I and BalI, and the nucleotide sequence was determined. The plasmids having the correct sequence were designated as hATR5Hvb3/CVIDEC and hATR5Hvd3/CVIDEC. The nucleotide sequence and the corresponding amino acid sequence of the humanized H chain version "b3" contained in the plasmid hATR5Hvb3/CVIDEC, and the amino acid sequence of version "b3" are shown in SEQ ID NO: 70 and 71. The nucleotide sequence and the corresponding amino acid sequence of the humanized H chain version "d3" contained in the plasmid hATR5Hvd3/CVIDEC, and the amino acid sequence of version "d3" are shown in SEQ ID NO: 72 and 73.

(2) Construction of a Humanized Antibody L Chain V Region (i) Version "a"

The humanized ATR-5 antibody L chain V region was generated by the CDR-grafting using the PCR method. For the generation of a humanized antibody L chain (version "a") having framework regions derived from human antibody Z37332 (DDBJ, Welschof M. et al., J. Immunol. Methods, 179: 203-214, 1995), seven PCR primers were used.

CDR-grafting primers h5Lv1S (SEQ ID NO: 74) and h5Lv4S (SEQ ID NO: 75) have a sense DNA sequence, CDR-grafting primers h5Lv2A (SEQ ID NO: 76), h5Lv3A (SEQ ID NO: 77), and h5Lv5A (SEQ ID NO: 78) have an antisense DNA sequence, and each primer has 20 bp complementary sequences on both ends thereof. Exogenous primers h5LvS (SEQ ID NO: 79) and h5LvA (SEQ ID NO: 80) have a homology with CDR-grafting primers h5Lv1S and h5Lv5A. The synthesis and purification of CDR-grafting primers h5Lv1S, h5Lv4S, h5Lv2A, h5Lv3A, h5Lv5A, h5LvS, and h5LvA were referred to Pharmacia Biotech.

The PCR solutions contain, in 100 µl, 120 mM Tris-HCl (pH 8.0), 10 mM KCl, 6 mM $(NH_4)_2SO_4$, 0.1% Triton X-100, 0.001% BSA, 0.2 mM dNTPs (dATP, dGTP, dCTP, dTTP), 1 mM $MgCl_2$, 2.5 units of KOD DNA polymerase (Toyo Boseki), 50 pmole of the CDR-grafting primers h5Lv1S, h5Lv2A, h5Lv3A, h5Lv4S, and h5Lv5A.

PCR was performed using the DNA Thermal Cycler 480 (Perkin-Elmer) for 5 cycles with the temperature cycle of 94° C. for 30 seconds, 50° C. for 1 minute, and 72° C. for 1 minute to assemble 5 CDR-grafting primers. After further addition of 100 pmole of exogenous primers h5LvS and h5LvA to the reaction mixture, PCR was performed for 30 cycles with the temperature cycle of 94° C. for 30 seconds, 52° C. for 1 minute, and 72° C. for 1 minute to amplify the assembled DNA fragments.

The PCR reaction mixture was separated by agarose gel electrophoresis using a 3% NuSieve GTG agarose (FMC BioProducts), and the agarose strips containing about 400 bp long DNA fragments were excised. The agarose strips were extracted with phenol and chloroform, DNA fragments were recovered by ethanol precipitation. The recovered DNA fragments were digested with the restriction enzymes SplI (Takara Shuzo) and BglII (Takara Shuzo) at 37° C. for 4 hours. The digestion mixture was extracted with phenol and chloroform, and after the ethanol precipitation of the DNA fragments, they were dissolved in 10 µl of TE. The SplI-BglII DNA fragment prepared as above encoding the humanized L chain V region and the CVIDEC vector prepared by digesting with SplI and BglII were ligated using the DNA ligation kit ver.2 (Takara Shuzo) by reacting at 16° C. for 1 hour according to the instructions attached to the kit.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on the LBA agar medium and incubated overnight at 37° C. to obtain an *E. coli* transformant. The transformant was cultured overnight in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions. The plasmid that contains the gene encoding the humanized antibody L chain V region and that has a BglII recognition sequence and the Kozak sequence at the 5'-end, and a SplI recognition sequence at the 3'-end was designated as hATR5Lva/CVIDEC. The nucleotide sequence (including the corresponding amino acid sequence) of the humanized L chain version "a" is shown in SEQ ID NO: 81. The amino acid sequence of version "a" is also shown in SEQ ID NO: 82.

(ii) Versions "b" and "c"

Versions "b" and "c" were generated by replacing (FR-shuffling) the FR3 of version "a". For version "b" the FR3 derived from human antibody S68699 (DDBJ, Hougs L. et al., Exp. Clin. Immunogen et., 10: 141-151, 1993) was used, and for version "c" the FR3 derived from human antibody P01607 (SWISS-PROT, Epp O et al., Biochemistry, 14: 4943-4952, 1975) was used, respectively.

Primers F3SS (SEQ ID NO: 83) and F3SA (SEQ ID NO: 84) encoding the FR3 of version "b", or primers F3RS (SEQ ID NO: 85) and F3RA (SEQ ID NO: 86) encoding the FR3 of version "c" have a sequence complementary to each other, and have the recognition sequences of the restriction enzymes KpnI and PstI on both ends thereof. The synthesis and purification of F3SS, F3SA, F3RS, and F3RA were referred to Pharmacia Biotech. 100 pmole each of F3SS and F3SA, or F3RS and F3RA were annealed by treating at 96° C. for 2 minutes and at 50° C. for 2 minutes and the double stranded DNA fragments were generated.

These double stranded DNA fragments were digested with the restriction enzyme KpnI (Takara Shuzo) at 37° C. for 1 hour, and then with the restriction enzyme PstI (Takara Shuzo) at 37° C. for 1 hour. The digestion mixture was extracted with phenol and chloroform, and after it was precipitated with ethanol, it was dissolved in TE.

The plasmid hATR5Lva/CVIDEC was digested with the restriction enzyme KpnI (Takara Shuzo) at 37° C. for 1 hour, and then with the restriction enzyme PstI (Takara Shuzo) at 37° C. for 1 hour. The digestion mixture was separated by agarose gel electrophoresis using a 1.5% NuSieve GTG agarose (FMC BioProducts), and the agarose strips having about 3000 bp long DNA fragments were excised. The agarose strip was extracted with phenol and chloroform, and after the DNA fragments were precipitated with ethanol, they were dissolved in TE.

The KpnI-PstI DNA fragment prepared as above encoding the FR3 of versions "b" or "c" and the hATR5Lva/CVIDEC vector in which the FR3 was removed by digesting with KpnI and PstI were ligated using the DNA ligation kit ver.2 (Takara Shuzo) by reacting at 16° C. for 1 hour according to the instructions attached to the kit.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on the LBA agar medium and incubated overnight at 37° C. to obtain an *E. coli* transformant. The transformant was cultured overnight in 3 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions.

The plasmids that contain the gene encoding version "b" or version "c" in which the FR3 of humanized antibody L chain version "a" was replaced was designated as hATR5Lvb/CVIDEC or hATR5Lvc/CVIDEC, respectively. The nucleotide sequence and the corresponding amino acid sequence of the humanized L chain version "b" contained in plasmid hATR5Lvb/CVIDEC and the amino acid sequence of version "b" are shown in SEQ ID NO: 87 and 88. The nucleotide sequence and the corresponding amino acid sequence of the humanized L chain version "c" contained in plasmid hATR5Lvc/CVIDEC and the amino acid sequence of version "c" are shown in SEQ ID NO: 89 and 90.

(iii) Versions "b1" and "b2"

Versions "b1" and "b2" were generated by replacing the FR2 of version "b". For version "b1" the FR2 derived from human antibody S65921 (DDBJ, Tonge D W et al., Year Immunol., 7: 56-62, 1993) was used, and for version "b2" the FR2 derived from human antibody X93625 (DDBJ, Cox J P et al., Eur. J. Immunol., 24: 827-836, 1994) was used, respectively.

Primers F2SS (SEQ ID NO: 91) and F2SA (SEQ ID NO: 92) encoding the FR2 of version "b1", or primers F2XS (SEQ ID NO: 93) and F2XA (SEQ ID NO: 94) encoding the FR2 of version "b2" have a sequence complementary to each other, and have the recognition sequences of the restriction enzymes AflII and SpeI on both ends thereof. F2SS, F2SA, F2XS, and F2XA were synthesized by Pharmacia Biotech. 100 pmole each of F2SS and F2SA, or F2XS and F2XA were annealed by treating at 96° C. for 2 minutes and at 50° C. for 2 minutes, and the double stranded DNA fragments were generated.

These double stranded DNA fragments were digested with the restriction enzymes AflII (Takara Shuzo) and SpeI (Takara Shuzo) at 37° C. for 1 hour. The digestion mixture was extracted with phenol and chloroform, and after the DNA fragments were precipitated with ethanol, they were dissolved in TE.

The plasmid hATR5Lvb/CVIDEC was digested with the restriction enzymes AflII (Takara Shuzo) and SpeI (Takara Shuzo) at 37° C. for 1 hour. The digestion mixture was separated by agarose gel electrophoresis using a 1.5% NuSieve GTG agarose (FMC BioProducts), and the agarose strips having about 3000 bp long DNA fragments were excised. The agarose strip was extracted with phenol and chloroform, and after the DNA fragments were precipitated with ethanol, they were dissolved in TE.

The AflII-SpeI DNA fragment prepared as above encoding the FR2 of version "b1" or "b2" and the hATR5Lvb/CVIDEC vector in which the FR2 was removed by digesting with AflII and SpeI were ligated using the DNA ligation kit ver.2 (Takara Shuzo) by reacting at 16° C. for 1 hour according to the instructions attached to the kit.

The ligation mixture was added to 100 µl of *E. coli* JM109 competent cells (Nippongene) and was incubated for 30 minutes on ice and for 1 minute at 42° C. Then, 300 µl of the Hi-Competence Broth (Nippongene) was added thereto, incubated at 37° C. for 1 hour, and then the *E. coli* was plated on the LBA agar medium and incubated overnight at 37° C. to obtain an *E. coli* transformant. The transformant was cultured overnight at 37° C. in 4 ml of the LBA medium, and from the cell fractions, plasmid DNA was prepared using the QIAprep Spin Plasmid Kit (QIAGEN).

The nucleotide sequence of the cDNA coding region in the plasmid was determined using the Dye Terminator Cycle Sequencing FS Ready Reaction Kit (Perkin-Elmer) by the DNA Sequencer 373A (Perkin-Elmer). As the sequencing primer, M13 Primer M4 (Takara Shuzo) and M13 Primer RV (Takara Shuzo) were used, and the sequence was determined by confirming the nucleotide sequence in both directions.

The plasmids that contain the gene encoding version "b1" or "b2" in which the FR2 of humanized antibody L chain version "b" was replaced was designated as hATR5Lvb1/CVIDEC and hATR5Lv2/CVIDEC, respectively. The nucleotide sequence and the corresponding amino acid sequence of the humanized L chain version "b1" contained in plasmid hATR5Lvb1/CVIDEC and the amino acid sequence of version "b1" are shown in SEQ ID NO: 95 and 96. The nucleotide sequence and the corresponding amino acid sequence of the humanized L chain version "b2" contained in plasmid hATR5Lvb2/CVIDEC and the amino acid sequence of version "b2" are shown in SEQ ID NO: 97 and 98.

(3) Construction of the Expression Vector of Humanized Antibody (i) Combination of Humanized H Chain and Chimeric L Chain The plasmid hATR5Hva/CVIDEC containing a H chain V region was digested with NheI and SalI, and a cDNA fragment of the humanized H' chain V region was recovered and introduced to chATR5/N5KG4P (SalI/NheI) prepared by digesting chATR5/N5KG4P, a chATR-5 antibody expression plasmid vector, with NheI and SalI. The plasmid thus generated was designated as hHva-chLv/N5KG4P.

The plasmid hATR5Hvb/CVIDEC containing a H chain V region was digested with NheI and SalI, and a cDNA fragment of the humanized H chain V region was recovered and introduced to chATR5/N5KG4P (SalI/NheI) prepared by digesting chATR5/N5KG4P, a chATR-5 antibody expression plasmid vector, with NheI and SalI. The plasmid thus generated was designated as hHvb-chLv/N5KG4P.

The plasmids hATR5Hvc/CVIDEC, hATR5Hvd/CVIDEC, and hATR5Hve/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR-5 antibody expression plasmid vector, with NheI and SalI. The plasmids thus generated were designated as hHvc-chLv/N5KG4P, hHvd-chLv/N5KG4P, and hHve-chLv/N5KG4P.

The plasmids hATR5Hvf/CVIDEC and hATR5Hvh/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR-5 antibody expression plasmid vector, with NheI and SalI. The plasmids thus generated were designated as hHvf-chLv/N5KG4P and hHvh-chLv/N5KG4P.

The plasmids hATR5Hvi/CVIDEC and hATR5Hvj/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR-5 antibody expression plasmid vector, with NheI and SalI.

The plasmids thus generated were designated as hHvi-chLv/N5KG4P and hHvj-chLv/N5KG4P.

The plasmids hATR5Hb1/CVIDEC and hATR5Hvd1/CVIDEC containing a H chain V region were digested with NheI and SalI, and cDNA fragments of the humanized H chain V region were recovered and introduced to chATR5/N5KG4P (SalI/NheI) prepared by digesting chATR5/N5KG4P, a chATR-5 antibody expression plasmid vector, with NheI and SalI. The plasmids thus generated were designated as hHvb1-chLv/N5KG4P and hHvd1-chLv/N5KG4P.

(ii) Combination of Humanized L Chain Ad Chimeric H Chain

Using an antibody expression vector N5KG4P, it was combined with a chimeric H chain and was expressed, and the humanized L chain was evaluated.

The plasmids hATR5Lva/CVIDEC, hATR5Lvb/CVIDEC, hATR5Lvc/CVIDEC, hATR5Lvb1/CVIDEC, and hATR5Lvb2/CVIDEC were digested with the restriction enzymes BglII (Takara Shuzo) and SpII (Takara Shuzo) at 37° C. for 2-3 hours. The digestion mixture was separated by agarose gel electrophoresis using a 1.5% or 2% NuSieve GTG agarose (FMC BioProducts), and the agarose strips having about 400 bp long DNA fragments were excised. The agarose strips were extracted with phenol and chloroform, and after the DNA fragments were precipitated with ethanol, they were dissolved in TE.

The SplI-BglII DNA fragment containing the gene encoding the a humanized L chain V region of each of these versions and the hATR5Hv/N5KG4P digested with SplI and BglII were ligated using the DNA ligation kit ver.2 (Takara Shuzo) by reacting at 16° C. for 1 hour according to the instructions attached to the kit.

The ligation mixture was added to 100 µl of E. coli JM109 competent cells (Nippongene) and was incubated for 30 minutes on ice and for 1 minute at 42° C. Then, 300 of the Hi-Competence Broth (Nippongene) was added thereto, incubated at 37° C. for 1 hour, and then the E. coli was plated on the LBA agar medium and incubated overnight at 37° C. to obtain an E. coli transformant.

The transformant was cultured overnight at 37° C. in 250 ml or 500 ml of the LBA medium, and from the cell fractions, plasmid DNA was prepared using the Plasmid Maxi Kit (QIAGEN). The plasmids in which a gene encoding the chimeric H chain and humanized L chain was introduced were designated as chHv-hLva/N5KG4P, chHv-hLvb/N5KG4P, chHv-hLvc/N5KG4P, chHv-hLvb1/N5KG4P, and chHv-hLvb2/N5KG4P.

(iii) Combination of Humanized H Chain and Humanized L Chain

The plasmid hATR5Hva/CVIDEC containing a H chain V region was digested with NheI and SaiI, and a cDNA fragment of the humanized H chain V region was recovered and introduced to hLva/N5KG4P (SalI/NheI) prepared by digesting plasmid chHv-hLva/N5KG4P containing the cDNA sequence of humanized ATR-5 antibody L chain version "a" with NheI and SalI. The plasmid thus generated was designated as hHva-hLva/N5KG4P.

The plasmids hATR5Hvb/CVIDEC and hATR5Hvc/CVIDEC containing a H chain V region were digested with NheI and SalI, and cDNA fragments of the humanized H chain V region were recovered and introduced to hLva/N5KG4P (SalI/NheI) prepared by digesting plasmid chHv-hLva/N5KG4P containing the cDNA sequence of humanized ATR-5 antibody L chain version "a" with NheI and SaiI. The plasmids thus generated were designated as hHvb-hLva/N5KG4P and hHvc-hLva/N5KG4P.

The plasmids hATR5Hvb/CVIDEC, hATR5Hvd/CVIDEC, and hATR5Hve/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvb-hLvb/N5KG4P, hHvd-hLvb/N5KG4P, and hHve-hLvb/N5KG4P.

The plasmids hATR5Hvf/CVIDEC, hATR5Hvg/CVIDEC, and hATR5Hvh/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvf-hLvb/N5KG4P, hHvg-hLvb/N5KG4P, and hHvh-hLvb/N5KG4P.

The plasmids hATR5Hvi/CVIDEC and hATR5Hvj/CVIDEC containing a H chain V region were digested with NheI and SalI, and cDNA fragments of the humanized H chain V region were recovered and introduced to hLvb/

N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvi-hLvb/N5KG4P and hHvj-hLvb/N5KG4P.

The plasmids hATR5Hvb1/CVIDEC and hATR5Hvd1/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvb1-hLvb/N5KG4P and hHvd1-hLvb/N5KG4P.

The plasmids hATR5Hvb3/CVIDEC and hATR5Hvd3/CVIDEC containing a H chain V region were digested with NheI and SalI, and cDNA fragments of the humanized H chain V region were recovered and introduced to hLvb/N5KG4P (SalI/NheI) prepared by digesting plasmid chHv-hLvb/N5KG4P containing the cDNA sequence of humanized ATR-5 antibody L chain version "b" with NheI and SalI. The plasmids thus generated were designated as hHvb3-hLvb/N5KG4P and hHvd3-hLvb/N5KG4P.

The plasmid hATR5Hvb/CVIDEC containing a H chain V region was digested with NheI and SalI, and a cDNA fragment of the humanized H chain V region was recovered and introduced to hLvb1/N5KG4P (SalI/NheI) and hLvb2/N5KG4P (SalI/NheI) prepared by digesting plasmids chHv-hLvb1/N5KG4P and chHv-hLvb2/N5KG4P containing the cDNA sequence of humanized ATR-5 antibody L chain versions "b1" and "b2" with NheI and SalI. The plasmids thus generated were designated as hHvb-hLvb1/N5KG4P and hHvb-hLvb2/N5KG4P.

The plasmid hATR5Hvi/CVIDEC containing a H chain V region was digested with NheI and SalI, and a cDNA fragment of the humanized H chain V region was recovered and introduced to hLvb1/N5KG4P (SalI/NheI) and hLvb2/N5KG4P (SalI/NheI) prepared by digesting plasmids chHv-hLvb1/N5KG4P and chHv-hLvb2/N5KG4P containing the cDNA sequence of humanized ATR-5 antibody L chain versions "b1" and "b2" with NheI and SalI. The plasmids thus generated were designated as hHvi-hLvb1/N5KG4P and hHvi-hLvb2/N5KG4P.

(4) Transfection Into COS-7 Cells

In order to evaluate the activity of binding to the antigen and neutralizing activity of humanized antibody, the above antibody was transiently expressed in COS-7 cells.

The constructed expression plasmid vector was transduced into COS-7 cells by electroporation using the Gene Pulser instrument (Bio Rad). Fifty µg or 20 µg of the plasmid was added to 0.78 ml of COS-7 cells suspended in PBS at a cell concentration of $1 \times 10^7$ cells/ml, which was subjected to pulses of 1,500 V and 25 µF capacity.

After 10 minutes of the recovery period at room temperature, the electroporated cells were suspended in a DMEM medium (GIBCO) containing 5% Ultra low IgG fetal bovine serum (GIBCO), and cultured using a 10 cm culture dish or 15 cm culture dish in a 5% $CO_2$ incubator. After culturing for 24 hours, the culture supernatant was aspirated off, and then a serum-free medium HBCHO (Irvine Scientific) was added. After further culturing for 72 hours or 96 hours, the culture supernatant was collected and centrifuged to remove cell debris.

(5) Purification of Antibody

From the culture supernatant of the COS-7 cells, the antibody was purified using the AffiGel Protein A MAPSII kit (Bio Rad) or the rProtein A Sepharose Fast Flow (Pharmacia Biotech). Purification using the AffiGel Protein A MAPSII kit was carried out according to the instructions attached to the kit. Purification using the rProtein A Sepharose Fast Flow was carried out as follows:

One ml of rProtein A Sepharose Fast Flow was filled into a column and the column was equilibrated by 10 volumes of TBS. The culture supernatant of COS-7 cells was applied to the equilibrated column, which was then washed with 10 volumes of TBS. The adsorbed antibody fraction was eluted by 13.5 ml of 2.5 mM HCl (pH 3.0). The eluate was neutralized by adding 1.5 ml of 1 M Tris-HCl (pH 8.0).

By performing ultrafiltration two or three times for the purified antibody fraction using the Centriprep 30 or 100 (amicon), the solvent was replaced to TBS, and was finally concentrated to about 1.5 ml.

Reference Example 6

Antibody Quantitation and Activity Evaluation (1) Measurement of Antibody Concentration by ELISA ELISA plates for measurement of antibody concentration were prepared as follows: Each well of a 96-well ELISA plate (Maxisorp, NUNC) was immobilized by 100 µl of goat anti-human IgGγ antibody (BIO SOURCE) prepared to a concentration of 1 µg/ml in the immobilization buffer (0.1 M $NaHCO_3$, 0.02% $NaN_3$, pH 9.6) (hereinafter referred to as CB). After blocking with 200 µl of the dilution buffer (50 mM Tris-HCl, 1 mM $MgCl_2$, 0.1 M NaCl, 0.05% Tween 20, 0.02% $NaN_3$, 1% bovine serum albumin (BSA), pH 8.1) (hereinafter referred to as DB), the culture supernatant of the COS-7 cells in which antibody was expressed or purified antibody were serially diluted with DB, and then added to each well.

After incubating at room temperature for 1 hour followed by washing with the Dulbecco PBS containing 0.05% Tween 20 (hereinafter referred to as RB), 100 µl of alkaline phosphatase-conjugated goat anti-human IgGγ antibody (Biosource) which was diluted 1000-fold with DB was added. After incubating at room temperature for 1 hour followed by washing with the RB, Sigma104 (p-nitrophenyl phosphate, SIGMA) dissolved in the substrate buffer (50 mM $NaHCO_3$, 10 mM $MgCl_2$, pH 9.8) to 1 mg/ml was added, and then the absorbance at 405/655 nm was measured using the Microplate Reader (Bio Rad). As the standard for the measurement of concentration, IgG4κ (Binding Site) was used.

(2) Measurement of the Activity of Binding to the Antigen

Cell ELISA plates for measurement of antigen binding were prepared as follows. Cells used were human bladder carcinoma cells J82 (ATCC HTB-1). To 60 wells of a 96-well cell culture plate, $1 \times 10^5$ J82 cells were inoculated. This was cultured (RPMI1640 medium containing 10% fetal bovine serum (GIBCO)) for one day in a $CO_2$ incubator to allow the cells to be attached thereto. After discarding the culture liquid, each well was washed twice with 300 µl PBS. 100 µl of PBS containing 4% paraformaldehyde (hereinafter referred to as PFA/PBS) was added to each well, and placed on ice for 10 minutes to immobilize the cells.

PFA/PBS was discarded, and each well was washed twice with 300 µl of PBS, and then blocked with 250 µl of DB. The culture supernatant or purified antibody was serially diluted with DB, 100 µl of which was added to each well. After incubating at room temperature for 2 hours followed by washing with RB, 100 µl of alkaline phosphatase-conjugated goat anti-human IgGγ antibody (BioSource) diluted 1000-fold with DB was added. After incubating for 1 hour followed by washing with RB, the substrate solution was added, and then absorbance at 405/655 nm was measured using the Microplate Reader (Bio-Rad).

(3) Measurement of Neutralizing Activity

The neutralizing activity of mouse antibody, chimeric antibody, and humanized antibody was measured with the inhibiting activity against the Factor Xa-production activity by human placenta-derived thromboplastin, Thromborel S (Boehringer AG), as an index. Thus, 60 μl of the buffer (TBS containing 5 mM $CaCl_2$ and 0.1% BSA) was added to 10 μl of 1.25 mg/ml Thromborel S and 10 μl of appropriately diluted antibody, which was then incubated in a 96-well plate at room temperature for 1 hour. Ten μl each of 3.245 μg/ml human Factor X (Celsus Laboratories) and 82.5 ng/ml human Factor VIIa (Enzyme Research) were added thereto, and then were incubated at room temperature for 1 hour.

Ten μl of 0.5 M EDTA was added to stop the reaction, to which 50 μl of the chromogenic substrate solution was added and the absorbance at 405/655 nm was determined using the Microplate Reader (Bio Rad). After reacting at room temperature for 1 hour, the absorbance at 405/655 nm was determined again. The neutralizing activity may be determined by calculating the residual activity (%) from each change in absorbance with the hourly absorbance change at no antibody addition as a 100% activity.

The chromogenic substrate solution was prepared by dissolving the Testzyme chromogenic substrate S-2222 (Chromogenix) according to the attached instructions, diluting 2-fold with purified water and mixing with a polybrene solution (0.6 mg/ml hexadimethylene bromide, SIGMA) at 1:1.

(4) Evaluation of Activity (i) Combination of the Humanized H Chain Version "a" and a Chimeric L Chain An antibody (a-ch) which is the humanized H chain version "a" combined with a chimeric L chain was generated, and was tested for the binding activity to the antigen by the cell ELISA. The amount bound to the antigen was found to be decreased at the high concentration. The neutralizing activity against the antigen by FXa production-inhibition was weak as compared that of to the positive control chimeric antibody (ch-ch). Therefore, it was decided to perform the version-up of the humanized H chain by FR-shuffling. The chimeric antibody used herein was the one that was expressed in COS-7 cells, purified, and evaluated.

(ii) Combination of the Humanized L Chain Version "a" and a Chimeric H Chain

An antibody (ch-a) which is the humanized L chain version "a" combined with a chimeric H chain was generated, and was tested for the binding activity to the antigen by the cell ELISA. It was found to have the binding activity equal to or higher than that of the chimeric antibody. On the other hand, the neutralizing activity against the antigen was weak as compared to that of the positive control chimeric antibody. Therefore, it was decided to perform the version-up of the humanized L chain by FR-shuffling. The chimeric antibody used herein was the one that was expressed in COS-7 cells, purified, and evaluated.

(iii) Combination of the Humanized H Chain Version "a" and the Humanized L Chain Version "a"

An antibody (a-a) which is the humanized H chain version "a" combined with the humanized L chain version "a" was generated, and was tested for the binding activity to the antigen by the cell ELISA. The amount bound to the antigen was found to be decreased in the high concentration side. The neutralizing activity against the antigen by FXa production-inhibition was weak as compared to that of the positive control chimeric antibody. Therefore, it was decided to perform the version-up of the humanized H chain and L chain by FR-shuffling. The chimeric antibody used herein was the one that was expressed in COS-7 cells, purified, and evaluated.

(iv) Combination of the Humanized H Chain Versions "b", "c", and "d", and a Chimeric L Chain Antibodies ("b-ch", "c-ch", and "d-ch", respectively) which are the humanized H chain subjected to version-up by FR-shuffling combined with a chimeric L chain were generated, and were tested for the binding activity to the antigen by the cell ELISA. "d-ch" exhibited a binding activity equal to that of the chimeric antibody, and "b-ch" and "c-ch" exhibited a slightly lower binding activity. On the other hand, the neutralizing activity against the antigen as compared to the that of positive control chimeric antibody was almost equal in "b-ch", and slightly weak in "d-ch". In version "c-ch", it was significantly weaker than that of the chimeric antibody. Therefore, the humanized H chain versions "b" and "d" were considered the ones of the humanized H chain to exhibit a high activity.

(v) Combination of the Humanized H Chain Version "b" and the Humanized L Chain Version "a"

An antibody (b-a) which is the humanized H chain version "b" subjected to version-up by FR-shuffling combined with the humanized L chain version "a" was generated, and was tested for the binding activity to the antigen by the cell ELISA. The amount bound to the antigen was found to be decreased at the high concentration. On the other hand, the neutralizing activity against the antigen was significantly weak as compared to that of the positive control chimeric antibody. Therefore, "b-a" and "a-a" were the ones that exhibit a high activity. The chimeric antibody used herein was the one that was expressed in COS-7 cells, purified, and evaluated.

(vi) Combination of the Humanized L Chain Versions "b" and "c", and a Chimeric H Chain Antibodies ("ch-b" and "ch-c", respectively) which are the humanized L chain versions "b" and "c" combined with a chimeric H chain were generated, and both of them were found to have the binding activity to the antigen and the neutralizing activity against the antigen equal to the chimeric antibody. Therefore, versions "b" and "c" were chosen as a candidate for a humanized antibody L chain. Mouse antibody-derived version "b" which is one amino acid fewer in the amino acid residue number is considered to be superior to version "c" in terms of antigenicity. The chimeric antibody used herein was the one that was expressed in CHO cells DG44, purified, and evaluated. In the evaluation hereinafter the antibody was used as the positive control.

(vii) Combination of the Humanized H Chain Version "b" and the Humanized L Chain Versions "b" and "c"

Antibodies ("b-b" and "b-c", respectively) which are the humanized H chain version "b" combined with the humanized L chain versions "b" and "c" were generated, and tested for the binding activity to the antigen and the neutralizing activity against the antigen. Both of them had a slightly lower activity than that of the chimeric antibody in both the binding activity and the neutralizing activity.

(viii) Combination of the Humanized H Chain Versions "b" and "d", and the Humanized L Chain Version "b"

Antibodies ("b-b" and "d-b", respectively) which are the humanized H chain subjected to version-up by FR-shuffling combined with the humanized L chain version "b" were generated, and were tested for the binding activity to the antigen by the cell ELISA. "d-b" exhibited a binding activity equal to that of the chimeric antibody, and "b-b" exhibited a slightly lower binding activity at the high concentration. On the other hand, the neutralizing activity against the antigen as compared to that of the positive control chimeric antibody was slightly low in "b-b", and significantly weak in "d-b". Therefore, it was shown that "b-b" is a high neutralizing activity version, whereas "d-b" is a high binding activity version.

(ix) Combination of the Humanized H Chain Version "e", and a Chimeric L Chain and the Humanized L Chain Version "b"

Antibodies ("e-ch" and "e-b", respectively) which are the humanized L chain version "e" combined with a chimeric L chain and the humanized version "b" were generated. "e-ch" exhibited a binding activity to the antigen equal to that of the chimeric antibody, but in "e-b" the amount of antibody expressed was very little and most of the binding activity was lost. The neutralizing activity against the antigen of "e-ch" was significantly low as compared to that of the chimeric antibody. Therefore, it was concluded that the H chain version "e" combined with L chain version "b" did not work well.

(x) Combination of the Humanized H Chain Versions "f", "g", and "h", and the Humanized L Chain Version "b"

Antibodies ("f-b", "g-b", and "h-b", respectively) which are the humanized H chain versions "f", "g", and "h" combined with the humanized L chain version "b" were generated. In "f-b" and "h-b" antibody, the amount of antibody expressed was very little. For versions "f" and "h", antibodies combined with the chimeric L chain were generated, but were not expressed. "g-b" reached saturation at a low concentration, and exhibited a binding activity weaker than that of the chimeric antibody. The neutralizing activity against the antigen of "g-b" was significantly weak as compared to that of the chimeric antibody.

(xi) Combination of the Humanized H Chain Versions "b1" and "d1", and the Humanized L Chain Version "b"

Antibodies ("b1-b" and "d1-b", respectively) which are the humanized H chain versions "b1" and "d1" combined with the humanized L chain version "b" were generated. Almost no antibody was expressed in any of them. For these, antibodies combined with a chimeric L chain were generated, but were not expressed.

(xii) Combination of the Humanized H Chain Versions "b3" and "d3", and the Humanized L Chain Version "b"

Antibodies ("b3-b" and "d3-b", respectively) which are the humanized'H chain versions "b3" and "d3" combined with the humanized L chain version "b" were generated. The binding activity to the antigen of "d3-b" was slightly lower than that of the chimeric antibody, and that of "b3-b" was much lower. The neutralizing activity against the antigen of "b3-b" was higher than that of "b-b", but was lower than that of the chimeric antibody, and "d3-b" and "b-b" remained equal in activity.

(xiii) Combination of the Humanized H Chain Versions "i" and "j", and a Chimeric L Chain and the Humanized L Chain Version "b"

Antibodies ("i-ch" and "j-ch", respectively) which are the humanized H chain versions "i" and "j" combined with a chimeric L chain, and antibodies ("i-b" and "j-b", respectively) combined with the humanized L chain version "b" were generated, and were tested for the binding to the antigen and the neutralizing activity against the antigen. The binding activity of any of the antibodies was almost equal to that of the chimeric antibody. "i-ch" exhibited the neutralizing activity higher than that of the chimeric antibody, and "j-ch" was significantly lower than that of the chimeric antibody. "i-b" exhibited the neutralizing activity equal to that of the chimeric antibody, and "j-b" exhibited a significantly weaker neutralizing activity than that of that of the chimeric antibody.

(xiv) The Humanized L Chain Versions "b1" and "b2"

When antibodies ("ch-b1" and "ch-b2", respectively) which are the humanized L chain versions "b1" and "b2" combined with a chimeric H chain were generated, both of them exhibited the binding activity to the antigen equal to that of the chimeric antibody. For the neutralizing activity against the antigen, "ch-b1" exhibited the binding activity equal to that of the chimeric antibody, while "ch-b2" exhibited an activity slightly higher than that of the chimeric antibody at the high concentration. Versions "b1" and "b2" can be candidates of a humanized antibody L chain, but "b2" is superior in that it has a stronger activity.

(xv) Combination of the Humanized H Chain Version "b" and the Humanized L Chain Version "b2"

An antibody ("b-b2") which is the humanized H chain version "b" combined with the humanized L chain version "b2" was generated, and was tested for the binding activity to the antigen and the neutralizing activity against the antigen. The binding activity was slightly lower than that of the chimeric antibody. The neutralizing activity, though slightly higher than that of "b-b", was lower than that of "i-b".

(xvi) Combination of the Humanized H Chain Version "i" and, the Humanized L Chain Version "b1" or "b2"

Antibodies ("i-b1" and "i-b2", respectively) which are the humanized H chain version "i" combined with the humanized L chain version "b1" or "b2" were generated, and were tested for the binding activity to the antigen and the neutralizing activity against the antigen. The binding activity of "i-b2" was almost equal to that of the chimeric antibody, and that of "i-b1" was slightly lower than that of chimeric antibody. The neutralizing activity of "i-b1" and "i-b2" was higher than that of the chimeric antibody and "i-b", which was in a decreasing order of "i-b2">"i-b1".

Reference Example 7

Preparation of CHO Cell-Producing Humanized Antibody and the Evaluation of its Activity (1) Establishment of a Cell Line that Stably Produces CHO In order to establish cell lines that stably produce a humanized antibody (b-b, i-b, and i-b2), an antibody expression gene vector was introduced into CHO cells (DG44) acclaimed to a serum-free medium.

Plasmid DNA, hHvb-hLvb/N5KG4P, hHvi-hLvb/N5KG4P, and hHvi-hLvb2/N5KG4P were digested with the restriction enzyme SspI (Takara Shuzo) and linearized, which was extracted with phenol and chloroform, and purified by ethanol precipitation. The linearized expression gene vector was introduced into the DG44 cells using the electroporation instrument (Gene Pulser; Bio Rad). The DG44 cells were suspended in PBS at a cell concentration of $1 \times 10^7$ cells/ml, and to about 0.8 ml of this suspension 10 or 50 µg of the DNA was added, which was subjected to pulses of 1,500 V and 25 µF capacity.

After 10 minutes of the recovery period at room temperature, the treated cells were suspended in a CHO—S—SFMII medium (GIBCO) containing hypoxanthine/thymidine (GIBCO) (hereinafter referred to as HT), which was inoculated on two 96-well plates (Falcon) at 100 µl/well, and cultured in a $CO_2$ incubator. Eight to nine hours after the start of culturing, 100 µl/well of the CHO—S—SFMII medium containing HT and 1 mg/ml GENETICIN (GIBCO) was added to change to 500 µg/ml of the GENETICIN selection medium, and the cells into which the antibody gene had been introduced were selected. The medium was changed with a fresh one once every 3-4 days with ½ the volume. At a time point about 2 weeks after changing to the selection medium, an aliquot of the culture supernatant was recovered from the well in which a favorable cell growth was observed 4-5 days later. The concentration of antibody expressed in the culture supernatant was measured by the ELISA described above for measuring antibody concentration, and cells having a high production yield of antibody were selected.

(2) Large Scale Purification of Humanized Antibody

After the DG44 cell lines selected as above that produce the humanized antibody ("b-b", "i-b", and "i-b2") were cultured for a few days in a 500 ml/bottle of the CHO—S—SFMII medium using a 2 L roller bottle (CORNING), the culture medium was harvested and a fresh CHO—S—SFMII medium was added and cultured again. The culture medium was centrifuged to remove the cell debris, and filtered with a 0.22 µm or 0.45 µm filter. By repeating this, a total of about 2 L each of the culture supernatant was obtained. From the culture supernatant obtained, antibody was purified by the ConSep LC100 system (Millipore) connected to the Protein A affinity column (Poros).

(3) Measurement of Antibody Concentration by ELISA

ELISA plates for measurement of antibody concentration were prepared as follows: Each well of a 96-well ELISA plate (Maxisorp, NUNC) was immobilized with 100 µl of goat anti-human IgGγ antibody (BioSource) prepared to a concentration of 1 µg/ml with CB. After blocking with 200 µl of DB, the culture supernatant of the CHO cells in which antibody had been expressed or the purified antibody was serially diluted with DB, and added to each well.

After incubating at room temperature for 1 hour and washing with RB, 100 µl of alkaline phosphatase-conjugated goat anti-human IgGγ antibody (BioSource) diluted 1000-fold with DB was added. After incubating at room temperature for 1 hour and washing with RB, 100 µl of the substrate solution was added, and then the absorbance at 405/655 nm was measured using the Microplate Reader (Bio Rad). As the standard for the measurement of concentration, human IgG4κ (The Binding Site) was used.

(4) Measurement of Activity of Binding to the Antigen

Cell ELISA plates for measurement of antigen binding were prepared as follows. Cells used were human bladder carcinoma cells J82 (ATCC HTB-1), which were inoculated onto a 96-well cell culture plate at a cell count of $1 \times 10^5$ cells. This was cultured (RPMI1640 medium containing 10% fetal bovine serum (GIBCO)) for one day in a $CO_2$ incubator to allow the cells to be attached thereto.

After discarding the culture liquid, each well was washed twice with PBS. 100 µl of PFA/PBS was added to each well, and placed on ice for 10 minutes to immobilize the cells.

PFA/PBS was discarded, and each well was washed twice with 300 µl of PBS and then blocked with 250 µl of DB. Based on the above result of measurement, the purified antibody was serially diluted with DB starting at 10 µg/ml by a factor of 2, 100 µl of which was added to each well. After incubating at room temperature for 2 hours and washing with RB, 100 µl of alkaline phosphatase-conjugated goat anti-human IgGγ antibody (BioSource) diluted 1000-fold with DB was added. After incubating at room temperature for 1 hour and washing with RB, 100 µl of the substrate solution was added, and then absorbance at 405/655 nm was measured using the Microplate Reader (Bio-Rad).

(5) Measurement of Neutralizing Activity Against TF (Factor Inhibiting Activity Against the FXa Production)

The Factor Xa production-inhibiting activity of humanized antibody was measured with the inhibiting activity against the Factor Xa production activity by the human placenta-derived thromboplastin, Thromborel S (Boehringer AG), as an index. Thus, 60 µl of the buffer (TBS containing 5 mM $CaCl_2$ and 0.1% BSA) was added to 10 µl of 5 mg/ml Thromborel S and 10 µl of the antibody, which was then incubated in a 96-well plate at room temperature for 1 hour. The antibody was serially diluted with the buffer starting at 200 µg/ml by a factor of 5.

Ten µl each of 3.245 µg/ml human Factor X (Celsus Laboratories) and 82.5 ng/ml human Factor VIIa (Enzyme Research) were added thereto, and were further incubated at room temperature for 45 minutes. Ten µl of 0.5 M EDTA was added to stop the reaction. Fifty µl of the chromogenic substrate solution was added thereto and the absorbance at 405/655 nm was determined by the Microplate Reader (Bio Rad). After reacting at room temperature for 30 minutes, the absorbance at 405/655 nm was measured again. The residual activity (%) was determined from each change in absorbance with the absorbance change for 30 minutes at no antibody addition as a 100% activity.

The chromogenic substrate solution was prepared by dissolving the Testzyme chromogenic substrate S-2222 (Chromogenix) according to the attached instructions, and mixing with a polybrene solution (0.6 mg/ml hexadimethylene bromide, SIGMA) at 1:1.

(6) Measurement of Neutralizing Activity Against TF (Inhibiting Activity Against the FX-Binding)

The inhibiting activity against the FX-binding of humanized antibody was measured using the human placenta-derived thromboplastin, Thromborel S (Boehringer AG), in which a complex of TF and Factor VIIa had previously been formed and the inhibiting activity against the FX-binding was measured with the Factor Xa production activity of the TF-FVIIa complex as an index. Thus, 60 µl of the buffer (TBS containing 5 mM $CaCl_2$ and 0.1% BSA) was added to 10 µl of 5 mg/ml Thromborel S and 10 µl of 82.5 ng/ml human Factor VIIa (Enzyme Research), which was preincubated in a 96-well plate at room temperature for 1 hour.

Ten µl of the antibody solution was added thereto, incubated at room temperature for 5 minutes, and 10 µl of 3.245 µg/ml human Factor X (Celsus Laboratories) was added and was further incubated at room temperature for 45 minutes. The antibody was serially diluted with the buffer starting at 200 µg/ml by a factor of 2. Ten µl of 0.5 M EDTA was added to stop the reaction. Fifty µl of the chromogenic substrate solution was added thereto and the absorbance at 405/655 nm was determined by the Microplate Reader (Bio Rad). After reacting at room temperature for 30 minutes, the absorbance at 405/655 nm was measured again. The residual activity (%) was determined from each change in absorbance with the absorbance change for 30 minutes at no antibody addition as a 100% activity.

The chromogenic substrate solution was prepared by dissolving the Testzyme chromogenic substrate S-2222 (Chromogenix) according to the attached instructions, and mixing with a polybrene solution (0.6 mg/ml hexadimethylene bromide, SIGMA) at 1:1.

(7) Measurement of Neutralizing Activity Against the Inhibiting Activity Against the (Plasma Coagulation)

The neutralizing activity against TF (inhibiting activity against the plasma coagulation) of humanized antibody was measured using, as an index, prothrombin time determined using the human placenta-derived thromboplastin, Thromborel S (Boehringer AG). Thus, 100 µl of human plasma (Cosmo Bio) was placed into a sample cup, to which 50 µl of antibody diluted at various concentrations was added, and heated at 37° C. for 3 minutes. Fifty µl of 1.25 mg/ml Thromborel S that had previously been preheated at 37° C. was added to start plasma coagulation. The coagulation time was measured using the Amelung KC-10A connected to the Amelung CR-A (both from M. C. Medical).

The antibody was serially diluted with TBS containing 0.1% BSA (hereinafter referred to as BSA-TBS) starting at 80 µg/ml by a factor of 2. With the coagulation time of no antibody addition as 100% TF plasma coagulation activity, the residual TF activity was calculated from each coagulation time at antibody addition based on a standard curve obtained by plotting the concentration of Thromborel S and the coagulation time.

The standard curve was created from the various concentration of Thromborel S and the coagulation time was measured. Fifty µl of BSA-TBS was added to 50 µl of appropriately diluted Thromborel S, which was heated at 37° C. for 3 minutes, 100 µl of human plasma preheated at 37° C. was added to start coagulation, and the coagulation time was determined. Thromborel S was serially diluted with the Hank's buffer (GIBCO) containing 25 mM $CaCl_2$ starting at 6.25 mg/ml by a factor of 2. The Thromborel S concentration was plotted on the abscissa, and the coagulation time on the ordinate on a log-log paper, which was rendered a standard curve.

(8) Activity Evaluation

All humanized antibodies, "b-b", "i-b", and "i-b2" had an activity equal to or greater than that of the chimeric antibody (FIG. 1). For inhibiting activity against FXa production, inhibiting activity FX-binding, and inhibiting activity against plasma coagulation as well, the humanized antibodies, "b-b", "i-b", and "i-b2" had an activity equal to or greater than that of the chimeric antibody, and the activity was of a decreasing order "i-b2">"i-b">"b-b" (FIGS. 2, 3, and 4).

The invention claimed is:

1. A method for suppressing hypertrophy of the vascular intima caused by expression of tissue factor in a patient in need thereof, comprising administering to the patient a therapeutically effective amount of an antibody that upon binding to human tissue factor (human TF), the antibody binds to an inhibitory site for binding a complex human TF and Factor VIIa to Factor X,
   wherein the antibody is a humanized antibody of version b-b, i-b, or i-b2, wherein said humanized antibody version has, respectively, the heavy and light chain pairings of SEQ ID NO: 29 and SEQ ID NO: 88 for version b-b; SEQ ID NO: 59 and SEQ ID NO: 88 for version i-b; and SEQ ID NO: 59 and SEQ ID NO: 98 for version i-b2, and wherein there is a constant region and the constant region is a constant region of human IgG.

2. A method for suppressing hypertrophy of the vascular intima caused by expression of tissue factor in a patient in need thereof, comprising administering to the patient a therapeutically effective amount of an antibody that upon binding to human tissue factor (human TF), the antibody binds to an inhibitory site for binding a complex human TF and Factor VIIa to Factor X,
   wherein the antibody is an altered antibody comprising H chains and L chains, wherein the H chain contains CDRs contained in SEQ ID NO: 59 and the L chain contains CDRs contained in SEQ ID NO: 98.

3. A method for suppressing hypertrophy of the vascular intima caused by expression of tissue factor in a patient in need thereof, comprising administering to the patient a therapeutically effective amount of an antibody that upon binding to human tissue factor (human TF), the antibody binds to an inhibitory site for binding a complex human TF and Factor VIIa to Factor X,
   wherein the antibody that binds to an inhibitory site for binding a complex of human TF and Factor VIIa to Factor X, upon binding to human TF, has CDRs which are the same as CDRs of version i-b2 antibody, wherein the version i-b2 antibody is an antibody in which variable regions have SEQ ID NO: 59 and SEQ ID NO: 98, and constant regions are of human IgG.

* * * * *